US012691235B2

(12) United States Patent
Landa et al.

(10) Patent No.: US 12,691,235 B2
(45) Date of Patent: Jul. 28, 2026

(54) CARTRIDGE UNIT COUPLER

(71) Applicant: Syqe Medical Ltd., Tel-Aviv (IL)

(72) Inventors: Shay Landa, Tel-Aviv (IL); Roee Lifshitz, Moshav Beit Hillel (IL); Abraham Meyer, Tel-Aviv (IL); Binyamin Schwartz, Sde Eliezer (IL); Harel Gur, Kibbutz Mefalsim (IL)

(73) Assignee: Syqe Medical Ltd., Tel-Aviv (IL)

( * ) Notice: Subject to any disclaimer, the term of this patent is extended or adjusted under 35 U.S.C. 154(b) by 1121 days.

(21) Appl. No.: 17/288,960

(22) PCT Filed: Oct. 28, 2019

(86) PCT No.: PCT/IL2019/051163
§ 371 (c)(1),
(2) Date: Apr. 27, 2021

(87) PCT Pub. No.: WO2020/089890
PCT Pub. Date: May 7, 2020

(65) Prior Publication Data
US 2021/0402109 A1      Dec. 30, 2021

Related U.S. Application Data

(60) Provisional application No. 62/751,636, filed on Oct. 28, 2018.

(51) Int. Cl.
A61M 15/00            (2006.01)

(52) U.S. Cl.
CPC .... A61M 15/0001 (2014.02); A61M 15/0053 (2014.02); A61M 15/0081 (2014.02);
(Continued)

(58) Field of Classification Search
CPC ...... A61M 15/00–0003; A61M 15/0028–0083
See application file for complete search history.

(56) References Cited

U.S. PATENT DOCUMENTS

| 3,203,432 A | 8/1965 | Green et al. |
| 3,894,544 A | 7/1975 | Egri |

(Continued)

FOREIGN PATENT DOCUMENTS

| AU | 199641966 | 5/1996 |
| AU | 708269 | 7/1999 |

(Continued)

OTHER PUBLICATIONS

International Preliminary Report on Patentability Dated May 6, 2021 From the International Bureau of WIPO Re. Application No. PCT/IL2019/051163. (6 Pages).

(Continued)

*Primary Examiner* — Rachel T Sippel

(57) ABSTRACT

Some embodiments relate to a cartridge for use with an inhaler, the cartridge comprising: a plurality of source material units and a unit coupler configured for selectively interlocking to each of the source material units so that when the cartridge is operably attached to the inhaler, manipulation of the unit coupler moves the interlocked source material unit away from or back into the cartridge; the unit coupler and each of the source material units being formed with an interlocking geometry in which a protrusion of one fits within a respective recess of the other.

36 Claims, 15 Drawing Sheets

(52) U.S. Cl.
CPC ..... *A61M 15/0046* (2014.02); *A61M 15/0048* (2014.02); *A61M 2205/103* (2013.01); *A61M 2205/3306* (2013.01); *A61M 2205/52* (2013.01); *A61M 2205/6027* (2013.01)

(56) References Cited

U.S. PATENT DOCUMENTS

| | | | |
|---|---|---|---|
| 4,603,030 A | 7/1986 | McCarthy |
| 4,735,358 A | 4/1988 | Morita et al. |
| 4,966,171 A | 10/1990 | Serrano et al. |
| 4,969,477 A | 11/1990 | Yagisawa |
| 5,023,020 A | 6/1991 | Machida et al. |
| 5,036,503 A | 7/1991 | Tomita |
| 5,086,978 A | 2/1992 | Fertig |
| 5,105,838 A | 4/1992 | White et al. |
| 5,301,666 A | 4/1994 | Lerk et al. |
| 5,333,106 A | 7/1994 | Lanpher et al. |
| 5,345,350 A | 9/1994 | Ellis et al. |
| 5,388,594 A | 2/1995 | Counts et al. |
| 5,404,871 A | 4/1995 | Goodman et al. |
| 5,443,606 A | 8/1995 | Hassenboehler, Jr. et al. |
| 5,449,091 A | 9/1995 | Dalziel |
| 5,450,391 A | 9/1995 | Pollard |
| 5,479,948 A | 1/1996 | Counts et al. |
| 5,503,869 A | 4/1996 | Van Oort |
| 5,522,383 A | 6/1996 | Calvert et al. |
| 5,530,225 A | 6/1996 | Hajaligol |
| 5,546,965 A | 8/1996 | White |
| 5,565,148 A | 10/1996 | Pendergrass, Jr. |
| 5,573,692 A | 11/1996 | Das et al. |
| 5,649,554 A | 7/1997 | Sprinkel et al. |
| 5,655,520 A | 8/1997 | Howe et al. |
| 5,792,057 A | 8/1998 | Rubsamen et al. |
| 5,805,768 A | 9/1998 | Schwartz et al. |
| 5,819,756 A | 10/1998 | Miclordt |
| 5,855,564 A | 1/1999 | Ruskowicz |
| 6,034,926 A | 3/2000 | Dang et al. |
| 6,179,164 B1 | 1/2001 | Fuchs |
| 6,547,229 B1 | 4/2003 | Hanson et al. |
| 6,703,418 B2 | 3/2004 | Plasse |
| 6,713,024 B1 | 3/2004 | Arnell et al. |
| 6,761,164 B2 | 7/2004 | Amirpour et al. |
| 6,871,647 B2 | 3/2005 | Allan et al. |
| 7,088,914 B2 | 8/2006 | Whittle et al. |
| 7,169,378 B2 | 1/2007 | Rabinowitz et al. |
| 7,287,530 B1 | 10/2007 | Stuart |
| 7,376,344 B2 | 5/2008 | Manne |
| 7,389,943 B2 | 6/2008 | Jaworski |
| 7,505,259 B2 | 3/2009 | Elbaum |
| 7,537,005 B2 | 5/2009 | Dave |
| 7,690,076 B2 | 4/2010 | Tannous |
| 7,942,388 B2 | 5/2011 | Suissa et al. |
| 7,987,846 B2 | 8/2011 | Hale et al. |
| 8,235,037 B2 | 8/2012 | Hale et al. |
| 8,408,200 B2 | 4/2013 | Clark et al. |
| 8,490,627 B2 | 7/2013 | Levin et al. |
| 8,615,407 B2 | 12/2013 | Hyde et al. |
| 9,775,379 B2 | 10/2017 | Davidson et al. |
| 9,802,011 B2 | 10/2017 | Davidson et al. |
| 9,943,114 B2 | 4/2018 | Batista |
| 9,980,518 B1 | 5/2018 | Most et al. |
| 9,993,602 B2 | 6/2018 | Davidson et al. |
| 10,080,851 B2 | 9/2018 | Davidson et al. |
| 10,099,020 B2 | 10/2018 | Davidson et al. |
| 10,179,215 B2 | 1/2019 | Raichman |
| 10,299,515 B2 | 5/2019 | Krietzman |
| 11,006,661 B2 | 5/2021 | Valadi |
| 11,044,950 B2 | 6/2021 | Collett et al. |
| 11,071,712 B2 | 7/2021 | Davidson et al. |
| 11,311,480 B2 | 4/2022 | Davidson et al. |
| 2001/0027789 A1 | 10/2001 | Goede et al. |
| 2001/0035184 A1 | 11/2001 | Schuler et al. |
| 2002/0078951 A1 | 6/2002 | Nichols et al. |
| 2002/0168322 A1 | 11/2002 | Clark et al. |
| 2003/0037785 A1 | 2/2003 | Sonntag |

| | | | |
|---|---|---|---|
| 2003/0041859 A1 | 3/2003 | Abrams et al. |
| 2003/0049025 A1 | 3/2003 | Neumann et al. |
| 2003/0062042 A1 | 4/2003 | Wensley et al. |
| 2003/0136420 A1 | 7/2003 | Kraker |
| 2003/0163099 A1 | 8/2003 | Wermeling et al. |
| 2003/0168057 A1 | 9/2003 | Snyder et al. |
| 2003/0200964 A1 | 10/2003 | Blakley et al. |
| 2004/0045567 A1 | 3/2004 | Lewis et al. |
| 2004/0069798 A1 | 4/2004 | Grey et al. |
| 2004/0084044 A1 | 5/2004 | Childers et al. |
| 2004/0094152 A1 | 5/2004 | Harvey et al. |
| 2004/0099266 A1 | 5/2004 | Cross et al. |
| 2004/0188546 A1 | 9/2004 | Tabata et al. |
| 2004/0192760 A1 | 9/2004 | Whittle et al. |
| 2004/0234699 A1 | 11/2004 | Hale et al. |
| 2005/0063686 A1 | 3/2005 | Whittle et al. |
| 2005/0126562 A1 | 6/2005 | Rabinowitz et al. |
| 2005/0161467 A1 | 7/2005 | Jones |
| 2005/0244521 A1 | 11/2005 | Strickland et al. |
| 2005/0268909 A1 | 12/2005 | Bonney et al. |
| 2005/0268911 A1 | 12/2005 | Cross et al. |
| 2006/0102175 A1 | 5/2006 | Nelson |
| 2006/0120962 A1 | 6/2006 | Rabinowitz et al. |
| 2006/0157491 A1 | 7/2006 | Whittle et al. |
| 2006/0167084 A1 | 7/2006 | Dudley |
| 2006/0258738 A1 | 11/2006 | Dieterich |
| 2007/0023060 A1 | 2/2007 | Ra |
| 2007/0072938 A1 | 3/2007 | Rose |
| 2007/0074721 A1 | 4/2007 | Harmer et al. |
| 2007/0102013 A1 | 5/2007 | Adams et al. |
| 2007/0122353 A1 | 5/2007 | Hale et al. |
| 2007/0163580 A1 | 7/2007 | Braithwaite |
| 2007/0209661 A1 | 9/2007 | Smyth et al. |
| 2007/0240712 A1 | 10/2007 | Fleming et al. |
| 2007/0286816 A1 | 12/2007 | Hale et al. |
| 2008/0072898 A1 | 3/2008 | Quoniam |
| 2008/0078382 A1 | 4/2008 | LeMahieu et al. |
| 2008/0140250 A1 | 6/2008 | Dave |
| 2008/0159961 A1 | 7/2008 | Woolfe et al. |
| 2008/0176885 A1 | 7/2008 | Holtman et al. |
| 2008/0181942 A1 | 7/2008 | Zajicek |
| 2008/0199161 A1 | 8/2008 | Hickey et al. |
| 2008/0202515 A1 | 8/2008 | Hodson et al. |
| 2008/0299048 A1 | 12/2008 | Hale et al. |
| 2008/0308101 A1 | 12/2008 | Spandorfer |
| 2008/0311176 A1 | 12/2008 | Hale et al. |
| 2009/0060287 A1 | 3/2009 | Hyde et al. |
| 2009/0084865 A1 | 4/2009 | Maharajh |
| 2009/0151722 A1 | 6/2009 | Eason et al. |
| 2009/0194105 A1 | 8/2009 | Besseller et al. |
| 2009/0197941 A1 | 8/2009 | Guy et al. |
| 2009/0241949 A1 | 10/2009 | Smutney et al. |
| 2009/0281398 A1 | 11/2009 | Hogan |
| 2009/0293874 A1 | 12/2009 | Braithwaite |
| 2009/0293888 A1 | 12/2009 | Williams et al. |
| 2009/0293892 A1 | 12/2009 | Williams et al. |
| 2009/0308390 A1 | 12/2009 | Smutney et al. |
| 2009/0320836 A1 | 12/2009 | Baker, Jr. |
| 2010/0012118 A1 | 1/2010 | Storz |
| 2010/0035978 A1 | 2/2010 | Guy et al. |
| 2010/0154795 A1 | 6/2010 | Pentafragas |
| 2010/0168228 A1 | 7/2010 | Bose |
| 2010/0181387 A1 | 7/2010 | Zaffaroni et al. |
| 2010/0204602 A1 | 8/2010 | Addington et al. |
| 2010/0250280 A1 | 9/2010 | Sutherland |
| 2010/0294278 A1 | 11/2010 | Mosier et al. |
| 2010/0300442 A1 | 12/2010 | Houzego et al. |
| 2010/0326438 A1 | 12/2010 | Dunne |
| 2011/0030706 A1 | 2/2011 | Gibson et al. |
| 2011/0036346 A1 | 2/2011 | Cohen et al. |
| 2011/0038958 A1 | 2/2011 | Kikuchi et al. |
| 2011/0126827 A1* | 6/2011 | Kaemper .......... A61M 15/0051 128/200.23 |
| 2011/0126831 A1 | 6/2011 | Pernia |
| 2011/0126848 A1 | 6/2011 | Zuber et al. |
| 2011/0240011 A1 | 10/2011 | Caldwell |
| 2011/0244020 A1 | 10/2011 | Hale et al. |
| 2011/0265806 A1 | 11/2011 | Alarcon et al. |
| 2012/0003318 A1 | 1/2012 | Schuler et al. |

(56) References Cited

U.S. PATENT DOCUMENTS

| | | |
|---|---|---|
| 2012/0006700 A1 | 1/2012 | Geboers et al. |
| 2012/0116241 A1 | 5/2012 | Shie et al. |
| 2012/0252885 A1 | 10/2012 | Barbato |
| 2012/0255546 A1 | 10/2012 | Goetz et al. |
| 2012/0291781 A1 | 11/2012 | Kaufmann et al. |
| 2012/0291791 A1 | 11/2012 | Pradeep |
| 2012/0304990 A1 | 12/2012 | Todd |
| 2012/0325227 A1 | 12/2012 | Robinson et al. |
| 2013/0032139 A1 | 2/2013 | Hale et al. |
| 2013/0053719 A1 | 2/2013 | Wekell |
| 2013/0081623 A1 | 4/2013 | Buchberger |
| 2013/0087144 A1 | 4/2013 | Todd |
| 2013/0112197 A1 | 5/2013 | Kruener et al. |
| 2013/0213397 A1 | 8/2013 | Curtis et al. |
| 2013/0218588 A1 | 8/2013 | Kehr et al. |
| 2013/0269694 A1 | 10/2013 | Patton et al. |
| 2013/0276799 A1 | 10/2013 | Davidson et al. |
| 2013/0298905 A1 | 11/2013 | Levin et al. |
| 2013/0304502 A1 | 11/2013 | Cederlund et al. |
| 2013/0304990 A1 | 11/2013 | Bass et al. |
| 2013/0333700 A1 | 12/2013 | Buchberger |
| 2014/0037794 A1 | 2/2014 | Patera et al. |
| 2014/0060525 A1 | 3/2014 | Hale et al. |
| 2014/0060532 A1 | 3/2014 | Hodges et al. |
| 2014/0088045 A1 | 3/2014 | Rigas et al. |
| 2014/0100249 A1 | 4/2014 | Sears et al. |
| 2014/0106324 A1 | 4/2014 | Adams et al. |
| 2014/0144429 A1 | 5/2014 | Wensley et al. |
| 2014/0190496 A1 | 7/2014 | Wensley et al. |
| 2014/0202454 A1 | 7/2014 | Buchberger |
| 2014/0209105 A1 | 7/2014 | Sears et al. |
| 2014/0238423 A1 | 8/2014 | Tucker et al. |
| 2014/0366898 A1 | 12/2014 | Monsces et al. |
| 2014/0373857 A1 | 12/2014 | Steinberg |
| 2014/0373859 A1 | 12/2014 | Raether et al. |
| 2015/0064672 A1 | 3/2015 | Bars |
| 2015/0075521 A1 | 3/2015 | Lee et al. |
| 2015/0090253 A1 | 4/2015 | Farrow |
| 2015/0122252 A1 | 5/2015 | Frija |
| 2015/0136124 A1 | 5/2015 | Aronie et al. |
| 2015/0136158 A1 | 5/2015 | Stevens et al. |
| 2015/0237913 A1 | 8/2015 | Suzuki et al. |
| 2015/0245660 A1 | 9/2015 | Lord |
| 2016/0007653 A1 | 1/2016 | Tu |
| 2016/0044960 A1 | 2/2016 | O'Connor |
| 2016/0089508 A1 | 3/2016 | Smith et al. |
| 2016/0100624 A1 | 4/2016 | Yilmaz et al. |
| 2016/0121057 A1 | 5/2016 | Dyche et al. |
| 2016/0166564 A1 | 6/2016 | Myers et al. |
| 2016/0166786 A1 | 6/2016 | Kinzer |
| 2016/0171164 A1 | 6/2016 | Kinzer |
| 2016/0183589 A1 | 6/2016 | Born et al. |
| 2016/0219938 A1 | 8/2016 | Mamoun et al. |
| 2016/0271347 A1 | 9/2016 | Raichman |
| 2016/0286860 A1 | 10/2016 | Flayler |
| 2016/0295922 A1 | 10/2016 | John et al. |
| 2016/0309774 A1 | 10/2016 | Wand |
| 2016/0309784 A1 | 10/2016 | Silvestrini et al. |
| 2016/0331022 A1 | 11/2016 | Cameron |
| 2016/0331913 A1 | 11/2016 | Bourque |
| 2016/0345630 A1 | 12/2016 | Mironov et al. |
| 2016/0354561 A1 | 12/2016 | McCullough |
| 2016/0354573 A1 | 12/2016 | Buswell et al. |
| 2017/0056368 A1 | 3/2017 | Hearn et al. |
| 2017/0072145 A1 | 3/2017 | Hadash et al. |
| 2017/0095624 A1 | 4/2017 | Davidson et al. |
| 2017/0106153 A1 | 4/2017 | Davidson et al. |
| 2017/0119050 A1 | 5/2017 | Blandino et al. |
| 2017/0119979 A1 | 5/2017 | Davidson et al. |
| 2017/0119981 A1 | 5/2017 | Davidson et al. |
| 2017/0127727 A1 | 5/2017 | Davidson et al. |
| 2017/0136196 A1 | 5/2017 | Davidson et al. |
| 2017/0150755 A1 | 6/2017 | Batista |
| 2017/0157341 A1 | 6/2017 | Pandya |
| 2017/0157343 A1 | 6/2017 | Davidson et al. |
| 2017/0164657 A1 | 6/2017 | Batista |
| 2017/0203058 A1 | 7/2017 | Davidson et al. |
| 2017/0295848 A1 | 10/2017 | LaMothe |
| 2017/0304567 A1 | 10/2017 | Adelson |
| 2017/0360089 A1 | 12/2017 | Davidson et al. |
| 2018/0043115 A1 | 2/2018 | Gould et al. |
| 2018/0104214 A1 | 4/2018 | Raichman |
| 2018/0110943 A1 | 4/2018 | Raichman |
| 2018/0154103 A1 | 6/2018 | Davis |
| 2018/0263288 A1 | 9/2018 | Goldstein et al. |
| 2018/0318529 A1 | 11/2018 | Davidson et al. |
| 2018/0344954 A1 | 12/2018 | Davidson et al. |
| 2019/0001087 A1 | 1/2019 | Davidson et al. |
| 2019/0009039 A1 | 1/2019 | Davidson et al. |
| 2019/0015382 A1 | 1/2019 | Davidson et al. |
| 2019/0098930 A1 | 4/2019 | Fallon et al. |
| 2019/0124982 A1 | 5/2019 | Atkins et al. |
| 2019/0183185 A1 | 6/2019 | Manas et al. |
| 2019/0192810 A1 | 6/2019 | Trzecieski |
| 2019/0290862 A1 | 9/2019 | Davidson et al. |
| 2020/0367570 A1 | 11/2020 | Batista et al. |
| 2020/0397035 A1 | 12/2020 | Lee et al. |
| 2021/0023316 A1 | 1/2021 | Schorr et al. |
| 2021/0046259 A1 | 2/2021 | Hasegawa et al. |
| 2021/0236414 A1 | 8/2021 | Davidson et al. |
| 2021/0239285 A1 | 8/2021 | Davidson et al. |
| 2021/0298358 A1 | 9/2021 | Ghanouni |
| 2022/0031972 A1 | 2/2022 | Davidson et al. |
| 2022/0096760 A1 | 3/2022 | Schwartz et al. |
| 2022/0183962 A1 | 6/2022 | Davidson et al. |
| 2022/0211958 A1 | 7/2022 | Davidson et al. |
| 2022/0241523 A1 | 8/2022 | Davidson et al. |
| 2023/0390186 A1 | 12/2023 | Davidson et al. |
| 2024/0050397 A1 | 2/2024 | Davidson et al. |
| 2024/0325661 A1 | 10/2024 | Davidson et al. |

FOREIGN PATENT DOCUMENTS

| | | |
|---|---|---|
| CA | 2599022 | 9/2005 |
| CA | 2890204 | 6/2014 |
| CA | 3025407 | 11/2017 |
| CN | 1323231 | 11/2001 |
| CN | 2816102 | 9/2006 |
| CN | 1871044 | 11/2006 |
| CN | 1925883 | 3/2007 |
| CN | 101053685 | 10/2007 |
| CN | 101130121 | 2/2008 |
| CN | 101132823 | 2/2008 |
| CN | 101360528 | 2/2009 |
| CN | 101415457 | 4/2009 |
| CN | 101980743 | 2/2011 |
| CN | 102245151 | 11/2011 |
| CN | 102355914 | 2/2012 |
| CN | 102438602 | 5/2012 |
| CN | 102438685 | 5/2012 |
| CN | 203166473 | 8/2013 |
| CN | 105935470 | 9/2016 |
| CN | 106659858 | 5/2017 |
| CN | 108260855 | 7/2018 |
| CN | 108712918 | 10/2018 |
| EA | 201100197 | 3/2012 |
| EP | 0216926 | 3/1991 |
| EP | 0539674 | 5/1993 |
| EP | 0547429 | 6/1993 |
| EP | 0950423 | 10/1999 |
| EP | 1358902 | 11/2003 |
| EP | 1992381 | 11/2008 |
| EP | 2145643 | 1/2010 |
| EP | 2292108 | 3/2011 |
| EP | 3160553 | 5/2017 |
| GB | 2108390 | 5/1983 |
| GB | 2340758 | 3/2000 |
| GB | 2456183 | 7/2009 |
| GB | 2495771 | 4/2013 |
| IL | 103908 | 10/1996 |
| JP | 2002-527151 | 8/2002 |
| JP | 2003-503117 | 1/2003 |
| JP | 2003-079731 | 3/2003 |
| JP | 2003-275214 | 9/2003 |

(56) References Cited

FOREIGN PATENT DOCUMENTS

| | | |
|---|---|---|
| JP | 2004-283609 | 10/2004 |
| JP | 2004-298331 | 10/2004 |
| JP | 2005-503846 | 2/2005 |
| JP | 2005-516644 | 6/2005 |
| JP | 2005-516647 | 6/2005 |
| JP | 2006-507909 | 3/2006 |
| JP | 2007-0516015 | 6/2007 |
| JP | 2008-501406 | 1/2008 |
| JP | 2008-525108 | 7/2008 |
| JP | 2008-301847 | 12/2008 |
| JP | 2009-509523 | 3/2009 |
| JP | 2009-131686 | 6/2009 |
| JP | 2011-508765 | 3/2011 |
| JP | 2012-110499 | 6/2012 |
| JP | 2012-527329 | 11/2012 |
| JP | 2013-521074 | 6/2013 |
| JP | 2013-521075 | 6/2013 |
| JP | 2013-523395 | 6/2013 |
| JP | 2017-523828 | 8/2017 |
| JP | 2017-530731 | 10/2019 |
| JP | 2020-062479 | 4/2020 |
| KR | 10-1319228 | 10/2013 |
| KR | 10-2017-0024084 | 3/2017 |
| RU | 2153894 | 8/2000 |
| RU | 2413544 | 3/2011 |
| RU | 107026 | 8/2011 |
| RU | 2460677 | 9/2012 |
| RU | 2492876 | 9/2013 |
| RU | 2501577 | 12/2013 |
| RU | 2523642 | 7/2014 |
| RU | 2017102234 | 7/2018 |
| WO | WO 91/11120 | 8/1991 |
| WO | WO 93/24166 | 12/1993 |
| WO | WO 94/09842 | 5/1994 |
| WO | WO 95/16483 | 6/1995 |
| WO | WO 96/32854 | 10/1996 |
| WO | WO 98/04308 | 2/1998 |
| WO | WO 00/21594 | 4/2000 |
| WO | WO 00/21598 | 4/2000 |
| WO | WO 00/24362 | 5/2000 |
| WO | WO 00/28844 | 5/2000 |
| WO | WO 01/00263 | 1/2001 |
| WO | WO 01/17595 | 3/2001 |
| WO | WO 03/020057 | 3/2003 |
| WO | WO 03/030979 A1 | 4/2003 |
| WO | WO 03/037412 | 5/2003 |
| WO | WO 2005/061033 | 7/2005 |
| WO | WO 2005/072719 | 8/2005 |
| WO | WO 2005/072792 | 8/2005 |
| WO | WO 2005/120614 | 12/2005 |
| WO | WO 2006/071512 | 7/2006 |
| WO | WO 2007/018568 | 2/2007 |
| WO | WO 2007/042941 | 4/2007 |
| WO | WO 2008/024408 | 2/2008 |
| WO | WO 2008/024490 | 2/2008 |
| WO | WO 2008/116165 | 9/2008 |
| WO | WO 2009/102976 | 8/2009 |
| WO | WO 2009/124552 | 10/2009 |
| WO | WO 2010/015260 | 2/2010 |
| WO | WO 2011/073306 | 6/2011 |
| WO | WO2011/130183 | 10/2011 |
| WO | WO 2012/006125 | 1/2012 |
| WO | WO 2012/006126 | 1/2012 |
| WO | WO 2012/026963 | 3/2012 |
| WO | WO 2012/038903 | 3/2012 |
| WO | WO 2012/085919 | 6/2012 |
| WO | WO 2013/013808 | 1/2013 |
| WO | WO 2013/057185 | 4/2013 |
| WO | WO 2013/060781 | 5/2013 |
| WO | WO 2013/083636 | 6/2013 |
| WO | WO 2014/037794 | 3/2014 |
| WO | WO 2014/053242 | 4/2014 |
| WO | WO 2014/061477 | 4/2014 |
| WO | WO 2014/085719 | 6/2014 |
| WO | WO 2015/123064 | 8/2015 |
| WO | WO 2015/123317 | 8/2015 |
| WO | WO 2015/175979 | 11/2015 |
| WO | WO 2016/001921 | 1/2016 |
| WO | WO 2016/001922 | 1/2016 |
| WO | WO 2016/001923 | 1/2016 |
| WO | WO 2016/001924 | 1/2016 |
| WO | WO 2016/001925 | 1/2016 |
| WO | WO 2016/001926 | 1/2016 |
| WO | WO 2016/090303 | 6/2016 |
| WO | WO 2016/147188 | 9/2016 |
| WO | WO 2016/172802 | 11/2016 |
| WO | WO 2016/187695 | 12/2016 |
| WO | WO 2016/187696 | 12/2016 |
| WO | WO 2017/118980 | 7/2017 |
| WO | WO 2017/122196 | 7/2017 |
| WO | WO 2017/122201 | 7/2017 |
| WO | WO 2017/178958 | 10/2017 |
| WO | WO 2017/185051 | 10/2017 |
| WO | WO 2018/019855 | 2/2018 |
| WO | WO 2019/138053 | 7/2019 |
| WO | WO 2019/159170 | 8/2019 |
| WO | WO 2020/089890 | 5/2020 |
| WO | WO 2020/161721 | 8/2020 |
| WO | WO 2013/052586 | 3/2021 |

OTHER PUBLICATIONS

Notice of Reason(s) for Rejection Dated Jun. 1, 2021 From the Japan Patent Office Re. Application No. 2020-1101083 and Its Translation Into English. (12 Pages).

International Preliminary Report on Patentability Dated Aug. 19, 2021 From the International Bureau of WIPO Re. Application No. PCT/IL2020/050151. (7 Pages).

Interview Summary Dated Sep. 12, 2022 From the US Patent and Trademark Office Re. U.S. Appl. No. 16/068,373. (2 Pages).

Notice of Reasons for Rejection Dated Aug. 30, 2022 From the Japan Patent Office Re. Application No. 2021-175408 and Its Translation Into English. (12 Pages).

Request for Examination and Search Report Dated Mar. 10, 2023 From the (Rospatent), Federal Government Institution of Industrial Property of the Federal Service of Intellectual Property, Patents and Trademark of the Russian Federation Re. Application No. 2021125574. (9 Pages).

Request for Examination and Search Report Dated Feb. 16, 2023 From the (Rospatent), Federal Government Institution of Industrial Property of the Federal Service of Intellectual Property, Patents and Trademark of the Russian Federation Re. Application No. 202111628 and its Summary in English. (12 Pages).

Communication Pursuant to Article 94(3) EPC Dated May 10, 2024 From the European Patent Office Re. Application No. 20150198.8 (5 Pages).

Interview Summary Dated Dec. 24, 2021 From the US Patent and Trademark Office Re. U.S. Appl. No. 16/068,373. (3 Pages).

Almog et al. "The Pharmacokinetics, Efficacy, and Safety of a Novel Selective-Dose Cannabis Inhaler in Patients With Chronic Pain: A Randomized, Double-Blineed, Placebo-Controlled Trial", European Journal of Pain, 24(8): 1505-1516, Published Online Jun. 12, 2020.

European Search Report and the European Search Opinion Dated Nov. 9, 2021 From the European Patent Office Re. Application No. 21199976.8 (8 Pages).

Notice of Allowance Dated Dec. 20, 2021 from US Patent and Trademark Office Re. U.S. Appl. No. 16/055,269. (158 pages).

European Search Report and the European Search Opinion Dated Dec. 17, 2021 From the European Patent Office Re. Application No. 21196651.0. (7 Pages).

Request for Examination and Search Report Dated Aug. 7, 2024 From the (Rospatent), Federal Government Institution of Industrial Property of the Federal Service of Intellectual Property, Patents and Trademark of the Russian Federation Re. Application No. 2024108351 and Its Translation into English. (21 Pages).

Supplementary European Search Report and the European Search Opinion Dated Jul. 12, 2022 From the European Patent Office Re. Application No. 19880500.4. (11 Pages).

(56) References Cited

OTHER PUBLICATIONS

Bandi et al "From Detection of Individual Metastases to Classification of Lymph Node Status at the Patient Level: The CAMELYON17 Challenge", IEEE Transactions on Medical Imaging,38(2):550-560, Aug. 27, 2018.

Bauer et al. "Tools and Techniques to Standardize Tissue Collection, Transport, and Fixation", Current Pathobiology Reports, 6(2):135-143, Apr. 25, 2018.

Colley et al. "Fixation and Other Pre-Analytical Factors", Dako:10P., Apr. 17, 2017.

Lanng et al. "Quality Assessment of Ki67 Staining Using Cell Line Proliferation Index and Stain Intensity Features", Cytometry, Journal of Quantitative Cell Science, 95(4):381-388, Dec. 17, 2018.

English Translation and Claims Dated Sep. 10, 2024 of Notice of Reasons for Rejection Dated Aug. 27, 2024 From the Japan Patent Office Re. Application No. 2023-061198 and Its Machine Translation Into English. (5 Pages).

Notice of Allowance Dated Sep. 4, 2024 From the US Patent and Trademark Office Re. U.S. Appl. No. 17/694,764.(3 pages).

English Translation Dated Feb. 21, 2022 of Notification of Office Action and Search Report Dated Jan. 20, 2022 From the State Intellectual Property Office of the People's Republic of China Re. Application No. 202011200160.2.1 Pages).

Supplementary European Search Report and the European Search Opinion Dated Nov. 14, 2022 From the European Patent Office Re. Application No. 20751958.8 (8 pages).

Communication Pursuant to Article 94(3) EPC Dated Feb. 6, 2023 From the European Patent Office Re. Application No. 20150198.8 (7 Pages).

Supplementary European Search Report and the European Search Opinion Dated Dec. 16, 2021From the European Patent Office Re. Application No. 19754583.3. (6 Pages).

Grounds of Reason of Rejection Dated Mar. 24, 2022 From the Korean Intellectual Property Office Re. Application No. 10-2017-7002682 and Its Translation Into English. (14 Pages).

Notice of Reasons for Rejection Dated Mar. 22, 2022 From the Japan Patent Office Re. Application No. 2020-101083 and Its Translation Into English. (7 Pages).

Patent Examination Report Dated Mar. 18, 2022 From the Australian Government, IP Australia Re. Application No. 2021204703 with claims. (7 Pages).

Patent Examination Report Dated Mar. 22, 2022 From the Australian Government, IP Australia Re. Application No. 2020205271 with amended Claims. (8 Pages).

Requisition by the Examiner Dated Mar. 29, 2022 From the Innovation, Science and Economic Development Canada, Canadian Intellectual Property Office Re. Application No. 2,953,069 with Claims. (15 Pages).

Requisition by the Examiner Dated Mar. 30, 2022 From the Innovation, Science and Economic Development Canada, Canadian Intellectual Property Office Re. Application No. 2,953,073 with Claims. (18 Pages).

Communication Pursuant to Article 94(3) EPC Dated Dec. 12, 2023 From the European Patent Office Re. Application No. 21159548.3. (4 Pages).

Translation Dated Dec. 12, 2023 of Request for Examination Dated Oct. 18, 2023 From the (Rospatent), Federal Government Institution of Industrial Property of the Federal Service of Intellectual Property, Patents and Trademark of the Russian Federation Re. Application No. 2021114565. (7 Pages).

Supplementary European Search Report and the European Search Opinion Dated Jun. 25, 2024 From the European Patent Office Re. Application No. 24167020.7. (11 Pages).

Patent Examination Report Dated Dec. 7, 2023 From the Australian Government, IP Australia Re. Application No. 2022291563. (4 Pages).

Grounds of Reason of Rejection Dated Sep. 14, 2023 From the Korean Intellectual Property Office Re. Application No. 10-2023-7025097. (5 Pages).

Official Action Dated Aug. 5, 2021 from the US Patent and Trademark Office Re. U.S. Appl. No. 16/030,967. (163 pages).

Request for Examination Dated Oct. 18, 2023 From the (Rospatent), Federal Government Institution of Industrial Property of the Federal Service of Intellectual Property, Patents and Trademark of the Russian Federation Re. Application No. 2021114565. (9 Pages).

Restriction Official Action Dated Mar. 27, 2024 From the US Patent and Trademark Office Re. U.S. Appl. No. 17/428,706. (8 pages).

English Summary Dated Oct. 30, 2023 of Notification of Office Action and Search Report Dated Oct. 16, 2023 From the National Intellectual Property Administration of the People's Republic of China Re. Application No. 202080027182.5 (2 Pages).

Notice of Reason(s) for Rejection Dated Oct. 24, 2023 From the Japan Patent Office Re. Application No. 2021-545436 and Its Translation Into English. (10 Pages).

Patent Examination Report Dated Aug. 13, 2021 From the Australian Government, IP Australia Re. Application No. 2020205271. (7 Pages).

Requisition by the Examiner Dated Aug. 19, 2021 From the Innovation, Science and Economic Development Canada, Canadian Intellectual Property Office Re. Application No. 2,953,074. (16 Pages).

Requisition by the Examiner Dated Aug. 26, 2021 From the Innovation, Science and Economic Development Canada, Canadian Intellectual Property Office Re. Application No. 2,953,082. (28 Pages).

Communication Pursuant to Article 94(3) EPC Dated Dec. 19, 2023 From the European Patent Office Re. Application No. 21196651.0. (5 Pages).

European Search Report and the European Search Opinion Dated Oct. 11, 2021 From the European Patent Office Re. Application No. 21194394.9 (8 Pages).

Notification of Office Action and Search Report Dated Nov. 3, 2021 From the State Intellectual Property Office of the People's Republic of China Re. Application No. 202010701980.3. (10 Pages).

Office Action Dated Nov. 2, 2021 From the Israel Patent Office Re. Application No. 262376 and Its Translation Into English. (7 Pages).

English Summary Dated Jul. 20, 2022 of Notification of Office Action and Search Report Dated Jun. 27, 2022 From the State Intellectual Property Office of the People's Republic of China Re. Application No. 201980081175.0. (1 Page).

Grounds of Reason of Rejection Dated May 22, 2023 From the Korean Intellectual Property Office Re. Application No. 10-2022-7036865 and Its Translation Into English. (6 Pages).

Interview Summary Dated Apr. 12, 2024 from the US Patent and Trademark Office Re. U.S. Appl. No. 16/969,612. (8 pages).

Final Official Action Dated Nov. 30, 2022 from the US Patent and Trademark Office Re. U.S. Appl. No. 16/068,373. (15 pages).

Grounds of Reason of Rejection Dated Apr. 23, 2024 From the Korean Intellectual Property Office Re. Application No. 10-2021-7015766. (8 Pages).

Requisition by the Examiner Dated Apr. 25, 2024 From the Innovation, Science and Economic Development Canada, Canadian Intellectual Property Office Re. Application No. 2,953,073. (3 Pages).

Translation Dated May 2, 2024 of Grounds of Reason of Rejection Dated Apr. 23, 2024 From the Korean Intellectual Property Office Re. Application No. 10-2021-7015766. (6 Pages).

Communication Pursuant to Article 94(3) EPC Dated Jan. 9, 2024 From the European Patent Office Re. Application No. 21199976.8. (5 Pages).

Notice of Reason(s) for Rejection Dated Jan. 9, 2024 From the Japan Patent Office Re. Application No. 2023-061198 and Its Machine Translation Into English. (7 Pages).

Request for Examination and Search Report Dated Feb. 16, 2023 From the (Rospatent), Federal Government Institution of Industrial Property of the Federal Service of Intellectual Property, Patents and Trademark of the Russian Federation Re. Application No. 2021114565 and its Summary in English. (12 Pages).

Translation Dated Mar. 30, 2023 of Request for Examination and Search Report Dated Feb. 16, 2023 From the (Rospatent), Federal Government Institution of Industrial Property of the Federal Service

(56) References Cited

OTHER PUBLICATIONS of Intellectual Property, Patents and Trademark of the Russian Federation Re. Application No. 2021114565 and its Summary in English.(7 Pages).

Official Action Dated Oct. 26, 2023 from the US Patent and Trademark Office Re. U.S. Appl. No. 17/679,190. (91 pages).

Final Official Action Dated Jul. 6, 2021 from the US Patent and Trademark Office Re. U.S. Appl. No. 16/068,373. (33 pages).

Ground(s) of Reason of Rejection Dated Jan. 21, 2022 From the Korean Intellectual Property Office Re. Application No. 10-2017-70023243 and its Translation into English. (13 Pages).

Notification of Office Action and Search Report Dated Jan. 20, 2022 From the State Intellectual Property Office of the People's Republic of China Re. Application No. 202011200160.2. (6 Pages).

Decision on Rejection Dated Apr. 23, 2023 From the State Intellectual Property Office of the People's Republic of China Re. Application No. 201980081175.0. (8 pages).

English Summary Dated Apr. 26, 2023 of Notification of Office Action Dated Apr. 19, 2023 From the State Intellectual Property Office of the People's Republic of China Re. Application No. 202080027182.5. (2 pages).

Notification of Office Action and Search Report Dated Apr. 13, 2023 From the State Intellectual Property Office of the People's Republic of China Re. Application No. 202080027182.5 (11 pages).

Ground(s) of Reason of Rejection Dated Nov. 21, 2022 From the Korean Intellectual Property Office Re. Application No. 10-2022-7038127 and its Translation into English. (5 Pages).

Requisition by the Examiner Dated Nov. 28, 2022 From the Innovation, Science and Economic Development Canada, Canadian Intellectual Property Office Re. Application No. 2,953,069 with Claims. (17 Pages).

Requisition by the Examiner Dated Nov. 28, 2022 From the Innovation, Science and Economic Development Canada, Canadian Intellectual Property Office Re. Application No. 2,953,073. (3 Pages).

Translation Dated Apr. 10, 2023 of Request for Examination and Search Report Dated Mar. 10, 2023 From the (Rospatent), Federal Government Institution of Industrial Property of the Federal Service of Intellectual Property, Patents and Trademark of the Russian Federation Re. Application No. 2021125574. (5 Pages).

Official Action Dated Mar. 30, 2023 From the US Patent and Trademark Office Re. U.S. Appl. No. 17/679,190. (287 Pages).

Translation Dated Mar. 30, 2023 of Request for Examination and Search Report Dated Feb. 16, 2023 From the (Rospatent), Federal Government Institution of Industrial Property of the Federal Service of Intellectual Property, Patents and Trademark of the Russian Federation Re. Application No. 202111628 and its Summary in English.(7 Pages).

Official Action Dated Dec. 20, 2023 from the US Patent and Trademark Office Re. U.S. Appl. No. 16/969,612. (61 pages).

Request for Examination and Search Report Dated Nov. 16, 2023 From the (Rospatent), Federal Government Institution of Industrial Property of the Federal Service of Intellectual Property, Patents and Trademark of the Russian Federation Re. Application No. 2021125574 and It's Machine translation into English. (15 Pages).

English Summary Dated May 4, 2023 of Decision on Rejection Dated Apr. 23, 2023 From the State Intellectual Property Office of the People's Republic of China Re. Application No. 201980081175.0 (1 page).

Grounds of Reason of Rejection Dated Apr. 20, 2023 From the Korean Intellectual Property Office Re. Application No. 10-2022-7045372 and Its Translation Into English. (9 Pages).

Notice of Allowance Dated May 2, 2023 From the US Patent and Trademark Office Re. U.S. Appl. No. 17/238,278. (33 Pages).

Translation Dated Jun. 23, 2023 of Notice of Reason(s) for Rejection Dated Jun. 13, 2023 From the Japan Patent Office Re. Application No. 2022-115378. (4 pages).

Final Notice of Rejection Dated Oct. 30, 2023 From the Korean Intellectual Property Office Re. Application No. 10-2022-7045372 and Its Translation Into English. (7 Pages).

Official Action Dated Aug. 3, 2023 from the US Patent and Trademark Office Re. U.S. Appl. No. 16/969,612. (271 pages).

Translation for the Rejection of Claim 1 Dated May 11, 2023 of Notification of Office Action Dated Apr. 13, 2023 From the State Intellectual Property Office of the People's Republic of China Re. Application No. 202080027182.5. (1 Page).

Communication Pursuant to Article 94(3) EPC Dated Jan. 3, 2024 From the European Patent Office Re. Application No. 19754583.3 (5 Pages).

Examination Report Dated Jan. 18, 2024 From the Australian Government, IP Australia Re. Application No. 2019221321. (4 Pages).

Official Action Dated Jan. 18, 2024 from the US Patent and Trademark Office Re. U.S. Appl. No. 17/694,764. (168 pages).

Apple Inc. "i-Phone 4—Technical Specifications", Retrieved Online, Apple Inc., pp. 1-6, Feb. 19, 2014.

Communication Pursuant to Article 94(3) EPC Dated Dec. 15, 2023 From the European Patent Office Re. Application No. 21194394.9 (6 Pages).

Communication Pursuant to Article 94(3) EPC Dated Dec. 5, 2024 From the European Patent Office Re. Application No. 20751958.8. (6 Pages).

Examination Report Dated Dec. 11, 2024 From the Australian Government, IP Australia Re. Application No. 2022256225. (5 Pages).

Grounds of Reason of Rejection Dated Dec. 19, 2024 From the Korean Intellectual Property Office Re. Application No. 2010-7029927 and Its Machine Translation Into English. (15 Pages).

Official Action Dated Dec. 20, 2024 from the US Patent and Trademark Office Re. U.S. Appl. No. 17/428,706. (46 pages).

Interview Summary Dated Apr. 8, 2025 from the US Patent and Trademark Office Re. U.S. Appl. No. 17/428,706. (9 pages).

Interview Summary Dated Mar. 25, 2025 from the US Patent and Trademark Office Re. U.S. Appl. No. 17/428,706. (10 pages).

Official Action Dated Mar. 20, 2025 from the US Patent and Trademark Office Re. U.S. Appl. No. 17/504,598. (54 Pages).

Official Action Dated Apr. 22, 2025 from the US Patent and Trademark Office Re. U.S. Appl. No. 18/379,189. (158 Pages).

Official Action Dated Mar. 26, 2025 from the US Patent and Trademark Office Re. U.S. Appl. No. 17/684,452. (370 pages).

Requisition by the Examiner Dated Apr. 3, 2025 From the Innovation, Science and Economic Development Canada, Canadian Intellectual Property Office Re. Application No. 3,219,298. (3 Pages).

Requisition by the Examiner Dated May 12, 2025 From the Innovation, Science and Economic Development Canada, Canadian Intellectual Property Office Re. Application No. 2,953,073. (4 pages).

MatWeb "Alumina Material Properties—99.5% Alumina, porous body", MatWeb Material Property Data, downloaded fron the internet: https://www.matweb.com/search/DataSheet.aspx?MatGUID=1bf6c5b8daed427693211c5f985b90a2&ckck=1, 2 pages, 1994.

Official Action Dated Aug. 6, 2025 from the US Patent and Trademark Office Re. U.S. Appl. No. 17/428,706. (59 pages).

Communication Pursuant to Article 94(3) EPC Dated Jul. 24, 2025 From the European Patent Office Re. Application No. 19754583.3. (5 Pages).

Interview Summary Dated Jul. 29, 2025 from the US Patent and Trademark Office Re. U.S. Appl. No. 18/379,189. (9 pages).

Advisory Action Before the Filing of an Appeal Brief Dated Dec. 16, 2025 from US Patent and Trademark Office Re. U.S. Appl. No. 17/684,452. (5 pages).

Communication Pursuant to Article 94(3) EPC Dated Feb. 2, 2026 From the European Patent Office Re. Application No. 20150198.8 (7 Pages).

Office Action Dated Nov. 17, 2025 From the Israel Patent Office Re. Application No. 294075. (3 Pages).

Office Action Dated Nov. 25, 2025 From the Israel Patent Office Re. Application No. 294076. (3 Pages).

Office Action Dated Nov. 26, 2025 From the Israel Patent Office Re. Application No. 294077. (3 Pages).

Official Action Dated Jan. 15, 2026 from the US Patent and Trademark Office Re. U.S. Appl. No. 18/234,882. (209 pages).

(56) References Cited

OTHER PUBLICATIONS

Requisition by the Examiner Dated Dec. 9, 2025 From the Innovation, Science and Economic Development Canada, Canadian Intellectual Property Office Re. Application No. 3,114,582. (3 Pages).

Requisition by the Examiner Dated Nov. 21, 2025 From the Innovation, Science and Economic Development Canada, Canadian Intellectual Property Office Re. Application No. 3,009,599. (3 Pages).

Third-Party Submission Under 37 CFR 1.290 Dated Nov. 14, 2025 From the US Patent and Trademark Office Re. U.S. Appl. No. 19/014,337. (4 Pages).

Lemos de Arruda Camargo "Os Poderes das Plantas Sagradas Numa Abordagem Etnofarmacobotanica [The Powers of Sacred Plants: An Ethnopharmacobotanical Approach]", Revista do Museu de Arqueologia e Etnologia, 15-16: 395-410, Dec. 14, 2006 and Its Translation Into English.

Schultes et al. "Plants of the Gods: Their Sacred, Healing, and Hallucinogenic Powers", Healing Arts Press, p. 35, 49, 116-119, 138, 176-181, 2001.

Communication Pursuant to Article 94(3) EPC Dated Oct. 20, 2025 From the European Patent Office Re. Application No. 21199976.8 (5 Pages).

Examination Report Dated Sep. 28, 2025 From the Australian Government, IP Australia Re. Application No. 2024202785. (9 Pages).

Examination Report Dated Oct. 30, 2025 From the Australian Government, IP Australia Re. Application No. 2024227181. (8 Pages).

Notice of Allowance Dated Sep. 11, 2025 together with Interview Summary From the US Patent and Trademark Office Re. U.S. Appl. No. 17/504,598. (21 pages).

Notice of Allowance Dated Sep. 23, 2025 from the US Patent and Trademark Office Re. U.S. Appl. No. 18/379,189. (34 pages).

Notice of Reason(s) for Rejection Dated Sep. 16, 2025 From the Japan Patent Office Re. Application No. 2023-061198 and Its Translation Into English. (4 Pages).

Official Action Dated Sep. 5, 2025 from the US Patent and Trademark Office Re. U.S. Appl. No. 16/969,612. (93 Pages).

Official Action Dated Sep. 16, 2025 from the US Patent and Trademark Office Re. U.S. Appl. No. 17/684,452. (38 pages).

Request for Examination and Search Report Dated Aug. 13, 2025 From the (Rospatent), Federal Government Institution of Industrial Property of the Federal Service of Intellectual Property, Patents and Trademark of the Russian Federation Re. Application No. 2025109544 and Its Translation Into English. (17 Pages).

Examination Report Dated May 29, 2022 From the Servico Publico Federal, Ministerio da Economia, Instituto Nacional da Propriedade Industrial do Brasil RE Application No. BR12 2020 018207 5 with Pending Claims and its English Summary. (8 Pages).

Examination Report Dated May 6, 2024 From the Australian Government, IP Australia Re. Application No. 2022211900. (4 Pages).

Notice of Reason(s) for Rejection Dated Jun. 4, 2024 From the Japan Patent Office Re. Application No. 2023-139046 and Its Translation Into English. (6 Pages).

Examination Report Dated Jan. 11, 2023 From the Australian Government, IP Australia Re. Application No. 2021204365. (4 Pages).

Examination Report Dated Apr. 20, 2021 From the Instituto Mexicano de la Propiedad Industrial, Direccion Divisional de Patentes Re. Application No. MX/a/2017/000057 together with an English Summary. (5 Pages).

Examination Report Dated Sep. 9, 2024 From the Australian Government, IP Australia Re. Application No. 2022211900. (5 Pages).

Examination Report Dated Aug. 6, 2021 From the Instituto Mexicano de la Propiedad Industrial, Direccion Divisional de Patentes Re. Application No. MX/a/2017/000057 and Its Translation Into English. (10 Pages).

Examination Report Dated Dec. 21, 2023 From the Australian Government, IP Australia Re. Application No. 2022256225. (5 Pages).

Examination Report Dated Jan. 29, 2022 from the Australian Patent Office Re. Application No. 2021202185. (5 pages).

Examination Report Dated Aug. 31, 2023 From the Australian Government, IP Australia Re. Application No. 2021204365. (4 Pages).

Translation Dated Sep. 26, 2023 of Grounds of Reason of Rejection Dated Sep. 14, 2023 From the Korean Intellectual Property Office Re. Application No. 10-2023-7025097. (5 Pages).

Examination Report Dated Jul. 24, 2024 From the Australian Government, IP Australia Re. Application No. 2019221321. (3 Pages).

Official Action Dated Jul. 24, 2024 from the US Patent and Trademark Office Re. U.S. Appl. No. 17/504,598. (285 pages).

Examination Report Dated Jun. 6, 2024 From the Australian Government, IP Australia Re. Application No. 2022256225. (4 Pages).

Notice of Reason(s) for Rejection Dated May 21, 2024 From the Japan Patent Office Re. Application No. 2023-061198 and Its Translation Into English. (7 Pages).

Official Action Dated Jun. 11, 2024 from the US Patent and Trademark Office Re. U.S. Appl. No. 17/428,706. (279 pages).

Official Action Dated Jun. 14, 2024 from the US Patent and Trademark Office Re. U.S. Appl. No. 16/969,612. (78 pages).

Examination Report Dated Nov. 8, 2024 From the Australian Government, IP Australia Re. Application No. 2022256225. (5 Pages).

Examination Report Dated Oct. 19, 2023 From the Australian Government, IP Australia Re. Application No. 2022211900. (8 Pages).

Requisition by the Examiner Dated Jun. 10, 2025 From the Innovation, Science and Economic Development Canada, Canadian Intellectual Property Office Re. Application No. 3,127,552. (6 Pages).

Requisition by the Examiner Dated Jun. 12, 2025 From the Innovation, Science and Economic Development Canada, Canadian Intellectual Property Office Re. Application No. 3,090,359. (5 Pages).

Requisition by the Examiner Dated Aug. 17, 2023 From the Innovation, Science and Economic Development Canada, Canadian Intellectual Property Office Re. Application No. 3,009,599. (3 Pages).

Requisition by the Examiner Dated May 25, 2022 From the Innovation, Science and Economic Development Canada, Canadian Intellectual Property Office Re. Application No. 3,114,582. (3 Pages).

Requisition by the Examiner Dated Sep. 28, 2021 From the Innovation, Science and Economic Development Canada, Canadian Intellectual Property Office Re. Application No. 2,953,069. (4 Pages).

Requisition by the Examiner Dated Dec. 22, 2022 From the Innovation, Science and Economic Development Canada, Canadian Intellectual Property Office Re. Application No. 3,009,599.(10 pages).

Requisition by the Examiner Dated Apr. 4, 2022 From the Innovation, Science and Economic Development Canada, Canadian Intellectual Property Office Re. Application No. 2,953,074 with Claims. (11 Pages).

Requisition by the Examiner Dated Dec. 13, 2022 From the Innovation, Science and Economic Development Canada, Canadian Intellectual Property Office Re. Application No. 2,953,074 with claims. (11 pages).

Requisition by the Examiner Dated Sep. 28, 2021 From the Innovation, Science and Economic Development Canada, Canadian Intellectual Property Office Re. Application No. 2,953,073. (4 Pages).

Requisition by the Examiner Dated Mar. 11, 2022 From the Innovation, Science and Economic Development Canada, Canadian Intellectual Property Office Re. Application No. 2,953,082. (6 Pages).

(56) References Cited

OTHER PUBLICATIONS

Requisition by the Examiner Dated Jul. 5, 2023 From the Innovation, Science and Economic Development Canada, Canadian Intellectual Property Office Re. Application No. 2,953,073. (3 pages).
Requisition by the Examiner Dated Oct. 25, 2024 From the Innovation, Science and Economic Development Canada, Canadian Intellectual Property Office Re. Application No. 3,199,049. (5 Pages).
Requisition by the Examiner Dated Mar. 3, 2025 From the Innovation, Science and Economic Development Canada, Canadian Intellectual Property Office Re. Application No. 3,215,815. (5 Pages).
Requisition by the Examiner Dated Feb. 11, 2025 From the Innovation, Science and Economic Development Canada, Canadian Intellectual Property Office Re. Application No. 3,199,049. (3 Pages).
Notice of Allowance Dated Dec. 1, 2021 from the US Patent and Trademark Office Re. U.S. Appl. No. 16/030,967. (21 pages).
Patent Examination Report Dated Oct. 26, 2021 From the Australian Government, IP Australia Re. Application No. 2017204945. (3 Pages).
Notice of Reason(s) for Rejection Dated Nov. 7, 2023 From the Japan Patent Office Re. Application No. 2021-522537. (4 Pages).
Notice of Reason(s) for Rejection Dated May 16, 2023 From the Japan Patent Office Re. Application No. 2021-522537 and Its Translation Into English. (9 Pages).
Notice of Reasons for Rejection Dated May 24, 2022 From the Japan Patent Office Re. Application No. 2020-134166 and Its Translation Into English. (10 Pages).
Notice of Reason(s) for Rejection Dated Mar. 7, 2023 From the Japan Patent Office Re. Application No. 2021-175408 and Its Translation Into English. (5 Pages).
Notice of Reason(s) for Rejection Dated Jun. 13, 2023 From the Japan Patent Office Re. Application No. 2022-115378. (4 pages).
Notice of Reasons for Rejection Dated Feb. 22, 2022 From the Korean Intellectual Property Office Re. Application No. 10-2017-7002721 and Its Translation Into English. (5 Pages).
Notice of Allowance Dated Feb. 12, 2024 from the US Patent and Trademark Office Re. U.S. Appl. No. 17/679,190. (13 pages).
Notice of Reason(s) for Rejection Dated Jan. 30, 2024 From the Japan Patent Office Re. Application No. 2023-139046 and Its Translation Into English. (12 Pages).
Notice of Reason(s) for Rejection Dated Oct. 12, 2021 From the Japan Patent Office Re. Application No. 2020-101083 and Its Translation Into English. (17 Pages).
Notice of Reason(s) for Rejection Dated Oct. 12, 2021 From the Japan Patent Office Re. Application No. 2020-134166 and Its Translation Into English. (10 Pages).
Notice of Allowance Dated Jun. 28, 2023 Together with Interview Summary Dated Jun. 13, 2023 from the US Patent and Trademark Office Re. U.S. Appl. No. 16/068,373. (39 pages).
Requisition by the Examiner Dated Jun. 27, 2023 From the Innovation, Science and Economic Development Canada, Canadian Intellectual Property Office Re. Application No. 3,114,582. (3 pages).
Notice of Reasons for Rejection Dated Aug. 27, 2024 From the Japan Patent Office Re. Application No. 2023-061198 and Its Machine Translation Into English. (4 Pages).
Notice of Allowance Dated May 14, 2024 From the US Patent and Trademark Office Re. U.S. Appl. No. 17/694,764.(23 pages).
Notification of Office Action and Search Report Dated Oct. 16, 2023 From the National Intellectual Property Administration of the People's Republic of China Re. Application No. 202080027182.5 (5 Pages).
Notification of Office Action and Search Report Dated Oct. 25, 2022 From the State Intellectual Property Office of the People's Republic of China Re. Application No. 202110926270.5 and Its Translation of Office Action Into English. (7 Pages).
Official Action Dated Oct. 26, 2022 from the US Patent and Trademark Office Re. U.S. Appl. No. 17/238,278. (156 pages).

Grasscity "How to Make Hush?, Discussion in 'Apprentice Marijuana Consuption' started by Juggalobud", Grasscity Forums, Retrieved from the Internet, Nov. 1, 2002 (17 pages).
Unodc "Recommended Methods for the Identification and Analysis of Cannabis and Cannabis Products", United Nations Office on Drugs, Crime, United Nations Publications, 1-50, Sep. 2009.
Verilifc "Cannabis Trichomes: What Are They & What They Do?", Retrieved from the Internet, Nov. 29, 2021 (4 pages).
Notification of Office Action Dated Jun. 23, 2022 From the State Intellectual Property Office of the People's Republic of China Re. Application No. 20200101980.3. (8 Pages).
Notification of Office Action and Search Report Dated Jun. 27, 2022 From the State Intellectual Property Office of the People's Republic of China Re. Application No. 201980081175.0. (13 Pages).
Official Action Dated Jul. 6, 2022 from US Patent and Trademark Office Re. U.S. Appl. No. 16/068,373. (40 pages).
Applicant-Initiated Interview Summary Dated Apr. 5, 2018 From the US Patent and Trademark Office Re. U.S. Appl. No. 15/391,896. (3 pages).
Applicant-Initiated Interview Summary Dated Jan. 5, 2018 From the US Patent and Trademark Office Re. U.S. Appl. No. 15/382,819. (3 pages).
Applicant-Initiated Interview Summary Dated Dec. 22, 2017 From the US Patent and Trademark Office Re. U.S. Appl. No. 15/312,647. (3 pages).
Applicant-Initiated Interview Summary Dated Dec. 22, 2017 From the US Patent and Trademark Office Re. U.S. Appl. No. 15/362,883. (3 pages).
Applicant-Initiated Interview Summary Dated Mar. 22, 2018 From the US Patent and Trademark Office Re. U.S. Appl. No. 15/308,370. (5 pages).
Applicant-Initiated Interview Summary Dated May 22, 2017 From the US Patent and Trademark Office Re. U.S. Appl. No. 15/386,182. (3 pages).
Applicant-Initiated Interview Summary Dated May 23, 2017 From the US Patent and Trademark Office Re. U.S. Appl. No. 15/362,841. (3 pages).
Applicant-Initiated Interview Summary Dated May 23, 2017 From the US Patent and Trademark Office Re. U.S. Appl. No. 15/362,883. (3pages).
Applicant-Initiated Interview Summary Dated May 23, 2017 From the US Patent and Trademark Office Re. U.S. Appl. No. 15/375,098. (3 pages).
Applicant-Initiated Interview Summary Dated May 23, 2017 From the US Patent and Trademark Office Re. U.S. Appl. No. 15/382,819. (3 pages).
Applicant-Initiated Interview Summary Dated Dec. 30, 2019 From the US Patent and Trademark Office Re. U.S. Appl. No. 15/690,323. (4 pages).
Communication Pursuant to Article 94(3) EPC Dated Sep. 2, 2020 From the European Patent Office Re. Application No. 15756490.7. (5 Pages).
Communication Pursuant to Article 94(3) EPC Dated Aug. 4, 2020 From the European Patent Office Re. Application No. 15815982.2. (5 Pages).
Communication Pursuant to Article 94(3) EPC Dated Sep. 5, 2018 From the European Patent Office Re. Application No. 15744363.1. (4 Pages).
Communication Pursuant to Article 94(3) EPC Dated Feb. 6, 2019 From the European Patent Office Re. Application No. 15753782.0. (6 Pages).
Communication Pursuant to Article 94(3) EPC Dated Nov. 12, 2018 From the European Patent Office Re. Application No. 15814472.5. (5 Pages).
Communication Pursuant to Article 94(3) EPC Dated Nov. 12, 2018 From the European Patent Office Re. Application No. 15815982.2. (4 Pages).
Communication Pursuant to Article 94(3) EPC Dated Jan. 19, 2018 From the European Patent Office Re. Application No. 15744363.1. (4 Pages).
Communication Pursuant to Article 94(3) EPC Dated Nov. 19, 2018 From the European Patent Office Re. Application No. 15756490.7. (4 Pages).

(56) References Cited

OTHER PUBLICATIONS

Communication Pursuant to Article 94(3) EPC Dated Jan. 22, 2018 From the European Patent Office Re. Application No. 15756490.7. (4 Pages).

Communication Pursuant to Article 94(3) EPC Dated Jun. 23, 2017 From the European Patent Office Re. Application No. 11815728.8. (5 Pages).

Communication Pursuant to Article 94(3) EPC Dated Apr. 26, 2018 From the European Patent Office Re. Application No. 11815728.8. (4 Pages).

Communication Pursuant to Article 94(3) EPC Dated Feb. 26, 2018 From the European Patent Office Re. Application No. 15753782.0. (6 Pages).

Communication Relating to the Results of the Partial International Search Dated May 18, 2012 From the International Searching Authority Re. Application No. PCT/IL2011/050071.

Communication Relating to the Results of the Partial International Search Dated Oct. 22, 2015 From the International Searching Authority Re. Application No. PCT/IL2015/050673.

Communication Relating to the Results of the Partial International Search Dated Sep. 24, 2015 From the International Searching Authority Re. Application No. PCT/IL2015/050677.

Decision of Rejection Dated Sep. 17, 2019 From the Japan Patent Office Re. Application No. 2016-576068 and Its Translation Into English. (12 Pages).

Decision of Rejection Dated Aug. 27, 2019 From the Japan Patent Office Re. Application No. 2016-576071 and Its Translation Into English. (8 Pages).

Decision to Grant a Patent for Invention and Search Report Dated Oct. 29, 2019 From the (Rospatent), Federal Government Institution of Industrial Property of the Federal Service of Intellectual Property, Patents and Trademark of the Russian Federation Re. Application No. 2019115942.and Its Translation Into English. (16 Pages).

Decision to Grant a Patent for Invention Dated Mar. 25, 2019 From the Federal Goverment Institution, Federal Institute of Industrial Property of the Federal Service for Intellectual Property, Patents and Trademarks, Rospatent of the Russian Federation Re. Application No. 2017102236 and Its Translation Into English. (18 Pages).

Decision to Grant a Patent for Invention Dated Mar. 25, 2019 From the Federal Government Institution, Federal Institute of Industrial Property of the Federal Service for Intellectual Property, Patents and Trademarks, Rospatent of the Russian Federation Re. Application No. 2017102235 and Its Translation Into English. (16 Pages).

Decision to Grant a Patent for Invention Dated Mar. 25, 2019 From the Federal Government Institution, Federal Institute of Industrial Property of the Federal Service of Intellectual Property, Patents and Trademarks, Rospatent of the Russian Federation Re. Application No. 2017102233 and Its Translation Into English. (17 Pages).

European Search Report and the European Search Opinion Dated Jul. 5, 2019 From the European Patent Office Re. Application No. PCT/19165448.2. (7 Pages).

European Search Report and the European Search Opinion Dated Apr. 8, 2021 From the European Patent Office Re. Application No. 21159548.3. (7 Pages).

European Search Report and the European Search Opinion Dated Nov. 20, 2020 From the European Patent Office Re. Application No. 20192870.2. (7 Pages).

European Search Report and the European Search Opinion Dated Apr. 22, 2021 From the European Patent Office Re. Application No. 20192870.2. (14 Pages).

European Search Report and the European Search Opinion Dated Mar. 26, 2020 From the European Patent Office Re. Application No. 20150198.8. (9 Pages).

Examination Report Dated Feb. 5, 2020 From the Instituti Mexicano de la Propiedad Industrial, IMPI, Direccion Divisional de Patentes Re. Application No. MX/a/2017/000056 and Its Translation Into English. (4 Pages).

Examination Report Dated Apr. 8, 2019 From the Australian Government, IP Australia Re. Application No. 2015283589. (5 Pages).

Examination Report Dated Jan. 13, 2021 From the Instituto Mexicano de la Propiedad Industrial, Secretario de Economia, Dioreccion Divisional de Patentes Re. Application No. MX/a/2017/000057. (6 Pages).

Examination Report Dated Sep. 14, 2020 From the Australian Government, IP Australia Re. Application No. 2019229369. (4 Pages).

Examination Report Dated Jan. 15, 2019 From the Australian Government, IP Australia Re. Application No. 2015283594. (4 Pages).

Examination Report Dated Feb. 20, 2020 From the Australian Government, IP Australia Re. Application No. 2015283590. (6 Pages).

Examination Report Dated Jan. 21, 2019 From the Australian Government, IP Australia Re. Application No. 2015283593. (4 Pages).

Examination Report Dated Mar. 29, 2019 From the Australian Government, IP Australia Re. Application No. 2015283590. (5 Pages).

Examination Report Dated Jan. 30, 2020 From the Instituto Mexicano de la Propiedade Industrial, IMPI, Direccion Divisional de Patentes Re. Application No. MX/a/2017/000055 and Its Translation Into English. (5 Pages).

Examiner-Initiated Interview Summary Dated Nov. 2, 2017 From the US Patent and Trademark Office Re. U.S. Appl. No. 15/382,819. (2 pages).

Final Official Action Dated Feb. 22, 2021 From the US Patent and Trademark Office Re. U.S. Appl. No. 16/131,079. (60 Pages).

Final Official Action Dated May 4, 2020 from the US Patent and Trademark Office Re. U.S. Appl. No. 15/690,323. (55 pages).

International Preliminary Report on Patentability Dated Jul. 2, 2013 From the International Preliminary Examining Authority Re. Application No. PCT/IL2011/050071.

International Preliminary Report on Patentability Dated Jan. 12, 2017 From the International Bureau of WIPO Re. Application No. PCT/IL2015/050673. (15 Pages).

International Preliminary Report on Patentability Dated Jan. 12, 2017 From the International Bureau of WIPO Re. Application No. PCT/IL2015/050674. (11 Pages).

International Preliminary Report on Patentability Dated Jan. 12, 2017 From the International Bureau of WIPO Re. Application No. PCT/IL2015/050675. (8 Pages).

International Preliminary Report on Patentability Dated Jan. 12, 2017 From the International Bureau of WIPO Re. Application No. PCT/IL2015/050677. (13 Pages).

International Preliminary Report on Patentability Dated Jan. 12, 2017 From the International Bureau of WIPO Re. Application No. PCT/IL2015/050678. (12 Pages).

International Preliminary Report on Patentability Dated Jan. 12, 2017 From the International Bureau of WIPO Re. Application No. PCT/IL2015/50676. (11 Pages).

International Preliminary Report on Patentability Dated Jul. 19, 2018 From the International Bureau of WIPO Re. Application No. PCT/IL2017/050014. (10 Pages).

International Preliminary Report on Patentability Dated Aug. 27, 2020 From the International Bureau of WIPO Re. Application No. PCT/IL2019/050178. (8 Pages).

International Search Report and the Written Opinion Dated Feb. 2, 2016 From the International Searching Authority Re. Application No. PCT/IL2015/050673.

International Search Report and the Written Opinion Dated Dec. 3, 2015 From the International Searching Authority Re. Application No. PCT/IL2015/050677.

International Search Report and the Written Opinion Dated May 3, 2020 From the International Searching Authority Re. Application No. PCT/IL2020/050151. (18 Pages).

International Search Report and the Written Opinion Dated Jan. 7, 2016 From the International Searching Authority Re. Application No. PCT/IL2015/050675.

International Search Report and the Written Opinion Dated Dec. 10, 2015 From the International Searching Authority Re. Application No. PCT/IL2015/050674.

(56)    References Cited

OTHER PUBLICATIONS

International Search Report and the Written Opinion Dated Oct. 19, 2012 From the International Searching Authority Re. Application No. PCT/IL2011/050071.

International Search Report and the Written Opinion Dated Jan. 20, 2016 From the International Searching Authority Re. Application No. PCT/IL2015/50676.

International Search Report and the Written Opinion Dated Oct. 22, 2015 From the International Searching Authority Re. Application No. PCT/IL2015/050678.

International Search Report and the Written Opinion Dated May 23, 2019 From the International Searching Authority Re. Application No. PCT/IL2019/050178. (15 Pages).

International Search Report and the Written Opinion Dated Mar. 27, 2017 From the International Searching Authority Re. Application No. PCT/IL2017/050014. (16 Pages).

International Search Report and the Written Opinion Dated Dec. 31, 2019 From the International Searching Authority Re. Application No. PCT/IL2019/051163. (16 Pages).

Interview Summary Dated Feb. 23, 2021 From the US Patent and Trademark Office Re. U.S. Appl. No. 16/068,373. (3 Pages).

Notice of Acceptance Dated Aug. 28, 2019 From the Australian Government, IP Australia Re. Application No. 2015283589. (4 Pages).

Notice of Allowance Dated Jun. 1, 2017 From the US Patent and Trademark Office Re. U.S. Appl. No. 13/997,302. (24 Pages).

Notice of Allowance Dated Mar. 1, 2018 From the US Patent and Trademark Office Re. U.S. Appl. No. 15/312,647. (24 pages).

Notice of Allowance Dated Jun. 12, 2018 From the US Patent and Trademark Office Re. U.S. Appl. No. 15/308,370. (13 pages).

Notice of Allowance Dated Apr. 19, 2018 From the US Patent and Trademark Office Re. U.S. Appl. No. 15/375,098. (5 pages).

Notice of Allowance Dated Sep. 20, 2017 From the US Patent and Trademark Office Re. U.S. Appl. No. 15/362,841. (33 pages).

Notice of Allowance Dated Sep. 20, 2017 From the US Patent and Trademark Office Rc. U.S. Appl. No. 15/386,182.(32 pages).

Notice of Allowance Dated Feb. 22, 2021 From the US Patent and Trademark Office Re. U.S. Appl. No. 15/690,323. (28 Pages).

Notice of Allowance Dated Apr. 23, 2018 From the US Patent and Trademark Office Re. U.S. Appl. No. 15/382,819. (17 pages).

Notice of Allowance Dated Oct. 23, 2018 From the US Patent and Trademark Office Re. U.S. Appl. No. 15/391,896. (16 pages).

Notice of Reason(s) for Rejection Dated Jan. 26, 2021 From the Japan Patent Office Re. Application No. 2019-231996 and Its Translation Into English.(10 Pages).

Notice of Reason(s) for Rejection Dated Jan. 26, 2021 From the Japan Patent Office Re. Application No. 2020-003761 and Its Translation Into English. (7 Pages).

Notice of Reasons for Rejection Dated Feb. 4, 2020 From the Japan Patent Office Re. Application No. 2016-576066 and Its Translation Into English. (6 Pages).

Notice of Reasons for Rejection Dated Jan. 7, 2020 From the Japan Patent Office Re. Application No. 2016-576067 and Its Translation Into English. (10 Pages).

Notice of Reasons for Rejection Dated May 7, 2019 From the Japan Patent Office Re. Application No. 2016-576067 and Its Translation Into English. (3 Pages).

Notice of Reasons for Rejection Dated May 7, 2019 From the Japan Patent Office Re. Application No. 2016-576068 and Its Translation Into English. (15 Pages).

Notice of Reasons for Rejection Dated May 7, 2019 From the Japan Patent Office Re. Application No. 2016-576071 and Its Translation Into English. (8 Pages).

Notice of Reasons for Rejection Dated Mar. 9, 2021 From the Japan Patent Office Re. Application No. 2016-576068 and Its Translation Into English. (17 Pages).

Notice of Reasons for Rejection Dated May 21, 2019 From the Japan Patent Office Re. Application No. 2016-576066 and Its Translation Into English. (12 Pages).

Notification of Office Action and Search Report Dated Mar. 1, 2021 From the State Intellectual Property Office of the People's Republic of China Re. Application No. 201580045151.1 and Its Translation of Office Action Into English. (8 Pages).

Notification of Office Action and Search Report Dated Feb. 3, 2020 From the State Intellectual Property Office of the People's Republic of China Re. Application No. 201580045151.1. 4 Pages).

Notification of Office Action and Search Report Dated Sep. 3, 2019 From the State Intellectual Property Office of the People's Republic of China Re. Application No. 201580045136.7. (9 Pages).

Notification of Office Action and Search Report Dated Sep. 3, 2019 From the State Intellectual Property Office of the People's Republic of China Re. Application No. 201580045638.X. (15 Pages).

Notification of Office Action and Search Report Dated Sep. 4, 2019 From the State Intellectual Property Office of the People's Republic of China Re. Application No. 201580046016.9 and Its Translation Into English. (16 Pages).

Notification of Office Action and Search Report Dated Aug. 13, 2020 From the State Intellectual Property Office of the People's Republic of China Re. Application No. 201580045151.1 and Its Translation of Office Action Into English. (9 Pages).

Notification of Office Action and Search Report Dated Dec. 30, 2019 From the China National Intellectual Property Administration Re. Application No. 201580045638.X. (11 Pages).

Notification of Office Action Dated Aug. 1, 2019 From the State Intellectual Property Office of the People's Republic of China Re. Application No. 201580045151.1 and Its Translation Into English. (8 Pages).

Notification of Office Action Dated Aug. 2, 2018 From the State Intellectual Property Office of the People's Republic of China Re. Application No. 201580045151.1 and Its Summary in English. (6 Pages).

Notification of Office Action Dated Feb. 3, 2019 From the State Intellectual Property Office of the People's Republic of China Re. Application No. 201580045136.7 and Its Translation Into English. (4 Pages).

Notification of Office Action Dated Jan. 3, 2020 From the China National Intellectual Property Administration Re. Application No. 201580046016.9 and Its Translation Into English. (13 Pages).

Notification of Office Action Dated Feb. 11, 2019 From the State Intellectual Property Office of the People's Republic of China Re. Application No. 201580045638.X and Its Translation Into English. (4 Pages).

Notification of Office Action Dated Feb. 11, 2019 From the State Intellectual Property Office of the People's Republic of China Re. Application No. 201580046016.9 and Its Translation Into English. (4 Pages).

Notification of Office Action Dated Dec. 27, 2019 From the State Intellectual Property Office of the People's Republic of China Re. Application No. 201580045136.7 and Its Translation Into English. (4 Pages).

Notification of Office Action Dated Feb. 27, 2019 From the State Intellectual Property Office of the People's Republic of China Re. Application No. 201580045151.1 and Its Translation into English. (6 Pages).

Office Action Dated Apr. 15, 2019 From the Israel Patent Office Re. Application No. 249834 and Its Translation Into English. (5 Pages).

Office Action Dated Apr. 15, 2019 From the Israel Patent Office Re. Application No. 249835 and Its Translation Into English. (5 Pages).

Office Action Dated Jan. 17, 2019 From the Israel Patent Office Re. Application No. 260852 and Its Translation Into English. (6 Pages).

Office Action Dated Jan. 19, 2017 From the Israel Patent Office Re. Application No. 227102 and Its Translation Into English. (5 Pages).

Office Action Dated Dec. 21, 2017 From the Israel Patent Office Re. Application No. 227102 and Its Translation Into English. (4 Pages).

Office Action Dated Jun. 22, 2016 From the Israel Patent Office Re. Application No. 227102 and Its Translation Into English.

Office Action Dated Jan. 30, 2020 From the Israel Patent Office Re. Application No. 249836 and Its Translation Into English. (9 Pages).

Official Action Dated Jun. 1, 2017 From the US Patent and Trademark Office Re. U.S. Appl. No. 15/375,098. (42 pages).

Official Action Dated Nov. 1, 2017 From the US Patent and Trademark Office Re. U.S. Appl. No. 15/382,819. (45 pages).

(56)                    References Cited

OTHER PUBLICATIONS

Official Action Dated Feb. 4, 2019 From the US Patent and Trademark Office Re. U.S. Appl. No. 15/362,883. (53 pages).
Official Action Dated Apr. 6, 2017 From the US Patent and Trademark Office Re. U.S. Appl. No. 15/362,841. (35 pages).
Official Action Dated Mar. 9, 2017 From the US Patent and Trademark Office Re. U.S. Appl. No. 15/386,182. (24 pages).
Official Action Dated Sep. 1, 2020 from the US Patent and Trademark Office Re. U.S. Appl. No. 15/690,323. (14 pages).
Official Action Dated Apr. 10, 2017 From the US Patent and Trademark Office Re. U.S. Appl. No. 15/362,883. (33 pages).
Official Action Dated Dec. 12, 2017 From the US Patent and Trademark Office Re. U.S. Appl. No. 15/308,370. (27 pages).
Official Action Dated Mar. 13, 2017 From the US Patent and Trademark Office Re. U.S. Appl. No. 15/391,896. (22 pages).
Official Action Dated Mar. 14, 2018 From the US Patent and Trademark Office Re. U.S. Appl. No. 15/362,883. (21 pages).
Official Action Dated Aug. 18, 2017 From the US Patent and Trademark Office Re. U.S. Appl. No. 15/308,370. (56 pages).
Official Action Dated Apr. 20, 2017 From the US Patent and Trademark Office Re. U.S. Appl. No. 15/382,819. (30 pages).
Official Action Dated Sep. 22, 2017 From the US Patent and Trademark Office Re. U.S. Appl. No. 15/362,883. (43 pages).
Official Action Dated Jan. 25, 2018 From the US Patent and Trademark Office Re. U.S. Appl. No. 15/375,098. (37 pages).
Official Action Dated Dec. 26, 2017 From the US Patent and Trademark Office Re. U.S. Appl. No. 15/391,896. (53 pages).
Official Action Dated Jul. 28, 2020 from the US Patent and Trademark Office Re. U.S. Appl. No. 16/131,079. (102 pages).
Official Action Dated Sep. 28, 2017 From the US Patent and Trademark Office Re. U.S. Appl. No. 15/312,647. (57 pages).
Official Action Dated Jan. 30, 2017 From the US Patent and Trademark Office Re. U.S. Appl. No. 13/997,302. (23 pages).
Official Action Dated Sep. 30, 2016 From the US Patent and Trademark Office Re. U.S. Appl. No. 13/997,302.
Official Action Dated Sep. 30, 2019 From the US Patent and Trademark Office Re. U.S. Appl. No. 15/690,323. (123 pages).
Official Action Dated May 31, 2018 From the US Patent and Trademark Office Re. U.S. Appl. No. 15/391,896. (17 pages).
Official Action Dated Jan. 8, 2021 from the US Patent and Trademark Office Re. U.S. Appl. No. 16/068,373. (85 pages).
Patent Examination Report Dated Sep. 14, 2020 From the Australian Government, IP Australia Re. Application No. 2019275594. (4 Pages).
Patent Examination Report Dated Nov. 23, 2020 From the Australian Government, IP Australia Re. Application No. 2019229370. (4 Pages).
Pre-Appeal Examination Report Dated Feb. 6, 2020 From the Japan Patent Office Re. Application No. 2016-576068 and Its Translation Into English.
Request for Examination and Search Report Dated Feb. 4, 2021 From the Federal Government Institution, Federal Institute of Industrial Property of the Federal Service of Intellectual Property, Patents and Trademarks of the Russian Federation, FIPS Re. Application No. 2020130235 and Its Translation of Office Action Into English. (9 Pages).
Request for Examination and Search Report Dated Nov. 22, 2018 From the Federal Government Institution, Federal Institute of Industrial Property of the Federal Service for Intellectual Property, Patents and Trademarks of the Russian Federation Re. Application No. 2017102236 and Its Translation of Office Action Into English. (7 Pages).
Request for Examination and Search Report Dated Nov. 23, 2018 From the Federal Government Institution, Federal Institute of Industrial Property of the Federal Service for Intellectual Property, Patents and Trademarks of the Russian Federation Re. Application No. 2017102235 and Its Translation Into English. (9 Pages).
Request for Examination and Search Report Dated Feb. 26, 2020 From the Federal Government Institution, Federal Institute of Industrial Property of the Federal Service of Intellectual Property, Patents and Trademarks of the Russian Federation, FIPS Re. Application No. 2019115949 and Its Translation Into English. (11 Pages).
Request for Examination and Search Report Dated Nov. 27, 2018 From the Federal Government Institution, Federal Institute of Industrial Property of the Federal Service of Intellectual Property, Patents and Trademarks of the Russian Federation Re. Application No. 2017102233 and Its Translation of Office Action Into English. (8 Pages).
Request for Examination Dated Feb. 4, 2021 From the (Rospatent), Federal Government Institution of Industrial Property of the Federal Service of Intellectual Property, Patents and Trademark of the Russian Federation Re. Application No. 2020130235. (5 Pages).
Request for Examination Dated Dec. 12, 2018 From the Federal Government Institution, Federal Institute of Industrial Property of the Federal Service or Intellectual Property, Patents and Trademark of the Russian Federation Re. Application No. 2017102234 and its Translation Into English. (9 Pages).
Request for Examination Dated Jan. 28, 2020 From the Federal Government Institution, Federal Institute of Industrial Property of the Federal Service or Intellectual Property, Patents and Trademark of the Russian Federation Re. Application No. 2017102234 and Its Translation Into English. (14 Pages).
Requisition by the Examiner Dated Nov. 2, 2018 From the Innovation, Science and Economic Development Canada, Canadian Intellectual Property Office Re. Application No. 2,822,738. (4 Pages).
Requisition by the Examiner Dated Aug. 6, 2019 From the Innovation, Science and Economic Development Canada, Canadian Intellectual Property Office Re. Application No. 2,822,738.(4 Pages).
Requisition by the Examiner Dated Aug. 13, 2020 From the Innovation, Science and Economic Development Canada, Canadian Intellectual Property Office Re. Application No. 2,822,738. (3 Pages).
Requisition by the Examiner Dated Nov. 16, 2017 From the Innovation, Science and Economic Development Canada, Canadian Intellectual Property Office Re. Application No. 2,822,738. (4 Pages).
Restriction Official Action Dated Aug. 7, 2017 From the US Patent and Trademark Office Re. U.S. Appl. No. 15/312,647. (8 pages).
Restriction Official Action Dated Jul. 8, 2016 From the US Patent and Trademark Office Re. U.S. Appl. No. 13/997,302.
Restriction Official Action Dated Sep. 17, 2020 from the US Patent and Trademark Office Re. U.S. Appl. No. 16/068,373. (8 pages).
Search Report and Explanation Dated Mar. 24, 2020 From the Servico Publico Federal, Ministerio da Economia, Instituto Nacional da Propriedade Industrial do Brasil Re. Application No. BR112016030944-8 and Its Summary in English. (5 Pages).
Search Report and Explanation Dated Mar. 24, 2020 From the Servico Publico Federal, Ministerio da Economia, Instituto Nacional da Propriedade Industrial do Brasil Re. Application No. BR112016030952-9 and Its Summary in English. (5 Pages).
Search Report and Explanation Dated Mar. 24, 2020 From the Sevico Publico Federal, Ministerio da Economia, Instituto Nacional da Propriedade Industrial do Brasil Re. Application No. BR112016030955-3 and Its Summary in English. (5 Pages).
Search Report and Explanations Dated Apr. 15, 2020 From the Servico Publico Federal, Ministerio da Economia, Instituto Nacional da Propriedade Industrial do Brasil Re. Application No. BR112016030829-8 and Its Summary in English. (5 Pages).
Summons to Attend Oral Proceedings Pursuant to Rule 115(1) EPC Dated Sep. 24, 2020 From the European Patent Office Re. Application No. 15814472.5. (6 Pages).
Supplementary European Search Report and the European Search Opinion Dated Aug. 19, 2019 From the European Patent Office Re. Application No. 17735927.0. (8 Pages).
Supplementary European Search Report and the European Search Opinion Dated Mar. 19, 2018 From the European Patent Office Re. Application No. 15814472.5. (9 Pages).
Supplementary European Search Report and the European Search Opinion Dated Mar. 19, 2018 From the European Patent Office Re. Application No. 15815982.2. (8 Pages).

(56)　　　　　References Cited

OTHER PUBLICATIONS

Translation Dated Oct. 1, 2019 of Notification of Office Action Dated Sep. 3, 2019 From the State Intellectual Property Office of the People's Republic of China Re. Application No. 201580045638.X. (13 Pages).

Translation Dated Aug. 14, 2018 of Notification of Office Action Dated Aug. 2, 2018 From the State Intellectual Property Office of the People's Republic of China Re. Application No. 201580045151. 1. (3 Pages).

Translation Dated Sep. 18, 2019 of Notification of Office Action Dated Sep. 3, 2019 From the State Intellectual Property Office of the People's Republic of China Re. Application No. 201580045136.7. (5 Pages).

Translation Dated Feb. 20, 2020 of Notification of Office Action Dated Feb. 3, 2020 From the State Intellectual Property Office of the People's Republic of China Re. Application No. 201580045. (4 Pages).

Translation Dated Jan. 22, 2020 of Notification of Office Action Dated Dec. 30, 2019 From the China National Intellectual Property Administration Re. Application No. 201580045638.X. (9 Pages).

Written Opinion Dated Apr. 22, 2013 From the International Preliminary Examining Authority Re. Application No. PCT/IL2011/050071.

AAAAI "Inhaled Asthma Medications: Tips to Remember", American Academy of Allergy Asthma & Immunology, AAAAI, 4 P., 2013.

Abrams et al. "Vaporization as a Smokeless Cannabis Delivery System: A Pilot Study", Clinical Pharmacology & Therapeutics, 82(5): 572-578, Advance Online Publication Apr. 11, 2007.

Assaf et al. "Pre- and Post-Conditioning Treatment With An Ultra-Low Dose of [Delta]ˆsup9ˆ—Tetrahydrocannabinol (THC) Protects Against Pentylenetetrazole (PTZ)-Induced Cognitive Damage", Behavioral Brain Research, 220(1): 194-201, Jun. 2011.

Bhattacharyya et al. "Opposite Effects of Delta-9-Tetrahydrocannabinol and Cannabidiol on Human Brain Function and Psychopathology", Neuropsychopharmacology, 35: 764-774, 2010.

Boden et al. "The Effects of Cannabis Use Expectancies on Self-Initiated Cannabis Cessation", Addiction, 108: 1649-1657, 2013.

Carter et al. "Medicinal Cannabis: Rational Guidelines for Dosing", IDrugs, 7(5):464-470, May 2004.

Cohen et al. "Modelling of the Concentration—Effect Relationship of THC on Central Nervous System Parameters and Heart Rate—Insight Into Its Mechanisms of Action and a Tool for Clinical Research and Development of Cannabinoids", Journal of Pharmacology, 22(7): 717-726, Sep. 2008.

Das et al. "Effects of 9-Ene-Tetrahydrocannabinol on Expression of Beta-Type Transforming Growth Factors, Insulin-Like Growth Factor-I and C-Myc Genes in the Mouse Uterus", The Journal of Steroid Biochemistry and Molecular Biology, 45(6): 459-465, 1993.

Eisenberg et al. "The Pharmacokinetics, Efficacy, Safety, and Ease of Use of a Novel Portable Metered-Dose Cannabis Inhaler in Patients With Chronic Neuropathic Pain: A Phase 1a Study", Journal of Pain & Palliative Care Pharmacotherapy, 28(3): 216-225, Published Online Aug. 13, 2014.

Farrimond et al. "Cannabinol and Cannabidiol Exert Opposing Effects on Rat Feeding Patterns", Psychopharmacology, 223: 117-129, 2012.

FDA "Guidance for Industry. Population Pharmacokinetics", U.S. Department of Health and Human Services, Food and Drug Administration (FDA), Center for Drug Evaluation and Research (CDER), Center for Biological Evaluation and Research (CBER), CP 1: 1-31, Feb. 1999.

Fishbein et al. "Long-Term Behavioral and Biochemical Effects of an Ultra-Low Dose of [Delta]ˆsup9ˆ-Tetrahydrocannabinol (THC): Neuroprotection and ERK Signaling", Experimental Brain Research, 221(4): 437-448, Published Online Jul. 22, 2012.

Green Machine "Structure of a leaf—Internal & External", Retrieved from google.com, 6 Pages, Sep. 2019.

Hazekamp et al. "Bedrocan®—Stimulating the Development of Herbal Cannabis—Based Products", Bedromedical Presentation, 2013.

Hazekamp et al. "Evaluation of a Vaporizing (Volcano®) for the Pulmonary Administration of Tetrahydrocannabinol", Journal of Pharmaceutical Sciences, 95(6): 1308-1317, Jun. 2006.

Hazekamp et al. "The Medicinal Use of Cannabis and Cannabinoids—An International Cross-Sectional Survey on Administration Forms", Journal of Psychoactive Drugs, 45(3): 199-210, 2013.

Herbalizer "Herbalizer, the New Vaporization Experience", 6 P., Jun. 7, 2013.

Ibrahim et al. "Inhalation Drug Delivery Devices: Technology Update", Medical Devices: Evidence and Research, 8: 131-139, Feb. 12, 2015.

Jamontt et al. "The Effects of Delta[9]-Tetrahydrocannabinol and Cannabidiol Alone and in Combination on Damage, Inflammation and in Vitro Motility Disturbances in Rat Colitis", British Journal of Pharmacology, 160: 712-723, 2010.

Jang et al. "Thermophysical Properties of Porous SiC Ceramics Fabricated by Pressureless Sintering", Science and Technology of Advanced Materials, 8(7): 655-659, Nov. 30, 2007.

Lanz et al. "Medicinal Cannabis: In Vitro Validation of Vaporizers for the Smoke-Free Inhalation of Cannabis", Plos One, 11(1): e0147286-1-e0147286-18, Jan. 19, 2016.

McPartland et al. "Affinity and Efficacy Studies of Tetrahydrocannabinolic Acid A at Cannabinoid Receptor Types One and Two", Cannabis and Cannabinoid Research, 2(1): 87-95, May 2017.

McPartland et al. "Are Cannabidiol and Delta9-Tetrahydrocannabivarin Negative Modulators of the Endocannabinoid System? A Systematic Review", British Journal of Pharmacology, 172(3): 737-753, Published Online Jan. 8, 2015.

McPartland et al. "Cannabis and Cannabis Extracts: Greater Than the Sum of Their Parts?", Journal of Cannabis Therapeutics, 1(3-4):103-132, Jun. 1, 2001.

Mechoulam et al. "Cannabidiol—Recent Advances", Chemistry & Biodiversity, 4:1678-1692, 2007.

Moreno-Sanz "Can You Pass the Acid Test? Critical Review and Novel Therapeutic Perspectives of Delta9-Tetrahydrocannabinolic Acid A", Cannabis and Cannabinoid Research, 1(1): 124-130, Published Online Jun. 1, 2016.

Norwood et al. "Best Practices for Extractables and Leachables in Orally Inhaled and Nasal Drug Products: An Overview of the PQRI Recommendations", Pharmaceutical Research, 25(4): 727-739, Published Online Jan. 9, 2008.

Ormrod et al. "A Survey of Weed Leaf Stomata and Trichomes", Canadian Journal of Plant Science, 48(2): 197-209, 1968.

Pertwee "The Diverse CB1 and CB2 Receptor Pharmacology of Three Plant Cannabinoids: Delta[9]-Tetrahydrocannabinol, Cannabidiol and Delta[9]-Tetrahydrocannabivarin", British Journal of Pharmacology, 153: 199-215, 2008.

Pomahacova et al. "Cannabis Smoke Condensate III: The Cannabinoid Content of Vaporised Cannabis Sativa", Inhalation Toxicology, 21(13): 1108-1112, Nov. 1, 2009.

Rabinowitz et al. "Fast Onset Medications Through Thermally Generated Aerosols", The Journal of Pharmacological and Experimental Therapeutics, 309(2): 769-775, Published Online Jan. 29, 2004.

Rau "The Inhalation of Drugs: Advantages and Problems", Respiratory Care, 50(3): 367-382, Mar. 2005.

Science "Nettle leaf trichromes", Retrieved from sciencesource. com, 1 Page, Sep. 2019.

Syqe Medical "The World's First Metered Dose Pharmaceutical Grade Medical Cannabis Inhaler", Syqe Medical™, Press Kit, p. 1-8, 2015.

Van Gerven "Biomarkers to Assess Adverse Drug Effects on the CNS", Centre for Human Drug Research, CHDR, Poster-Session, Slide-Show, 25 P., 2013.

Van Hell et al. "Evidence for Involvement of the Insula in the Psychotropic Effects of THC in Humans: A Double-Blind, Randomized Pharamcological MRI Study", International Journal of Neuropharmacology, 14: 1377-1388, 2011.

(56)　　　　　References Cited

OTHER PUBLICATIONS

Vann et al. "Divergent Effects of Cannabidiol on the Discriminative Stimulus and Place Conditioning Effects of Delta 9-Tetrahydrocannabiol", Drug and Alcohol Dependence, 94(1-3): 191-198, Apr. 1, 2008.

Vemuri et al. "Pharmacotherapeutic Targeting of the Endocannabinoid Signaling System: Drugs for Obesity and the Metabolic Syndrome", Physiology & Behavior, 93: 671-686, 2008.

Wallace et al. "Efficacy of Inhaled Cannabis on Painful Diabetic Neuropathy", The Journal of Pain, 169(7): 616-627, Published Online Apr. 3, 2015.

Ware et al. "Smoked Cannabis for Chronic Neuropathic Pain: A Randomized Controlled Trial", Canadian Medical Association Journal, CMAJ, 182(14): E694-E701, Published Online Aug. 30, 2010.

Wilsey et al. "A Randomized, Placebo-Controlled, Crossover Trial of Cannabis Cigarettes in Neuropathic Pain", The Journal of Pain, 9(6): 506-521, Published Online Apr. 10, 2008.

Wilsey et al. "Low-Dose Vaporized Cannabis Significantly Improves Neuropathic Pain", The Journal of Pain, 14(2): 136-148, Published Online Dec. 13, 2012. 'Discussion', Last Para.

Zuurman et al. "Biomarkers for the Effects of Cannabis and THC in Healthy Volunteers", British Journal of Clinical Pharmacology, 67(1): 5-21, 2008.

Zuurman et al. "Effect of Intrapulmonary Tetrahydrocannabinol Administration in Humans", Journal of Psychopharmacology, 22(7): 707-716, 2008.

Communication Pursuant to Article 94(3) EPC Dated Mar. 5, 2026 From the European Patent Office Re. Application No. 20751958.8 (6 Pages).

Examination Report Dated Mar. 6, 2026 From the Australian Government, IP Australia Re. Application No. 2024278426. (4 Pages).

Examination Report Dated Feb. 10, 2026 From the Australian Government, IP Australia Rc. Application No. 2025200462. (5 Pages).

Notification of Office Action and Search Report Dated Mar. 31, 2026 From the State Intellectual Property Office of the People's Republic of China Re. Application No. 202311526032.0 with its Summary and Machine Translation into English. (14 Pages).

Official Action Dated Apr. 1, 2026 from the US Patent and Trademark Office Re. U.S. Appl. No. 17/684,452. (25 pages).

Official Action Dated Mar. 9, 2026 from the US Patent and Trademark Office Re. U.S. Appl. No. 16/969,612. (103 pages).

Official Action Dated Mar. 13, 2026 from the US Patent and Trademark Office Re. U.S. Appl. No. 17/428,706. (35 Pages).

Requisition by the Examiner Dated Apr. 13, 2026 From the Innovation, Science and Economic Development Canada, Canadian Intellectual Property Office Re. Application No. 3,090,359. (3 Pages).

Requisition by the Examiner Dated Feb. 20, 2026 From the Innovation, Science and Economic Development Canada, Canadian Intellectual Property Office Re. Application No. 3,215,815. (4 Pages).

Examination Report Dated Jun. 4, 2026 From the Australian Government, IP Australia Re. Application No. 2025202831. (3 Pages).

Grounds of Reason of Rejection Dated May 15, 2026 From the Korean Intellectual Property Office Re. Application No. 10-2025-7009788 and Its Translation Into English. (9 Pages).

Official Action Dated Jun. 10, 2026 from the US Patent and Trademark Office Re. U.S. Appl. No. 19/026,779, (71 pages).

Official Action Dated May 22, 2026 together with Interview Summary from the US Patent and Trademark Office Re. U.S. Appl. No. 18/234,882. (24 pages).

* cited by examiner

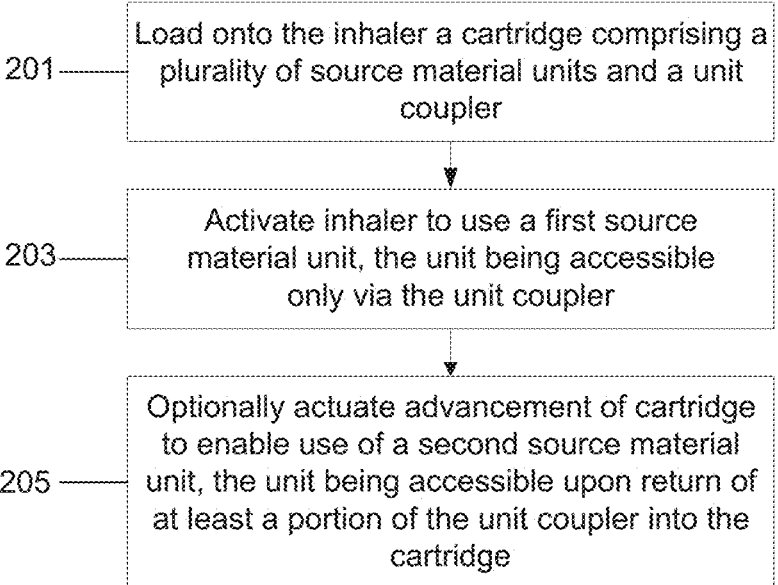

201 — Load onto the inhaler a cartridge comprising a plurality of source material units and a unit coupler 203 — Activate inhaler to use a first source material unit, the unit being accessible only via the unit coupler 205 — Optionally actuate advancement of cartridge to enable use of a second source material unit, the unit being accessible upon return of at least a portion of the unit coupler into the cartridge

Fig. 2

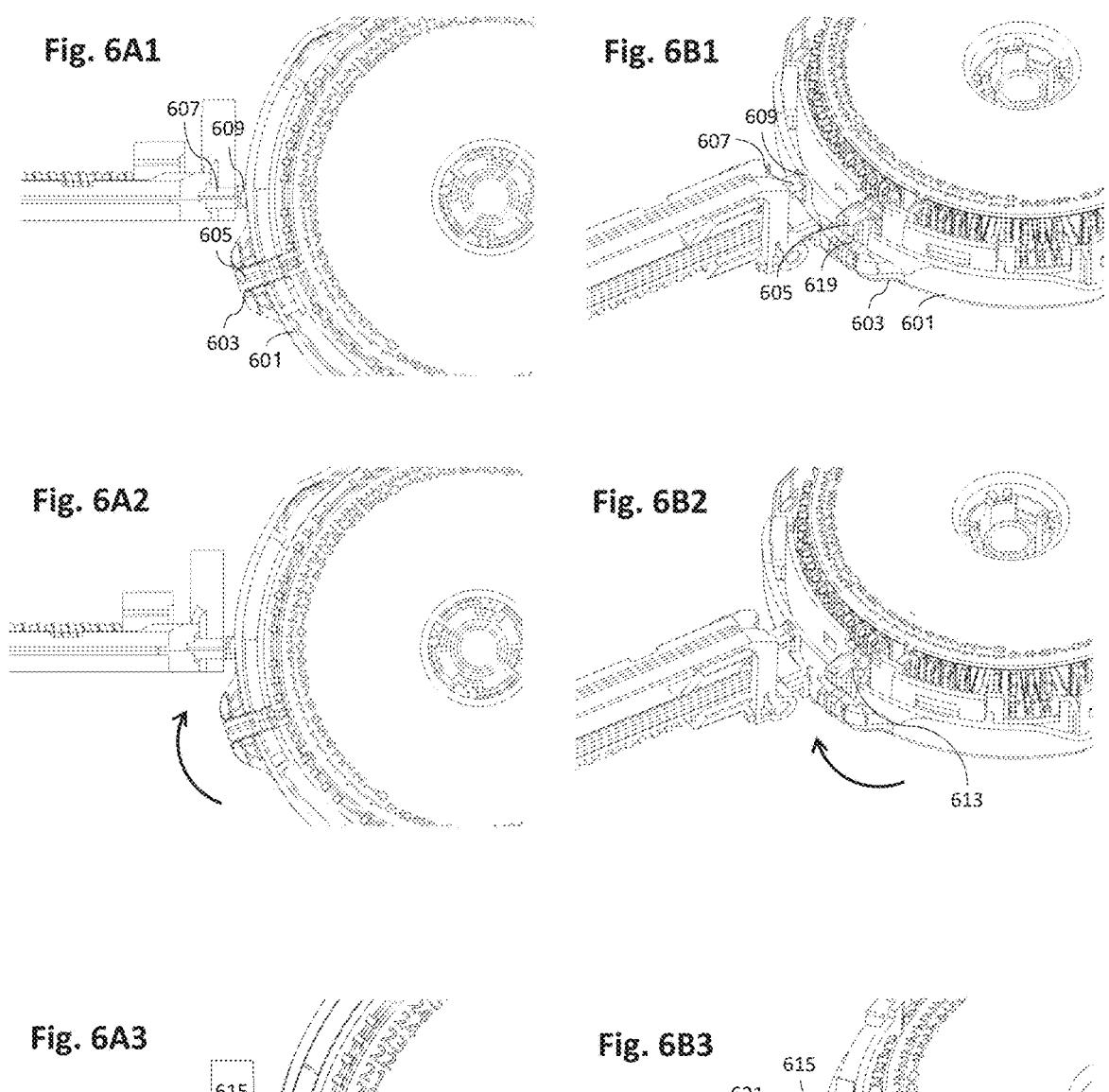
Fig. 6A1
Fig. 6B1
Fig. 6A2
Fig. 6B2
Fig. 6A3
Fig. 6B3

1003
1007
1001

1005
1015

1009

1201 — Place a cartridge comprising a plurality of source material units in a designated cavity of an inhaler 1203 — Rotate cartridge to a final position, releasing a restrictor of the unit coupler of the cartridge 1205 — Close inhaler cover door over the cartridge, releasing a stopper to allow internal movement of the source material units 1301 — Load onto the inhaler a cartridge comprising a plurality of source material units 1303 — Activate inhaler to use a source material units 1305 — Repeat until inhaler identifies that the last source material unit in the cartridge had been used based on structural variations in the cartridge 1307 — Remove cartridge from inhaler, and optionally replace with a new cartrdige

1501

1507

1509    1505

1503

1503

1515

1510

1517

CARTRIDGE UNIT COUPLER

RELATED APPLICATIONS

This application is a National Phase of PCT Patent Application No. PCT/IL2019/051163 having International filing date of Oct. 28, 2019, which claims the benefit of priority under 35 USC § 119(e) of U.S. Provisional Patent Application No. 62/751,636 filed on Oct. 28, 2018. The contents of the above applications are all incorporated by reference as if fully set forth herein in their entirety.

FIELD AND BACKGROUND OF THE INVENTION

The present invention, in some embodiments thereof, relates to a source material cartridge for use with an inhaler and, more particularly, but not exclusively, to transfer of a source material unit from the cartridge to and/or from a use-position within the inhaler.

U.S. Pat. No. 9,802,011 by the present assignees discloses: "Devices and methods are described for preparing, managing, and/or administering metered doses of substances for vaporized administration. In some embodiments, dose cartridges comprising at least one botanical substance include a heating element integrated into the cartridge in close contact with the botanical substance. In some embodiments, cartridge-mounted doses are stored in a magazine, optionally in carousel form, before use. Transport of a cartridge from a magazine to an electrically operated vaporizing chamber which activates the heating element is provided by a mechanical pickup means." (Abstract).

SUMMARY OF THE INVENTION

According to an aspect of some embodiments there is provided a cartridge for use with an inhaler, the cartridge comprising: a plurality of source material units; and a unit coupler configured for selectively interlocking to each of the source material units so that when the cartridge is operably attached to the inhaler, manipulation of the unit coupler moves the interlocked source material unit away from or back into the cartridge; the unit coupler and each of the source material units being formed with an interlocking geometry in which a protrusion of one fits within a respective recess of the other.

According to an aspect of some embodiments there is provided a cartridge for use with an inhaler, the cartridge comprising: a housing comprising: a plurality of source material units; and a unit coupler configured for selectively interlocking to each of the source material units, the unit coupler positioned and configured to move away from or back into the housing with an interlocked source material unit; the unit coupler and each of the source material units being formed with an interlocking geometry in which a protrusion of one fits within a respective recess of the other.

In some embodiments, the unit coupler comprises a distal protrusion shaped and sized to fit within a respective recess defined in each of the source material units. In some embodiments, the cartridge housing comprises a geometry defining two movement pathways: a first pathway in which the plurality of source material units are configured to slide past the unit coupler; and a second pathway in which a source material unit that was interlocked to the unit coupler at the first pathway is configured to move together with the unit coupler along the second pathway. In some embodiments, the first pathway is structured for rotational movement of the source material units relative to the unit coupler; and the second pathway is structured for joint linear movement of the interlocked unit coupler and source material unit. In some embodiments, the plurality of source material units are arranged on a carousel and are rotatable with respect to the unit coupler; the unit coupler being positioned radially outwardly with respect to the carousel. In some embodiments, the unit coupler is located at a passageway of the cartridge housing. In some embodiments, the unit coupler is linearly aligned with the transferring element when the cartridge is seated at a final position with respect to the inhaler. In some embodiments, an external side of the housing of the cartridge is formed with a bulge, and at least a portion of the unit coupler extends into the bulge on an inner side of the bulge. In some embodiments, the housing is substantially rounded and the bulge is positioned to align the cartridge with respect to a designated cavity in the inhaler in which the cartridge is received. In some embodiments, the unit coupler interlocks to only one source material unit at a given time and only that source material unit can be pulled away from or returned back into the cartridge. In some embodiments, the bulge defines a passageway having a width that matches a thickness of a source material unit, so that only one source material unit can pass through the passageway at a given time. In some embodiments, the cartridge comprises a restricting frame that is movable between a first position in which it prevents movement of the unit coupler out from the cartridge, and a second position in which an opening of the restricting frame is aligned with the unit coupler to allow its movement. In some embodiments, an inhaler for use with the source material cartridge comprises a transferring element shaped and sized to engage the unit coupler to pull the source material unit into a use-position within the inhaler body. In some embodiments, a distal end of the transferring element is shaped to attach to the unit coupler of the cartridge by a slide fit coupling. In some embodiments, the distal end of the transferring element is T-shaped. In some embodiments, the transferring element is slidable on a shaft between proximal and distal positions. In some embodiments, movement of the transferring element on the shaft is actuated by motorized rotation of a screw. In some embodiments, the transferring element comprises a distal head formed with one or more angled surfaces shaped and sized to guide insertion of the cartridge into a designated cavity of the inhaler. In some embodiments, the transferring element, unit coupler and source material unit are linearly aligned with respect to each other when the cartridge is in a locked position with respect to the inhaler.

According to an aspect of some embodiments there is provided a method for pulling a source material unit from a cartridge configured for use with an inhaler, the method comprising: loading onto the inhaler a cartridge comprising a plurality of source material units and a unit coupler configured for interlocking with one of the source material units; and locking the cartridge to the inhaler while simultaneously engaging the unit coupler in preparation for pulling an interlocked source material unit to a use-position within the inhaler. In some embodiments, the unit coupler in the provided cartridge is interlocked with a source material unit before being loaded onto the inhaler. In some embodiments, interlocking a source material unit to the unit coupler is performed simultaneously with locking the cartridge to the inhaler. In some embodiments, loading the cartridge comprises releasing a restricting frame of the cartridge to allow movement of the unit coupler from a position in which its movement is restricted to a position in which it's movement from or to the cartridge is enabled. In some embodiments, the method further comprises returning the source material unit, after it had been used, back into the cartridge. In some embodiments, engaging the unit coupler comprises moving a transferring element of the inhaler to a position in which the transferring element connects to the unit coupler. In some embodiments, the transferring element moves the source material unit to the use-position in which the source material unit is in communication with an airflow tract of the inhaler. In some embodiments, the transferring element moves the source material unit to the use-position in which heat and/or an electrical current are applied to the source material unit to release at least one active substance from the source material. In some embodiments, loading the cartridge comprises aligning the cartridge with respect to a cavity of the inhaler. In some embodiments, locking the cartridge with respect to the inhaler linearly aligns a transferring element of the inhaler with the unit coupler of the cartridge.

According to an aspect of some embodiments there is provided an inhaler for use with a source material cartridge comprising a plurality of source material units; the inhaler comprising a transferring element configured to move between a proximal position within the inhaler and a distal position in which it is configured to reach out to the cartridge when the cartridge is loaded onto the inhaler, to actuate transfer of a source material unit to a use-position in the inhaler; a distal end of the transferring element being shaped and positioned with respect to the loaded cartridge such that rotation of the cartridge does not break or otherwise damage the transferring element. In some embodiments, a kit is provided, comprising the inhaler and a cartridge comprising a plurality of source material units and a unit coupler configured for selectively interlocking to each of the source material units. In some embodiments, the transferring element is configured to connect to the unit coupler when the transferring element is at its distal position. In some embodiments, the cartridge is substantially rounded and comprises a bulge, and a distal end of the transferring element, at its distal position, extends adjacent an indentation in which the bulge of the cartridge is seated.

According to an aspect of some embodiments there is provided a kit comprising an inhaler and a source material cartridge for use with the inhaler, the cartridge comprising an RFID tag and the inhaler being configured to read and write to the RFID tag of the cartridge data regarding usage of the source material units of the cartridge.

According to an aspect of some embodiments there is provided a cartridge for use with an inhaler, the cartridge comprising: a housing comprising: a plurality of source material units arranged in a carousel; and a bulge located on an external side of the housing, the bulge positioned to limit rotation of the carousel, when the cartridge is positioned in the inhaler, in at least one of clockwise direction and counter clockwise direction; wherein rotation is limited to an angular position in which each source material unit can be accessed for use only once.

According to an aspect of some embodiments there is provided a cartridge for use with an inhaler, the cartridge comprising a plurality of source material units arranged in a carousel; rotation of the carousel being limited in at least one of clockwise direction and the counter clockwise direction to an extent that does not pass the first source material unit, to prevent approach to source material units that were already used. In some embodiments, rotation of the carousel is limited in both the clockwise and counter clockwise directions.

According to an aspect of some embodiments there is provided a cartridge for use with an inhaler, the cartridge comprising a plurality of source material units arranged within slots of a carousel; one or more of the last 10% of slots in the carousel comprising an indicator for identifying that the cartridge was fully used. In some embodiments, the indicator includes an empty slot that does not include a source material unit. In some embodiments, the indicator includes a unit that does not include an electrically conductive member. Optionally, a unit is otherwise identified as being an indicator (e.g. by having significantly lower or higher resistance to an electric current than a source material unit or by being resistant to removal from the slot, and/or by having a different color and/or shape, which can be detected by an optical sensor or the like).

According to an aspect of some embodiments there is provided a cartridge for use with an inhaler, the cartridge comprising: a plurality of source material units arranged on a carousel; and a stopper comprising one or more teeth that extend in between adjacent source material units to interfere with rotation of the carousel.

According to an aspect of some embodiments there is provided a cartridge for use in an inhaler, the cartridge comprising; a housing; a plurality of source material units stacked or rotationally aligned with respect to the housing; at least one indicator positioned between adjacent source material units. In some embodiments, the cartridge is a packaged, air-sealed cartridge and the at least one indicator is placed during manufacturing of the cartridge. In some embodiments, the indicator comprises an empty slot or a source material unit having a structure different than a structure of at least 70% of a total number of source material units in the cartridge. In some embodiments, the cartridge comprises an RFID tag which includes or is configured to record data related to one or more of: usage of the source material units, content of the source material units, a relative position of the at least one indicator with respect to the housing, a relative position of each of the plurality of source material units with respect to the indicator. In some embodiments, there is provided an inhaler device configured to receive the cartridge, the inhaler comprising: a cavity shaped and sized for receiving the cartridge therein; a controller configured to infer a relative position of one or more source material units of the cartridge based on a position of the indicator.

In some embodiments, the controller infers a position of the indicator based on signals received from at least one of an optical sensor and an electrical resistance sensor. In some embodiments, the inhaler device comprises circuitry configured to read and write data to an RFID tag of the cartridge, and the controller is configured determine whether a current position of an indicator correlates to data of the RFID tag to verify the cartridge position in the inhaler cavity.

According to an aspect of some embodiments there is provided a method for identifying a relative position of one or more source material units in a cartridge usable with an inhaler device, comprising: attaching the cartridge to the inhaler device; identifying, via circuitry of the inhaler device, a position of one or more indicator positions in the cartridge or a pattern including at least one empty slot and a plurality of source material units; and inferring a relative position of one or more source material units based on the identified position of the indicator or the pattern which includes the indicator.

According to an aspect of some embodiments there is provided an inhaler for use with a cartridge comprising a plurality of source material units; the inhaler comprising: a housing defining a cavity for receiving the cartridge, and a rotating gear configured at or directly beneath a surface of the cavity on which the cartridge is placed, the rotating gear configured to actuate rotation of the cartridge, when inserted, to move the plurality of source material units. In some embodiments, the inhaler further comprises a protruding element which when contacted by a cover door of the inhaler housing moves a clutch into engagement with the rotating gear. Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 2 is a flowchart of a general method of using an inhaler configured to be operably coupled to a cartridge including a plurality of source material units and a unit coupler, according to some embodiments;

Figure 3:
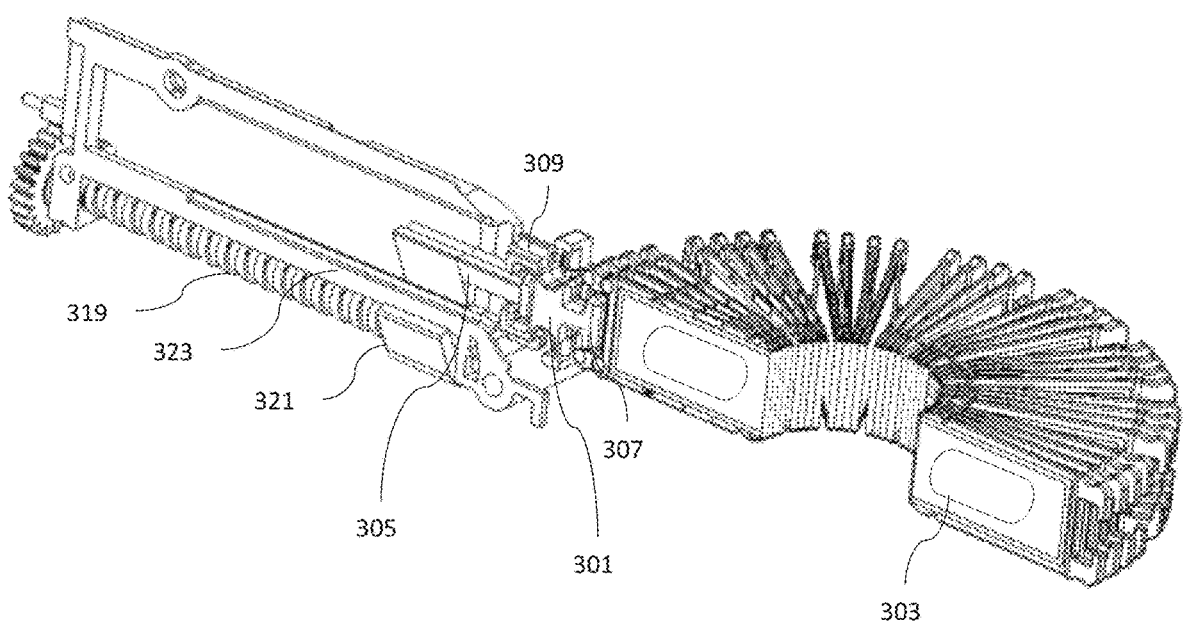
FIG. 3 is a cross section view of a mechanism for engaging a source material unit contained in a cartridge, according to some embodiments.
Figure 4A:
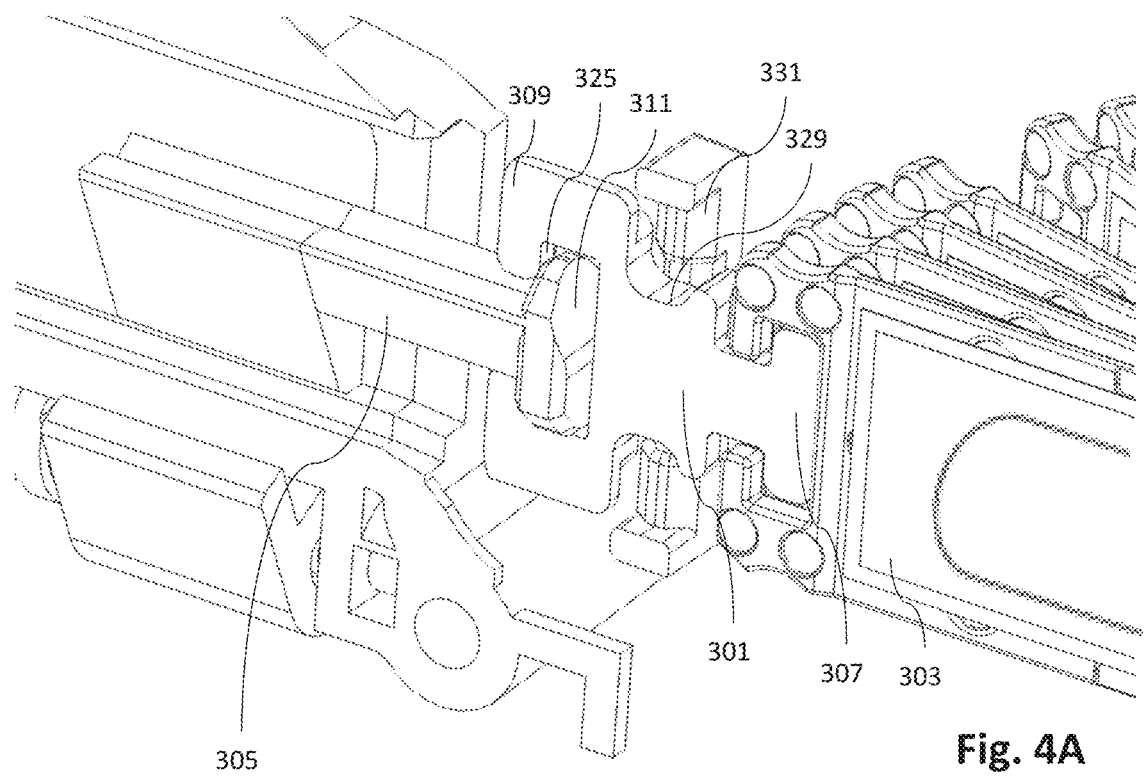
Figure 4C:
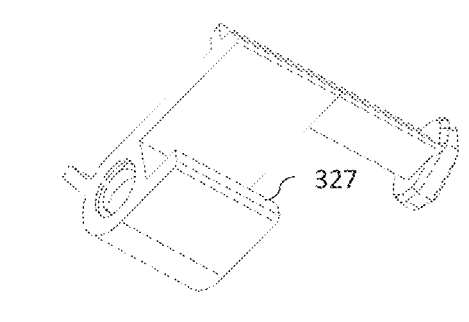
Figure 4B:
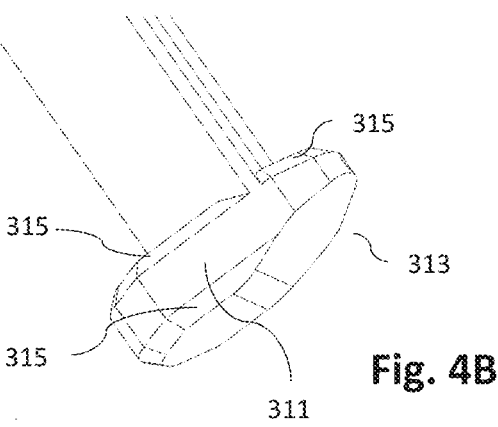
Figure 5A:
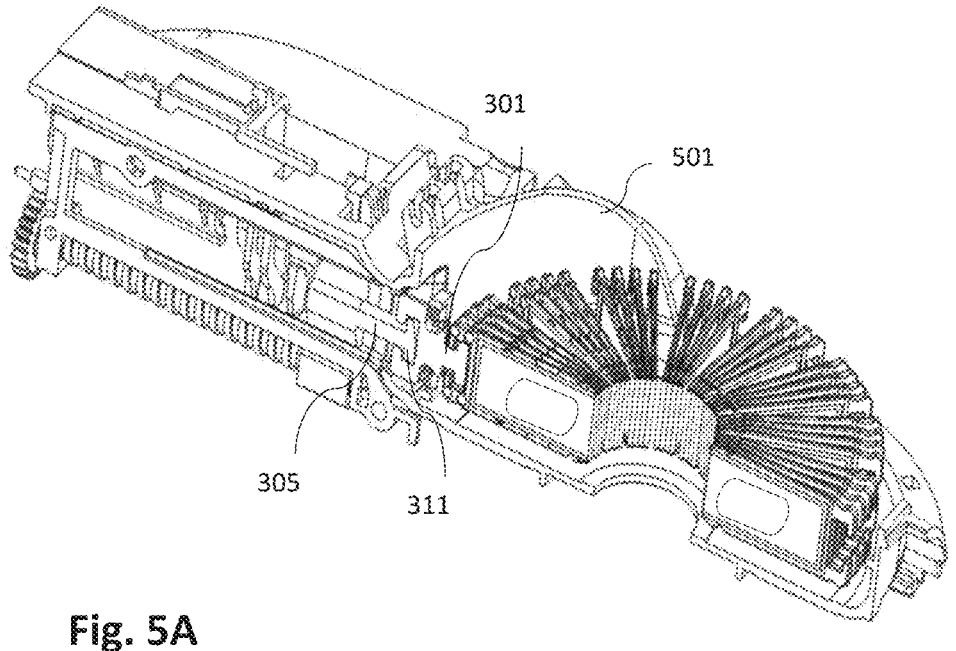
Figure 5B:
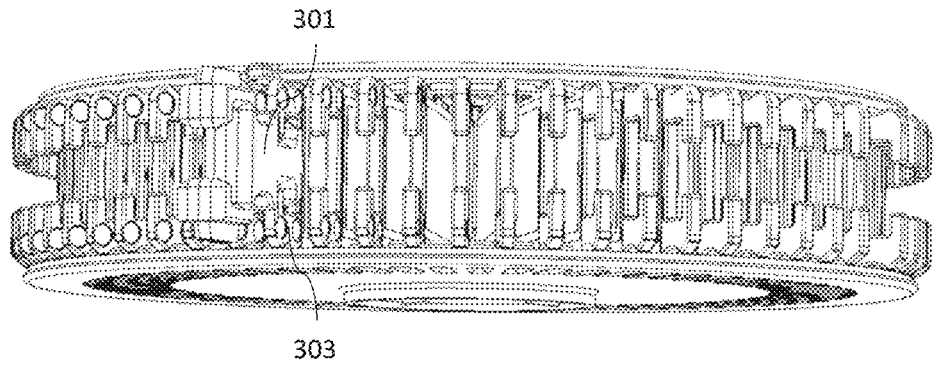
Figure 7A:
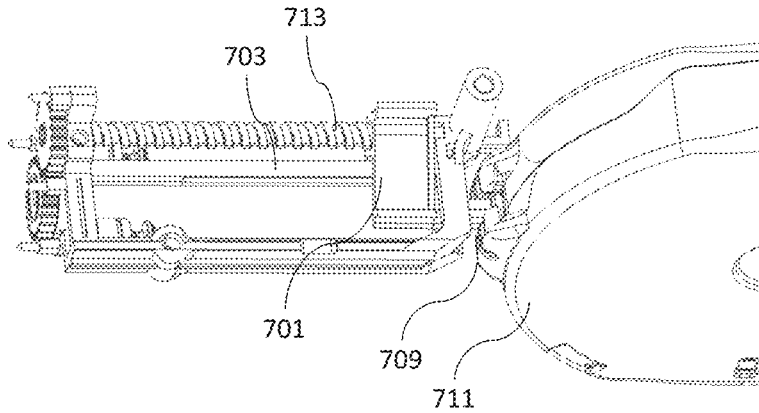
Figure 7B:
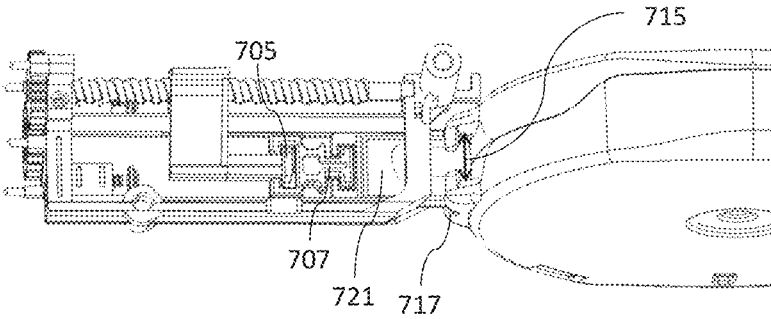
Figure 7C:
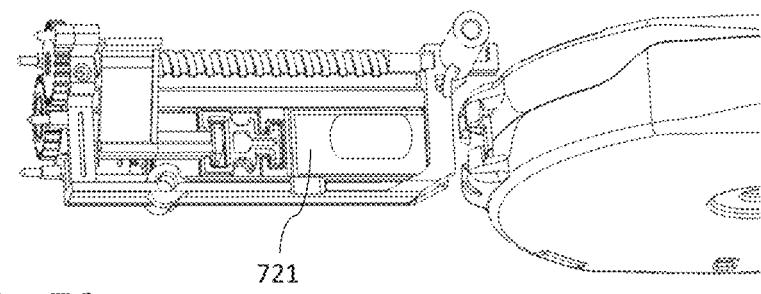
Figure 8B:
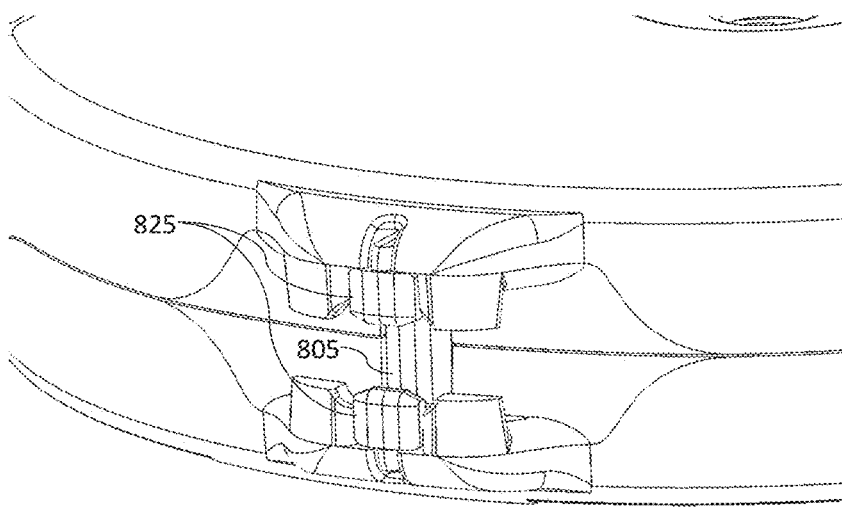
Figure 8A:
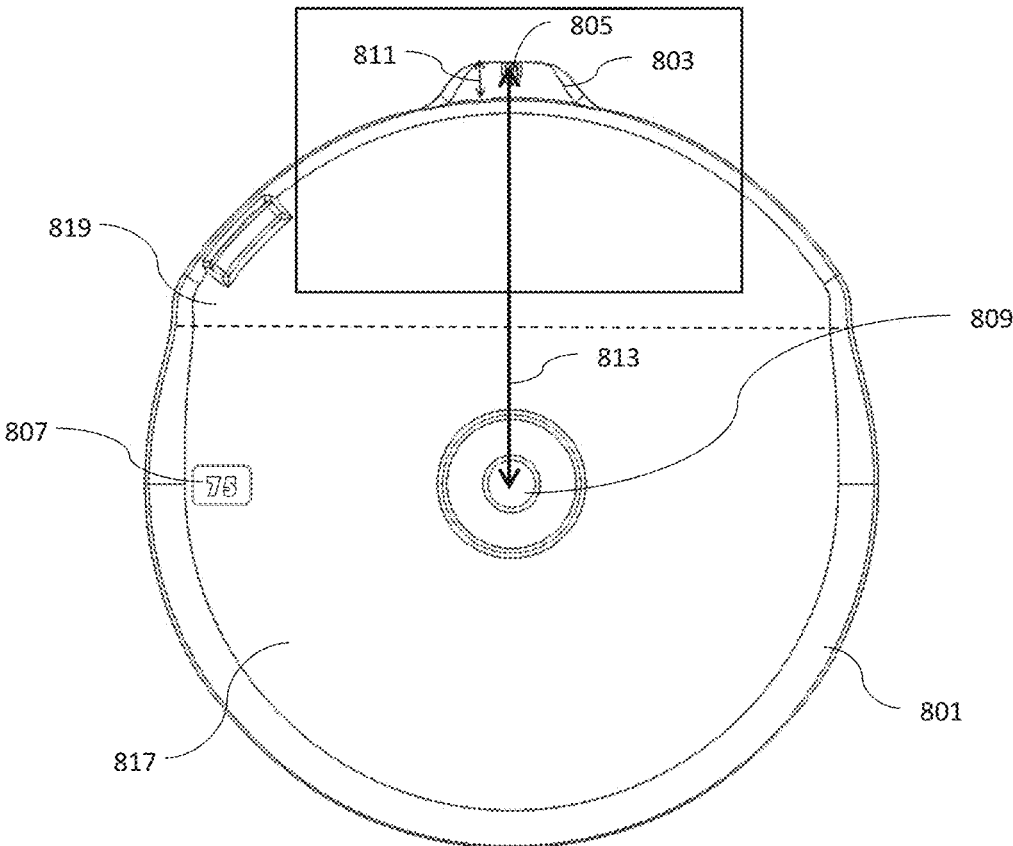
Figure 9A:
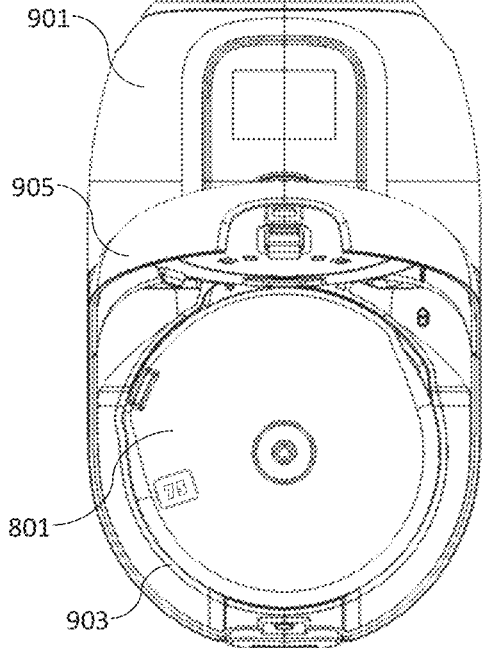
Figure 9B:
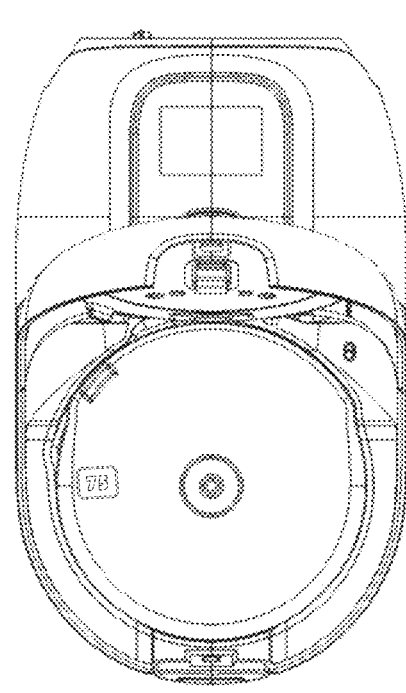
Figure 10A:
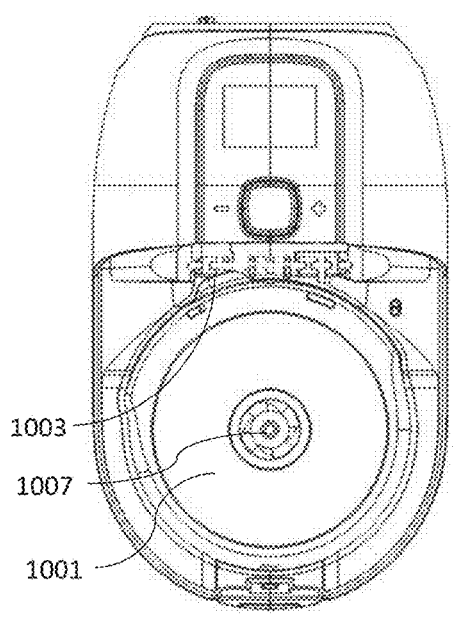
Figure 10B:
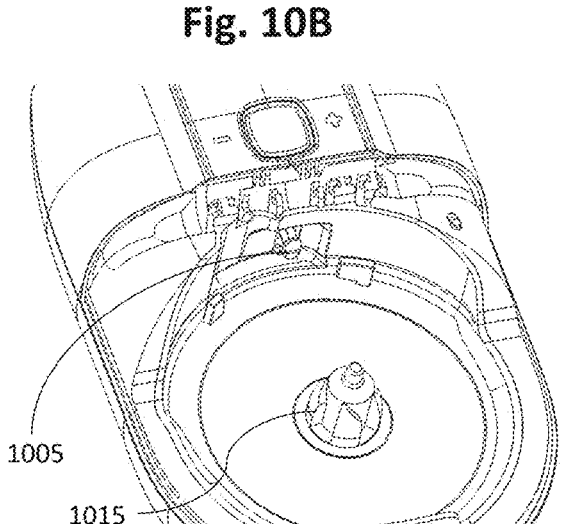
Figure 10C:
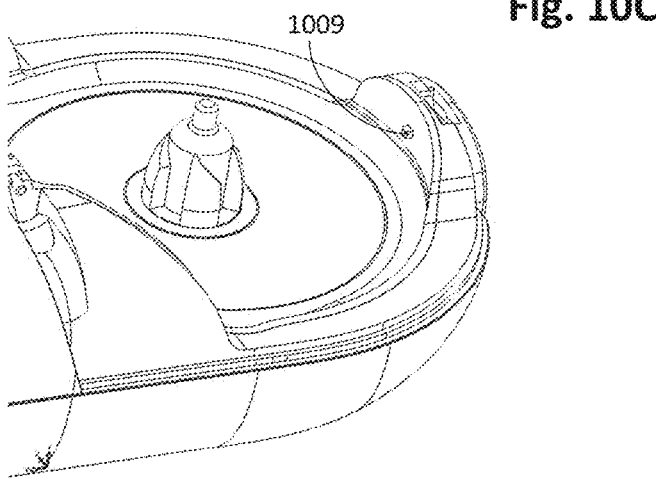
Figure 11A:
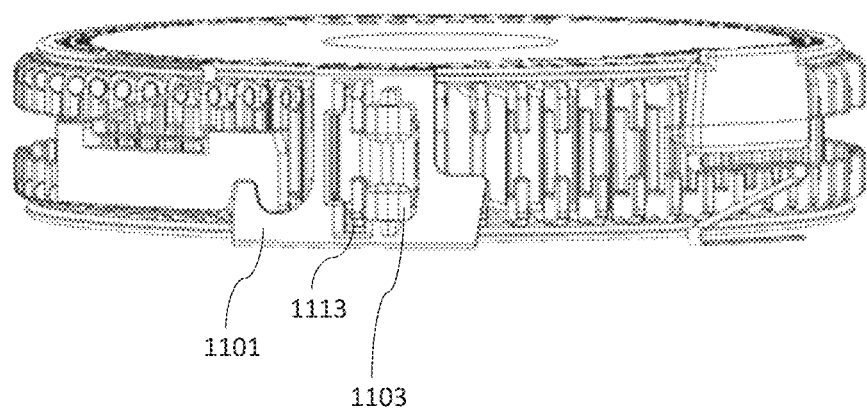
Figure 11B:
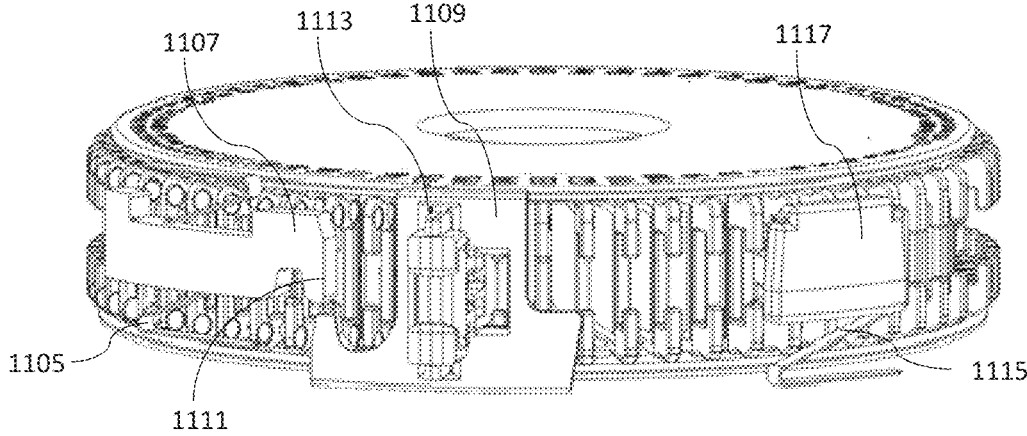
Figure 11C:
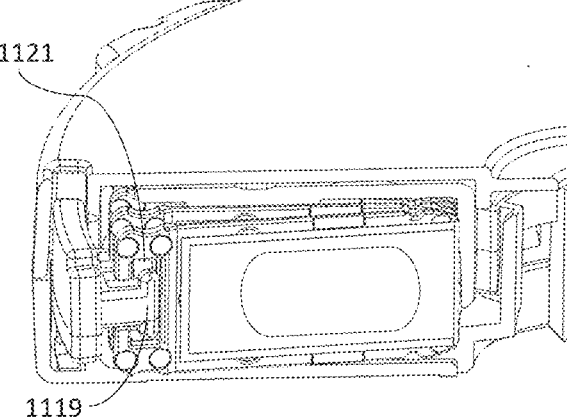
Figure 12:
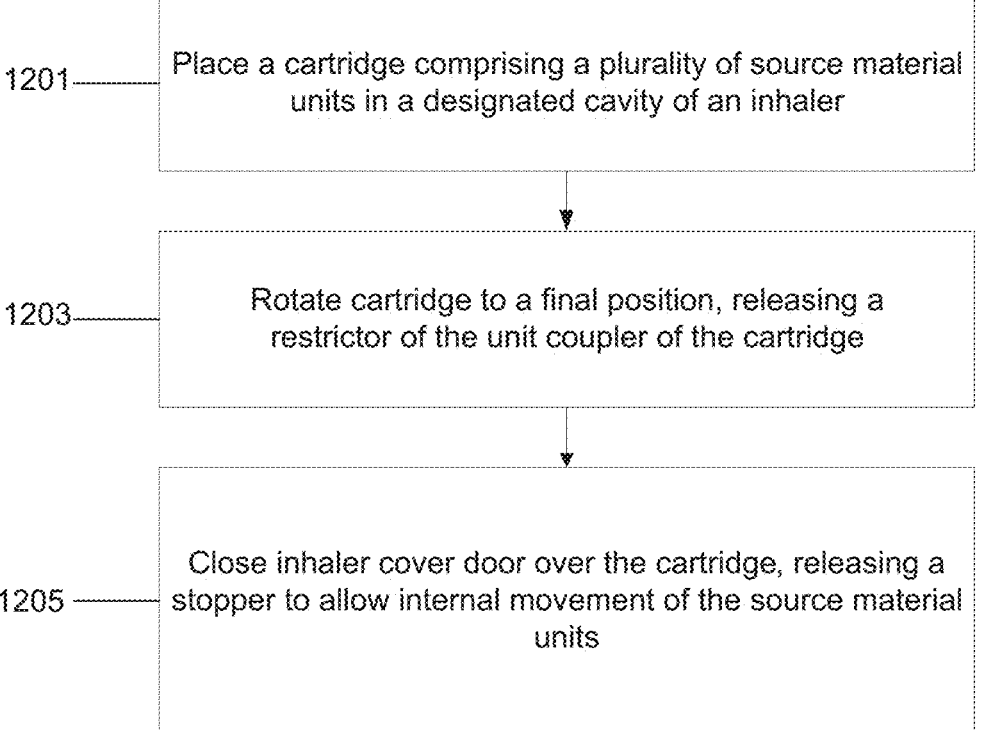
Figure 13:
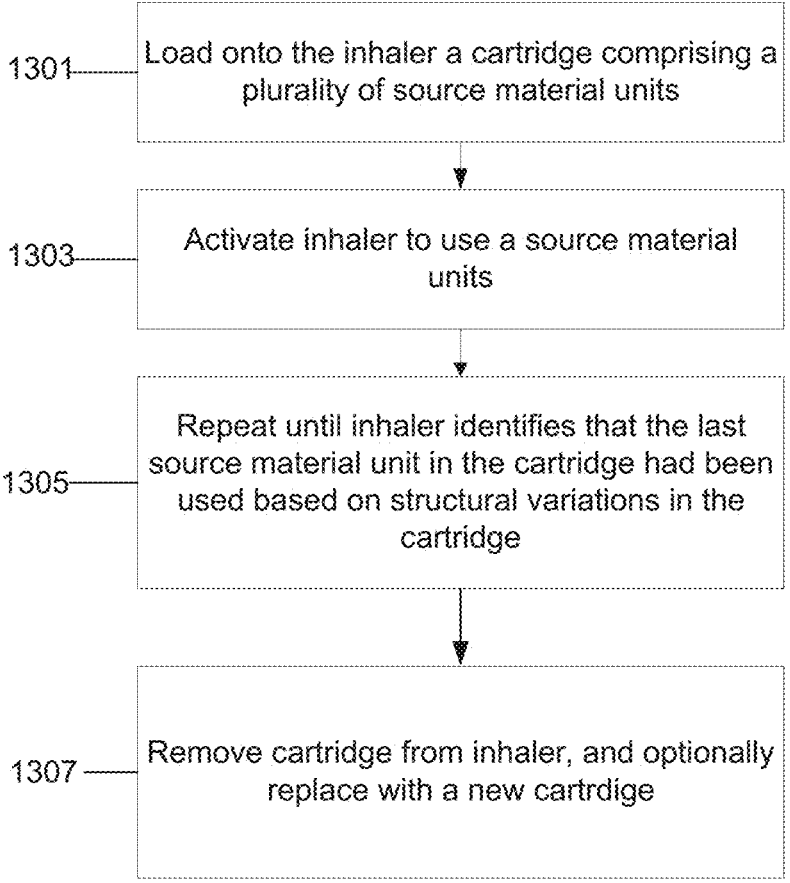
Figures 14A, 14B:
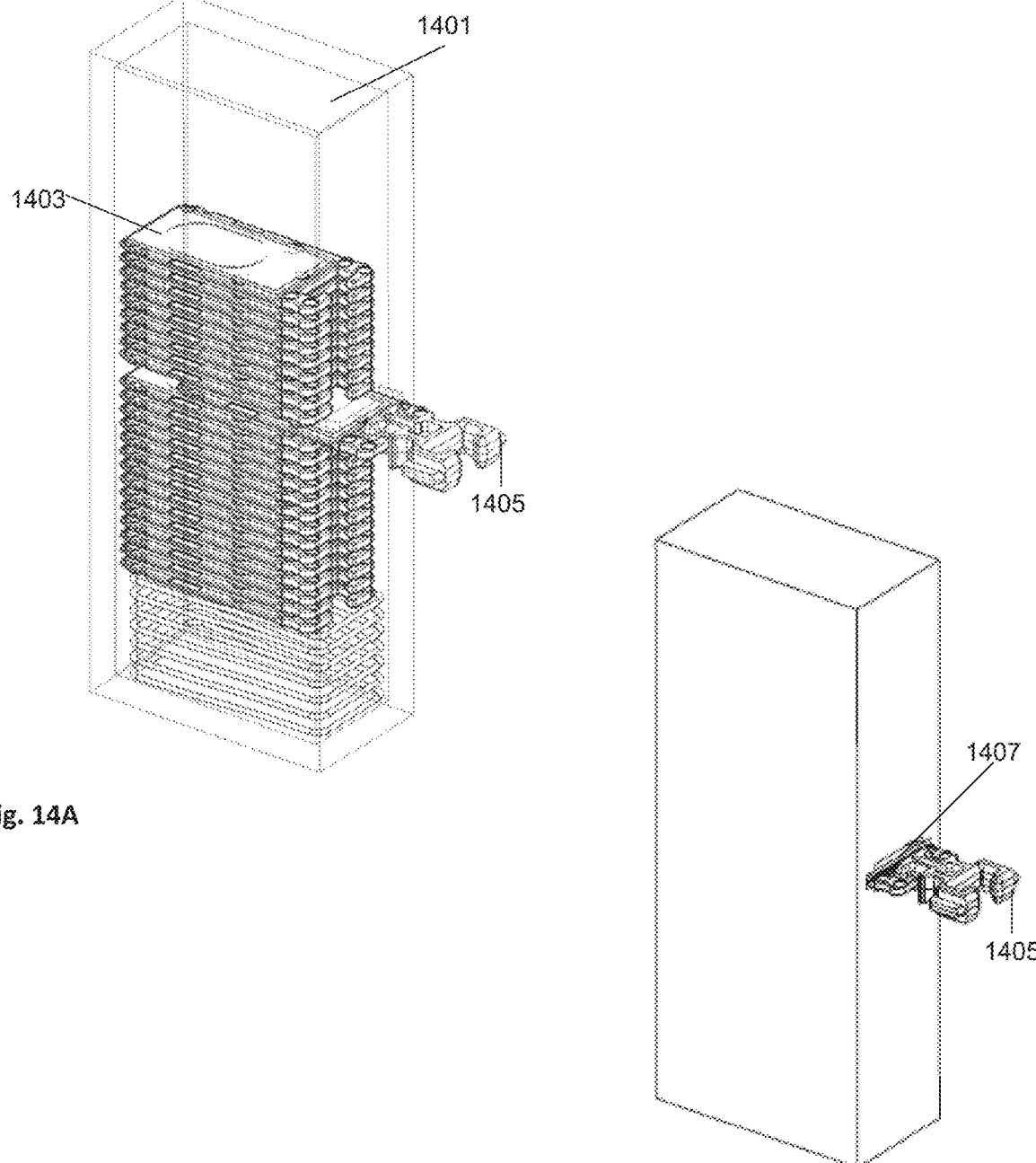
Figure 15A:
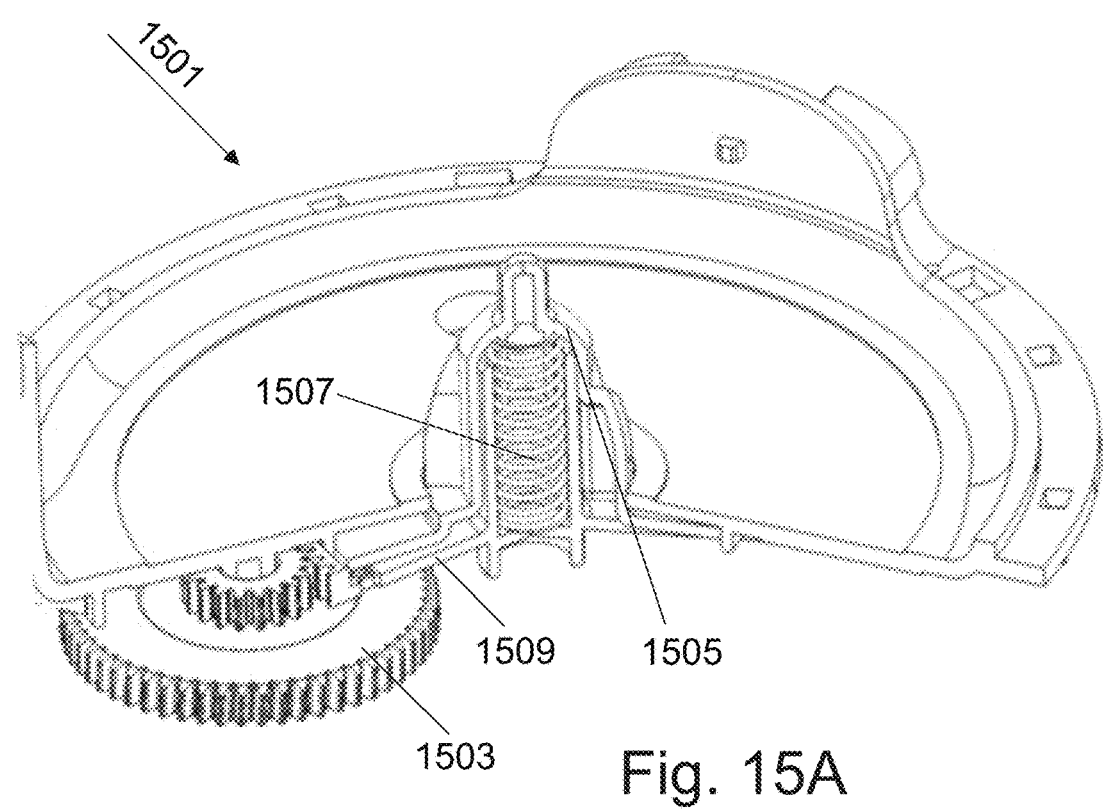
Figure 15B:
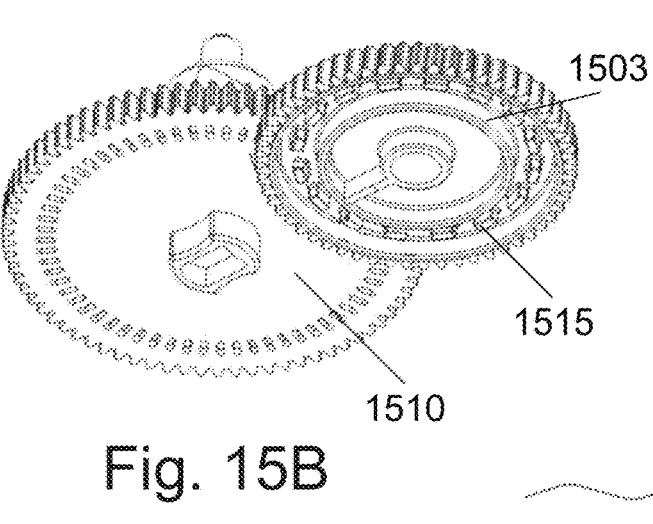
Figure 15C:
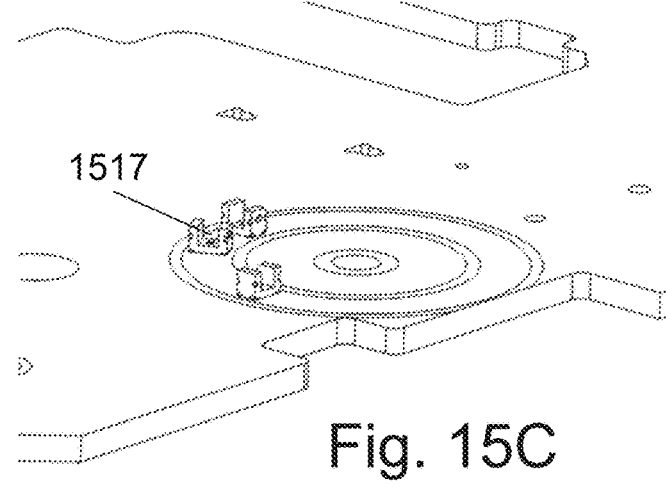

FIGS. 4A-C are a detailed view of a part of the mechanism of FIG. 3 (FIG. 4A), and a detailed view of a transferring element in the form of a slider (FIGS. 4B, 4C), according to some embodiments;

FIGS. 5A-B are a cross sectional view of a mechanism for example as shown in FIG. 3, and an isometric view of the unit coupler, according to some embodiments;

FIGS. 6A1-6B3 are a side view (6A1, 6A2, 6A3) and an isometric view (6B1, 6B2, 6B3) of a process of positioning a cartridge including a unit coupler and a plurality of source material units in a use position with respect to an inhaler, according to some embodiments;

FIGS. 7A-C illustrate a process of pulling a source material unit from a cartridge, according to some embodiments;

FIGS. 8A-B are an illustration of a cartridge comprising a bulge (8A) and a detailed view of the bulge showing the unit coupler (8B), according to some embodiments.;

FIGS. 9A-B are illustrations of an inhaler including a cartridge for example as shown in FIGS. 8A-B in an initially inserted position (FIG. 9A) and in a use position (FIG. 9B), according to some embodiments;

FIGS. 10A-C are different views of an inhaler cavity in which a source material cartridge is received, according to some embodiments;

FIGS. 11A-C show a restricting frame and a movement stopper of the cartridge, in a locked position and a released position, according to some embodiments;

FIG. 12 is a flowchart of a cartridge loading method which concurrently releases locking mechanisms of the cartridge, according to some embodiments;

FIG. 13 is a flowchart of a method for identifying a fully used cartridge, in accordance with some embodiments;

FIGS. 14A-B are an internal view (FIG. 14A) and an external view (FIG. 14B) of a linear cartridge comprising a unit coupler, according to some embodiments; and FIGS. 15A-C include a cross section view of an inhaler cavity for receiving a cartridge, comprising a clutch and gear mechanism (FIG. 15A), and components associated with operation of the gear mechanism (FIGS. 15B-C), according to some embodiments.

DESCRIPTION OF SPECIFIC EMBODIMENTS OF THE INVENTION

The present invention, in some embodiments thereof, relates to a source material cartridge for use with an inhaler and, more particularly, but not exclusively, to transfer of a source material unit from the cartridge to and/or from a use-position within the inhaler.

An aspect of some embodiments of the invention relates to a cartridge for use with an inhaler, the cartridge comprising a plurality of source material units and a unit coupler configured to engage a source material unit. In some embodiments, the unit coupler is positioned such that it extends at least partially into a passageway of the cartridge, so that upon loading of the cartridge onto an inhaler, the unit coupler is accessible. In some embodiments, the unit coupler is attached to a first source material unit, and following use of the unit, the unit is returned to the cartridge along with the unit coupler. The plurality of source material units within the cartridge can then be advanced, placing a different source material in attachment with the unit coupler. Optionally, a position of the unit coupler remains permanent while the source material units are moved with respect to the unit coupler. Alternatively, the unit coupler moves with respect the source material units.

In some embodiments, the unit coupler is coupled to the source material unit by an interference fit coupling, for example in which a portion of the unit coupler is shaped and sized to be received within a portion of the unit, or vice versa In some embodiments, each of the source material units is formed with a geometric space shaped and/or sized for receiving the unit coupler or a portion of it. In some embodiments, the unit coupler comprises a protrusion which is received within a respective recess of the source material unit, or vice versa—the source material unit comprises a protrusion which is received within a respective recess of the unit coupler. Other embodiments may include different types of connections between the unit coupler and the source material unit, for example a loose-fit connection, a slide-fit connection, an attachment via a third element (e.g. a screw) and/or other connection types.

In some embodiments, the unit coupler is connected to a first source material unit even before the cartridge is loaded onto the inhaler. A potential advantage of the first source material unit being already interlocked with the unit coupler may include that upon loading of the cartridge onto the inhaler, the already interlocked source material unit can be immediately (automatically or in response to user activation) transferred to a use-position within the inhaler. Alternatively, the unit coupler of a cartridge is not initially attached to any source material units. This may contribute to safe usage of the cartridge and reduce a risk of violation, as the process of pulling out a source material unit for use would require an additional step of interlocking the unit coupler with the first source material unit, which may be done simultaneously with loading of the cartridge or thereafter.

In some embodiments, the cartridge is structured to support two movement pathways: a first pathway in which the source material units slide past the unit coupler, until a selected source material unit interlocks with the unit coupler; and a second pathway in which the interlocked unit coupler and source material unit move together, for example pulled to a use-position within the inhaler or pushed back into cartridge. In some embodiments, in the first pathway, the source material units internally rotate within the cartridge. In some embodiments, in the second pathway, the unit coupler and the interlocked source material unit move together along a linear axis, extending for example radially outwardly relative to the cartridge housing. In some embodiments, movement along the second path takes place on a plane that is substantially perpendicular to movement along the first path.

An aspect of some embodiments of the invention relates to transferring a source material unit into and back from a use-position in the inhaler, the transferring enabled by assembling elements of both the inhaler and the cartridge together. In some embodiments, a source material unit can be pulled into use only once one or more elements of the inhaler, such as a transferring element, are operably attached to the unit coupler of the cartridge.

In some embodiments, loading of a cartridge onto an inhaler and/or positioning of the cartridge in a designated recess or cavity of the inhaler simultaneously connects a transferring element of the inhaler with a unit coupler of the cartridge, which in turn (concomitantly or later) is attached to a source material unit. Some embodiments may include more than one unit coupler, for example two, three, five, ten unit couplers or intermediate, larger or smaller number of unit couplers. Optionally, a plurality of unit couplers are used for collecting a plurality of source material units at a given time. In some embodiments, the transferring element of the inhaler is configured to attach to a plurality of unit couplers. Alternatively, the inhaler comprises a plurality of transferring elements, each configured to engage a unit coupler.

In some embodiments, a cartridge is provided with the unit coupler being already attached to the first source material unit. Optionally, loading of the cartridge onto the inhaler simultaneously engages the transferring element with the unit coupler, and the first source material unit can be immediately used. Alternatively, the unit coupler and the first source material unit are connected only upon loading of the cartridge onto the inhaler.

In operation, according to some embodiments, the transferring element is configured to move (e.g. slide) to bring a source material unit to a use- position in which at least one active substance can be released from the source material by operation of the inhaler. In some embodiments, the transferring element returns the used unit to the cartridge, for example by pushing the unit coupler along with the attached source material unit back in the direction of the cartridge.

In some embodiments, the use-position includes a position in which the unit is placed in communication with an airflow tract. In some embodiments, the use-position includes a position in which the source material of the unit can be heated so as to cause the at least one active substance to vaporize. Optionally, the source material is heated by a heating element, by conducting electrical current to at least a portion of the source material unit, by positioning the unit within a heating chamber and/or other. In some embodiments, the use-position includes a location within the inhaler housing in which the source material unit is clamped in place by one or more clamping elements. Optionally, the clamping elements comprise electrical contacts, such as electrodes.

In some embodiments, pulling of a consecutive source material unit to the use-position can take place only once the previously used unit was returned into the cartridge by a transferring element and the unit coupler. Optionally, the transferring element and the unit coupler remain attached to each other as long as the cartridge is maintained in a position relative to the inhaler. Optionally, the transferring element and the unit coupler remain attached to each other as long as the source material unit is not placed in the cartridge.

In some embodiments, a source material unit (optionally the last unit of the cartridge) may remain inside the inhaler still being attached to the unit coupler, while the cartridge is replaced by a new cartridge. Optionally, the new cartridge includes an empty slot for receiving the source material unit of the previous cartridge, once it had been used. In some embodiments, an inhaler controller is programmed (in some embodiments, re-programmed) to allow such replacement.

In some embodiments, the cartridge comprises one or more indication slots. In some embodiments, the indication slots are distributed between sections, each section including one or more source material units. In some embodiments, a sequence of a plurality of source material units is followed by a plurality of indication slots. Optionally, indication slots are positioned to separate between units having different types of source materials and/or combinations thereof. Additionally or alternatively, an indication slot positioned in a predefined position within the cartridge (or a plurality of such indication slots) may be operative to mark a specific location (such as the indication slot itself in the case of a single indication slot) as confirmation that the numbering of slots correlates to a number used by the inhaler memory. Additionally or alternatively, the indication slots may be operative to mark each source material unit by its relative position with respect to one or more indication slots, thereby to identify the type and/or number of the source material unit and/or whether the source material unit has been previously used. Additionally or alternatively, an indication slot may be used as storage, for example for inserting a source material unit, once it has been used, to a designated position.

In some embodiments, the indication slots include a unit that does not include an electrically conductive member. Optionally, a unit is otherwise identified as being an indication slot (e.g. by having significantly lower or higher resistance to an electric current than a source material unit or by being resistant to removal from the slot.

Optionally, at least some of the indication slots are empty slots. In some embodiments, the empty slots are distributed between sections, each section including one or more source material units. In some embodiments, a sequence of a plurality of source material units is followed by a plurality of empty slots. Optionally, empty slots are positioned to separate between units having different types of source materials and/or combinations thereof. Additionally or alternatively, an empty slot positioned in a predefined position within the cartridge (or a plurality of such empty slots) may be operative to mark a specific location (such as the empty slot itself in the case of a single empty slot) as confirmation that the numbering of slots correlates to a number used by the inhaler memory. Additionally or alternatively, the empty slots may be operative to mark each source material unit by its relative position with respect to one or more empty slots, thereby to identify the type and/or number of the source material unit and/or whether the source material unit has been previously used. Additionally or alternatively, an empty slot may be used as storage, for example for inserting a source material unit, once it has been used, to a designated position.

In an example, a source material unit is pulled out from a carousel into a use position in the inhaler. During or following use of the source material, the carousel is rotated, aligning an empty slot with the unit coupler. The used source material unit can then be returned to an empty slot which is optionally different from the slot it was pulled from. Optionally, this process is repeated for multiple source material units, potentially placing all used units at a defined region of the carousel. Optionally, source material units are used in an arbitrary order or otherwise selected order (i.e. as opposed to a serial order corresponding with the position of the units on the carousel), and can then be returned to serially arranged empty slots.

In some embodiments, the one or more indication slots are pre-positioned (e.g. during manufacturing of the cartridge) at predefined locations between the source material units of the cartridge. In some embodiments, a packaged cartridge (for example, in an air-sealed packaging) includes the plurality of indication slots at pre-defined positions along the cartridge (e.g. predefined positions along the carousel).

In some embodiments, the control system of the inhaler (e.g. the inhaler controller) "expects" the one or more indication slots upon initial insertion of the cartridge into the inhaler and/or during use of an already inserted cartridge. In an example, the controller identifies a position of one or more indication slots upon insertion of the cartridge, and can thereby verify that the cartridge was placed in a correct position and/or alignment.

In some embodiments, the control system (e.g. the inhaler controller) is configured to identify a discrepancy, i.e., an indication slot where a source material unit was expected, or a source material unit in a place where an indication slot was expected. Upon identified discrepancy, the system may automatically fix the position, for example, by rotating the cartridge to the correct position. Alternatively, upon identified discrepancy, the system may issue an alert, which may indicate to a user to manually fix the position of the cartridge. Additionally or alternatively, the system otherwise alerts the user regarding operation failure.

Optionally the indication slot is an empty slot and identifying is via a sensor (e.g. mechanical and/or optical sensor) and/or by detecting a change in the electrical resistance of the circuitry, when electrical contact is formed with the unit.

In some embodiments, a control system in the inhaler (e.g. the inhaler controller) is configured to identify which of the source material units is currently being used, which was previously used, which is intended for upcoming use or the like. Optionally, identifying is via a sensor (e.g. mechanical and/or optical sensor) and/or by detecting a change in the electrical resistance of the circuitry, when electrical contact is formed with the unit. Optionally, the controller identifies one or more properties of a source material unit (e.g. current or upcoming position, content) based on a pre-defined order of units in the cartridge (e.g. an order pre-programmed or hardwired into the system). Optionally, the controller identifies one or more properties of a source material unit according to a current position of one or more indication slots. Optionally, the controller identifies one or more properties of a source material unit by identifying a pattern which includes source material unit and indication slots (for example: a pattern where an indication slot is detected adjacent multiple source material units (e.g. 2, 3, 4, 5 source material units) indicates, for example, the beginning of a sector which contains a source material of a specific known type.) Optionally the indication slots are empty slots and the pattern includes a series of empty slots and source material units. Optionally, the cartridge comprises a computer readable ID, such as an RFID, encoded with information on the cartridge content and/or order of units and/or the number and/or position of indication slots.

In some embodiments, a consecutive unit can be pulled out only once the transferring element and the unit coupler were returned to a "ready to pull" position, in which at least a portion of the unit coupler and optionally also a portion of the transferring element have entered the cartridge housing. Some potential advantages of conditioning use of a consecutive unit by return of the transferring element-unit coupler assembly to a "ready-to-pull" position may include reducing misuse, reducing a risk of violation, protecting the source material units that are currently not being used within the cartridge.

In some embodiments, the transferring element-unit coupler-unit assembly is arranged such that the three elements are linearly aligned with respect to each other. In an example, the cartridge is substantially rounded, and the three elements are aligned along an extension of a radial axis of the cartridge. In some embodiments, movement of the transferring element is also performed along the same linear path. In an example, the cartridge is substantially linear, and the three elements are aligned perpendicularly to a long axis of the cartridge. In some embodiments, movement of the transferring element is also performed along the same linear path. A potential advantage of an arrangement in which the pulling/pushing elements and the unit are linearly aligned with respect to each other may include simplifying the mechanical operation of the assembly, reducing a risk of breakage, and facilitating detection of a current status of the assembly during operation, for example in order to differentiate between a complete course of movement and a deficient one.

Additionally or alternatively, in some embodiments, the unit coupler may be configured for moving units in a manner that is different than linear pulling and pushing, for example, the unit coupler may be pivotable such that it rotates in and out of a plane, optionally carrying an attached source material unit along with it.

In some embodiments, the transferring element is comprised of a slider which moves on a shaft, pulling the unit coupler (and in turn, the source material unit) along with it. In some embodiments, a distal head of the slider is shaped and/or sized to fit by interference to a proximal portion of the unit coupler. In some embodiments, the distal head of the slider comprises a curvature and/or one or more slanted faces shaped to guide the cartridge during loading, optionally assisting in leading the cartridge to a final (and optionally locked) position relative to the inhaler.

In some embodiments, the slider is actuated by a motorized screw, which upon rotation moves the slider proximally or distally (depending on the rotation direction) on a shaft. Movement of the slider on the shaft leads the attached source material unit (attached via the unit coupler) the use-position.

An aspect of some embodiments of the invention relates to a cartridge for use with an inhaler, the cartridge being formed with an outwardly extending bulge positioned to assist in alignment of the cartridge with respect to a designated cavity in the inhaler. In some embodiments, during loading of the cartridge onto the inhaler the bulge is seated within a designated groove in the inhaler cavity, and upon rotation of the cartridge the bulge is moved to an angular position in which one or more elements from within the bulge (e.g. the unit coupler) are aligned with one or more elements of the inhaler (e.g. the transferring element) to engage them. Optionally, rotation of the cartridge intervenes the aligned elements, resulting in locking of the cartridge with respect to the inhaler.

In some embodiments, the bulge breaks an otherwise symmetric cross section profile of the cartridge and may therefore facilitate an initial placement of the cartridge in the inhaler cavity and potentially reduce the time and effort needed to load the cartridge for use.

In some embodiments, the unit coupler of the cartridge extends at least in part into the bulge. Optionally, when the unit coupler is moved with respect to a passageway of the bulge (such as when the unit coupler is pulled in the direction of the inhaler), the passageway (defined between two opposing walls of the bulge) is exposed to allow pulling (or returning) of the source material unit through. In some embodiments, the passageway is only wide enough to allow passing of a single source material unit through. Some potential advantages of a cartridge comprising a bulge structured so that a passageway leading into and out from the cartridge is limited in size (and at least a part of the time blocked by the unit coupler) may include reducing a risk of contamination of the source material units within the cartridge; reducing the amount of dust or other debris that may enter the cartridge; reducing entry of airflow toward the source material unit which may cause undesired evaporation; reducing a risk of misuse or violation.

An aspect of some embodiments relates to a source material cartridge for use with an inhaler, the cartridge comprising one or more safety locks which prevent use of the source material units within the cartridge if the cartridge is not operably attached to the inhaler. In some embodiments, a safety lock comprises a restricting frame that is aligned with the unit coupler in a manner that prevents movement of the unit coupler out from the cartridge. In some embodiments, upon positioning of the cartridge in a designated cavity and/or upon orienting the cartridge with respect to the cavity (e.g. rotating), the restricting frame is moved to a different alignment relative to the unit coupler, allowing the unit coupler to pass through. Another safety lock may include a stopper which when active prevents internal movement of the source material units in the cartridge, for example preventing internal rotation of the units by interfering with the course of movement. Optionally, the stopper is released during positioning of the cartridge in the inhaler cavity, for example by closing of a cover door over the cartridge.

An aspect of some embodiments relates to a source material cartridge for use with an inhaler, the cartridge configured to indicate to the inhaler, for example via structural variations in the cartridge, that all source material units have been used. Optionally, the last 10%, the last 20%, the last 5% of the units of the cartridge or the last unit or two comprise an indicator for signifying that the cartridge had been fully used. In some embodiments, the indicator is a structural variation in the source material unit, the cartridge housing, and/or in a slot in which the source material unit is positioned. Examples of structural variations include source material units that are arranged in slots of a carousel, with the last slot (or several slots) in the carousel remaining empty (do not contain a source material unit). In another example, the structural variation includes a cartridge (positioned last or at a predetermined location with respect to the last slot) that does not contain source material, for example comprising only a frame of the unit. In another example, the structural variation includes a cartridge that does not comprise an electrically conductive member. In some embodiments, the structural variation comprises neither an electrically conductive member nor source material. In some embodiments two or more different or the same structural variations are used in the same cartridge, for example in the last 2 or 3 slots. Optionally, the structural variations mechanically and/or electrically affect the process of pulling and/or otherwise using the source material unit.

An aspect of some embodiments relates to a rotatable source material cartridge which is limited in rotation in order to prevent access to source material units of the cartridge that were already used. In some embodiments, rotation is limited to 360 degrees, 180 degrees, 90 degrees or intermediate, larger or smaller angles. The cartridge may be rotatable clockwise and/or counterclockwise.

An aspect of some embodiments relates to a source material cartridge for use with an inhaler, the cartridge comprising an identification tag such as an RFID tag which is readable and writable. In some embodiments, information written on the RFID tag, identifies the cartridge as being authorized for use with the inhaler. In some embodiments, the RFID tag comprises data relating to prior usage of source material from the cartridge, for example: the number of source material units that were used, the specific source material units that were used, the type of source material used, the date or time in which the last unit of source material was used, and/or other usage related data.

In some embodiments, the inhaler is configured to detect and/or keep track of the progress of use of the cartridge. In some embodiments, the inhaler controller is programmed to count or index the number of source material units used and/or the number of source material units still available for use. Additionally or alternatively, an internal memory keeps track of the units. Additionally or alternatively, the inhaler (for example via the controller) communicates with an external memory or database, for example a cloud-based memory for keeping track of cartridge usage.

In some embodiments, the source material units and/or cartridge slots in which they are positioned comprise an identification marking. Optionally, data indicative of the identification marking is obtainable through an RFID tag associated with the cartridge.

An aspect of some embodiments relates to a kit comprising an inhaler and a source material cartridge for use with the inhaler, the cartridge comprising an identification tag such as an RFID tag which is readable and/or writable by the inhaler. In some embodiments, according to the information on the RFID tag, the inhaler identifies that a proper cartridge was inserted for use. In some embodiments, the inhaler is configured to write to the RFID tag data related to usage of the source material from the cartridge, for example: the number of source material units that were used, the specific source material units that were used, the type of source material used, the date or time in which the last unit of source material was used, and/or other usage related data.

As referred to herein, an "indicator" ,"indication slot", "indication unit" may include one or more of: an empty slot (a slot that does not contain source material, or a space formed in between adjacent source material unit); a unit that comprises a different structure and/or shape, for example, a unit that does not include an electrically conductive member; a unit that is shaped differently from at least 55%, at least 70%, at least 85% or intermediate, larger or smaller percentage of the total number of units in the cartridge; a unit that is shaped differently from the majority of source material units in the cartridge; a unit having a construction different from "standard" source material units being pulled into use in the cartridge. An "indicator", "indication slot", "indication unit" may or may not be filled with source material.

In some embodiments, the "indicator", "indication slot", "indication unit" is identifiable by a sensor. Optionally, the sensor is a mechanical sensor. Optionally, the sensor is an electrical sensor, such as a sensor that detects a different or no electrical resistance upon contacting the indicator. Optionally, the sensor is an optical sensor, such as a light based sensor which detects a different color of the indicator, a lack of color (e.g. when an empty slot is used), and/or other.

Additionally or alternatively, the "indicator", "indication slot", "indication unit" is recognizable by a controller of the system, for example based on a pre-defined position of the indicator. Optionally, pre-defined positions of indicators in the cartridge are coded onto the cartridge itself (e.g. on an RFID tag) and/or otherwise programmed into the system.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1:
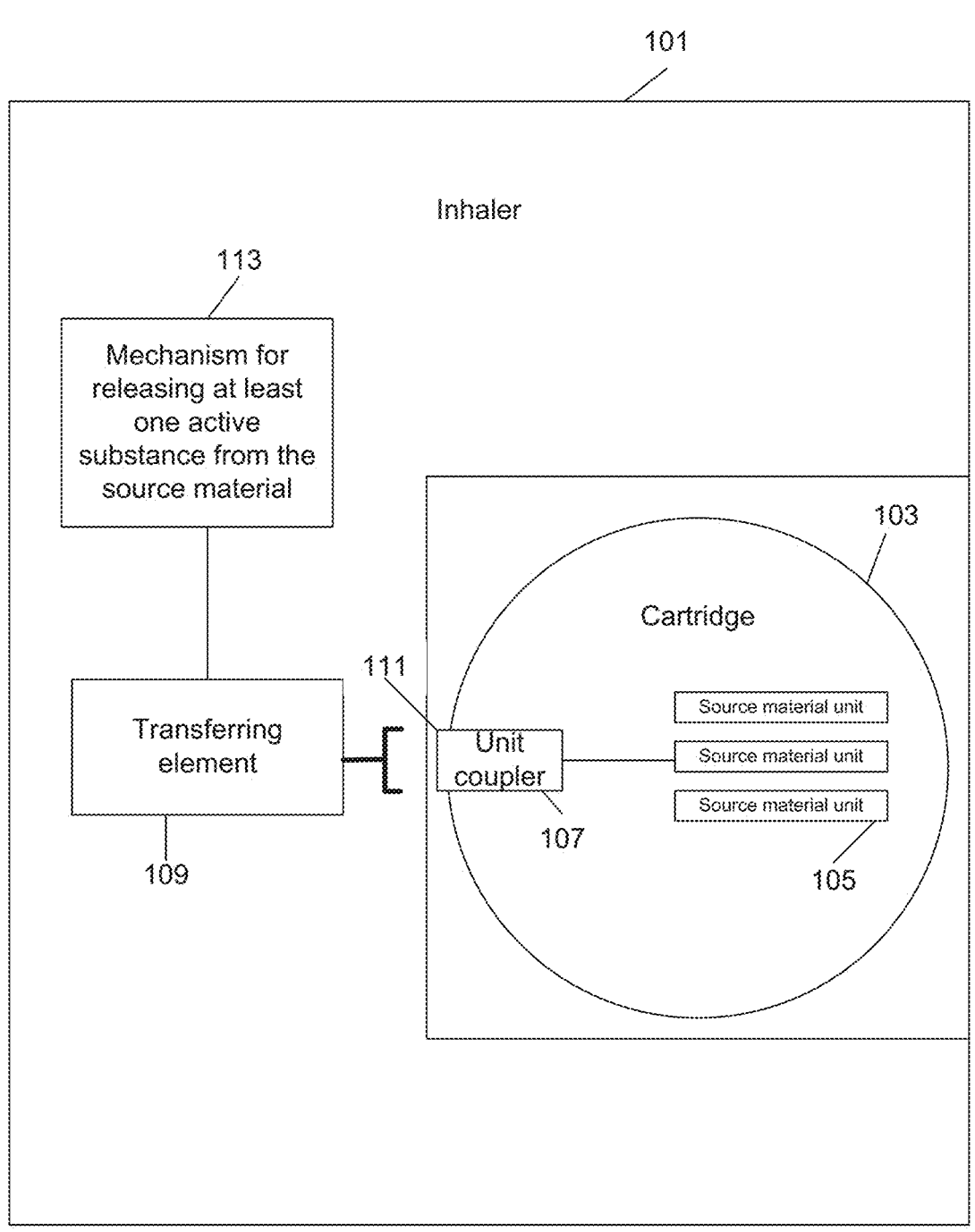
FIG. 1 is a block diagram of a system of a system comprising an inhaler and a cartridge containing a plurality of source material units, according to some embodiments.

Referring now to the drawings, FIG. 1 is a block diagram of a system comprising an inhaler 101 configured to receive and/or otherwise attach to a cartridge 103 containing a plurality of source material units 105. The inhaler 101 is depicted with a cartridge 103. In some embodiments, cartridge 103 comprises a unit coupler 107, configured to couple between a source material unit 105 from within the cartridge and a transferring element 109 of the inhaler.

During operation, in accordance with some embodiments, transferring element 109 engages unit coupler 107 to pull, move, or otherwise actuate movement of a unit 105 into a use-position within the inhaler device. In some embodiments, at least one active substance is released from the unit 105 by a release mechanism 113. In some embodiments, the release mechanism comprises placing the unit in communication with an airflow tract, for example so that flow of air is allowed to flow to and through the source material in the unit. In some embodiments, the release mechanism comprises engaging the unit with electrical contacts (e.g. electrodes) for actuating heating of the source material. Optionally, the unit is carried to a position in which it is clamped within an airflow tract of the inhaler while the source material contained within it is heated to be vaporized.

In some embodiments, following use of a unit 105, the unit is returned to the cartridge by the unit coupler and transferring element assembly. Optionally, the unit coupler and transferring element remain attached to each other while an advancing mechanism of the units in the cartridge is actuated (manually and/or automatically), moving a source material unit (optionally a subsequent one) into a position in which it engages unit coupler 107. In some embodiments, a subsequent unit can be engaged by the unit coupler only when the unit coupler has been at least partially returned into the cartridge (e.g. at least partially returned into the cartridge housing). In some embodiments, the unit coupler is returned into the cartridge to an extent which is set by a relative position of the returned unit. For example, the unit coupler reaches a "complete stop" when the source material unit is advanced into the cartridge a predefined limit, for example until encountering an inner wall of the cartridge housing. Optionally, the unit coupler is fully received within the cartridge housing when returned. In some embodiments, the unit coupler and the transferring element remain attached to each other for as long as the cartridge is functionally coupled to the inhaler. In some embodiments, upon removal of the cartridge (for example when all source material units have been fully used), the transferring element detaches from the unit coupler, and the cartridge can be removed or replaced by a new cartridge. A potential advantage of enabling use of source material units only when the transferring element of the inhaler is coupled to the unit coupler of the cartridge may include reducing a risk of undesired use, and/or violation, for example preventing the ability to manually pick a unit (such as from a broken cartridge) and place it for use in the inhaler. Another potential advantage may include providing a visual distinction between different cartridges, such as cartridges containing different source materials, for example via unit couplers that are colored in different colors.

In some embodiments, unit coupler 107 is shaped and/or sized and/or positioned such that it defines a bulge 111 on the external housing of cartridge 103. In the example shown herein, the cartridge housing is substantially rounded (for example, disc shaped) and the unit coupler extends radially outwardly from the perimeter, forming a protrusion relative to the rounded housing.

In some embodiments, bulge 111 defined by unit coupler 107 facilitates alignment of the cartridge upon attachment to the inhaler, as it stands out relative to the cartridge to be engaged by the transferring element of the inhaler.

In some embodiments, having unit coupler 107 positioned (at least in part) at the cartridge opening through which the source material units are passed reduces the amount of airflow, dust, debris and/or other contamination that may enter the cartridge, thus protecting the source material units from damage. Additionally, or alternatively, having unit coupler 107 positioned (at least in part) at the cartridge opening may reduce or prevent movement of air along the source material unit, thus reducing evaporation and loss of volatile substances from the source material.

Some embodiments may include a mechanism for breaking the unit coupler or otherwise limiting the unit coupler function, implemented for example following use of the last source material unit in the cartridge, so as to prevent or impede future use of an empty cartridge. In some embodiments, cartridge 103 comprises multiple source material units, for example 5, 10, 50, 60, 75, 70, 100, 200 or intermediate, larger or smaller amount of source material units. Optionally, the units are arranged in a serial manner. In some embodiments, the units are aligned along a carousel or disc like structure and are rotated so that at each turn a different unit engages the unit coupler. Alternative structures may include a linear cartridge in which the units are stacked one on top of the other, or one aligned adjacent the other.

In some embodiments, unit 105 comprises one or more source materials, from which one or more active substances are released by heating of the source material. In some embodiments, the source material comprises plant matter. In some embodiments, the material comprises at least one botanical substance selected from the group consisting of: *Cannabis sativa, Cannabis indica, Cannabis ruderalis, Acacia* spp., *Amanita muscaria,* Yage, *Atropa belladonna, Areca catechu, Brugmansia* spp., *Brunfelsia latifolia, Desmanthus illinoensis, Banisteriopsis caapi, Trichocereus* spp., *Theobroma cacao, Capsicum* spp., *Cestrum* spp., *Erythroxylum coca, Solenostemon scutellarioides, Arundo donax, Coffea*

*arabica, Datura* spp., *Desfontainia* spp., *Diplopterys cabrerana, Ephedra sinica, Claviceps purpurea, Paullinia cupana, Argyreia nervosa, Hyoscyamus niger, Tabernanthe iboga, Lagochilus inebriens, Justicia pectoralis, Sceletium tortuosum, Piper methysticum, Catha edulis, Mitragyna speciosa, Leonotis leonurus, Nymphaea* spp., *Nelumbo* spp., *Sophora secundiflora, Mucuna pruriens, Mandragora officinarum, Mimosa tenuiflora, Ipomoea violacea, Psilocybe* spp., *Panaeolus* spp., *Myristica fragrans, Turbina corymbosa, Passiflora incarnata, Lophophora williamsii, Phalaris* spp., *Duboisia hopwoodii, Papaver somniferum, Psychotria viridis,* spp., *Salvia divinorum, Combretum quadrangulare, Trichocereus pachanoi, Heimia salicifolia, Stipa robusta, Solandra* spp., *Hypericum perforatum, Peganum harmala, Tabernaemontana* spp., *Camellia sinensis, Nicotiana tabacum, Nicotiana rustica, Virola theidora, Voacanga africana, Lactuca virosa, Artemisia absinthium, Ilex paraguariensis, Anadenanthera* spp., *Corynanthe yohimbe, Calea zacatechichi, Coffea* spp. (*Rubiaceae*), *Sapindaceae* spp., *Camellia* spp., *Malvaceae* spp., *Aquifoliaceae* spp., *Hoodia* spp. *Chamomilla recutita, Passiflora incarnate, Camellia sinensis, Mentha piperita, Mentha spicata, Rubus idaeus, Eucalyptus globulus, Lavandula officinalis, Thymus vulgaris, Melissa officinalis,* Tobacco, Aloe Vera, Angelica, Anise, Ayahuasca (*Banisteriopsis caapi*), Barberry, Black Horehound, Blue Lotus, Burdock, Camomille/Chamomile, Caraway, Cat's Claw, Clove, Comfrey, Corn Silk, Couch Grass, Damiana, Damiana, Dandelion, Ephedra, Eucalyptus, Evening Primrose, Fennel, Feverfew, Fringe Tree, Garlic, Ginger, Ginkgo, Ginseng, Goldenrod, Goldenseal, Gotu Kola, Green Tea, Guarana, Hawthorn, Hops, Horsetail, Hyssop, Kola Nut, Kratom, Lavender, Lemon Balm, Licorice, Lion's Tail (Wild Dagga), Maca Root, Marshmallow, Meadowsweet, Milk Thistle, Motherwort, Passion Flower, Passionflower, Peppermint, Prickly Poppy, Purslane, Raspberry Leaf, Red Poppy, Sage, Saw Palmetto, Sida Cordifolia, Sinicuichi (Mayan Sun Opener), Spearmint, Sweet Flag, Syrian Rue (*Peganum harmala*), Thyme, Turmeric, Valerian, Wild Yam, Wormwood, Yarrow, Yerba Mate, and Yohimbe, and any part and any combination thereof.

Examples of the active substances released from the source material may include, without being limited to: Δ9-tetrahydrocannabinol (THC), cannabidiol (CBD), cannabigerols (CBG), cannabichromenes (CBC), cannabinol (CBN), cannabinodiol (CBDL), cannabicyclol (CBL), cannabielsoin (CBE), cannabidivarin (CBDV), tetrahydrocannabivarin (THCV) and cannabitriol (CBT), and/or corresponding cannabinoid acids that form such active substances upon decarboxylation.

In some embodiments, unit 105 comprises a material (for example, a botanical substance) carrying at least one active substance, and optionally includes additional elements for the transport, mechanical stabilization, and/or volatilization or vaporization (by heating, for example) of the active substance. In some embodiments, a unit comprises active substance material for delivering to an inhaling user over a selected number of inhalations via the inhaler, for example over no more than, 1, 2, 3, 4, 7, 10 inhalations or intermediate, larger or smaller amount. In some embodiments, unit 105 comprises a single drug dose for pulmonary delivering to a patient using the inhaler.

In some embodiments, the source material is arranged within the source material unit 105 in flattened form. Optionally, the source material is arranged such that air can be drawn or otherwise passed through material for extraction of the active substance. In some embodiments, the material is arranged as a pallet comprising, for example, a flattened expanse of porous or friable material thin enough to permit airflow through and between the two largest faces.

In an example, the unit comprises a pallet of source material held in between opposing mesh structures. Source material units as described in U.S. Pat. No. 9,802,011 by the present assignees which is incorporated herein by reference are also contemplated by this application. (See reference to "dose cartridge" as an equivalent to a source material unit).

FIG. 2 is a flowchart of a general method of using an inhaler configured to be operably coupled to a cartridge including a plurality of source material units and a unit coupler, according to some embodiments.

In some embodiments, a cartridge comprising a plurality of source material units and a unit coupler is loaded onto the inhaler (201). Optionally, the cartridge is received within a designated aperture, cavity or recess in the inhaler body. Alternatively, the cartridge operably attaches to the inhaler body so that at least the unit coupler is accessible by one or more elements of the inhaler, such as a transferring element.

In some embodiments, loading of the cartridge (and/or otherwise inserting or attaching) simultaneously drives movement of a transferring element of the inhaler, which engages the unit coupler in the cartridge. The unit coupler, in turn, is already coupled to a source material unit in the cartridge (for example coupled to a first unit in the series) and the transferring element-unit coupler-unit assembly is brought to a ready-to-pull position. In some embodiments, the cartridge fits into place by an interlocking mechanism, which further actuates attachment of the transferring element of the inhaler to the unit coupler of the cartridge. A potential advantage of cartridge loading that automatically initiates engagement of the source material unit to have it ready for use may include saving time and efforts to a user of the inhaler.

In some embodiments, the inhaler is activated to use a source material unit, the unit being accessible via the unit coupler (203), optionally only via the unit coupler. Optionally, the unit is pulled into a body of the inhaler by the transferring element-unit coupler assembly. In some embodiments, the source material units cannot be accessed to be moved into use (e.g. pulled) without being engaged to the unit coupler. This may prevent undesired use, limit excessive use, and ensure that the cartridge may be used only with a designated inhaler. Optionally, the unit coupler is structured such that it is configured to attach, interlock, or otherwise connect only to a matching transferring element of the inhaler.

In some embodiments, optionally following use of a first source material unit, advancement of the cartridge is actuated to enable use of a second source material unit (205). In some embodiments, the second unit is accessible only when the unit coupler or at least a portion of the unit coupler was returned into the cartridge, such as into a lumen defined by the cartridge housing. Optionally, a used source material unit is returned to its original position in the cartridge. Alternatively, the used source material unit is returned to a different slot in the same cartridge or to a different cartridge. In some embodiments, advancement of the cartridge moves a second unit to be in contact with the unit coupler. Optionally the transferring element remains attached to the unit coupler so that once the transferring element-unit coupler-unit are inline, the second unit can be transferred (e.g. pulled) in for use.

In some embodiments, cartridge advancement is carried out by internal movement of the source material units in the cartridge, such as rotation. In some embodiments, one or more units can be skipped (jumped over) during cartridge advancement, to reach a source material unit other than the subsequent unit. In some embodiments, rotation and/or skipping may be performed in one or more directions so as to elect specific source material units based for example on their content and/or their prior use.

In some embodiments, rotation of the source material units in the cartridge and/or rotation of the cartridge as a whole (e.g. including the cartridge housing) is actuated by a one or more gears. In an example, one or more rotating gears are configured within the inhaler housing at a position suitable for engaging the cartridge when inserted into the cavity.

In some embodiments, cartridge advancement is controlled by a controller of the inhaler. Optionally, cartridge advancement is controlled according to the content of the source material units in the cartridge and/or their prior use, for example, the controller is programmed to actuate advancement such that one or more units are skipped and optionally that no units are used more than once. In some embodiments, units in the cartridge may include different source materials and/or different concentrations of active substances and/or different amounts of source material. Optionally, the controller controls advancement of the units in the cartridge according to a predefined regimen selected for the user. Optionally the controller selects a used unit for use according to the amount of active material remaining in the unit and/or the amount already extracted therefrom.

FIG. 3 is a cross section view of a mechanism for engaging a source material unit contained in a cartridge in order to transfer the unit to a use-position, according to some embodiments.

In some embodiments, a unit coupler 301 couples between a source material unit 303 and a transferring element, in this example in the form of a pull-out slider 305. In some embodiments, the unit coupler comprises a distal portion 307 shaped and/or sized to engage unit 303, and a proximal portion 309 shaped and/or sized to engage slider 305. Optionally, the unit coupler and the unit are coupled via geometric portions that intervene with each other, for example including a recess defined in one of the elements and a respectively shaped protrusion on the other element. Optionally, the unit coupler and the slider are coupled via geometric portions that intervene with each other, for example including a recess defined in one of the elements and a respectively shaped protrusion on the other element.

In some embodiments, as can be observed for example in the detailed view of FIG. 4A, distal portion 307 of unit coupler 301 is situated within a connecting portion of unit 303, in this example being shaped as latch mandibles. A proximal portion 309 of the unit coupler fits onto a distal head 311 of the slider 305. In this example, proximal portion 309 of the unit coupler is shaped as a frame with a rectangular cross section, having an opening 325 in which distal head 311 of the slider is slidably received. In some embodiments, distal head 311 is substantially T-shaped. In some embodiments, opening 325 is shaped and sized to receive the T-shaped head of the slider. A potential advantage of a T-shaped head may include obtaining a strong grasp of the unit coupler, facilitating its pulling and/or pushing.

In some embodiments, for example as shown in FIG. 4B, distal head 311 of the slider comprises one or more slanted faces. In some embodiments, distal head 311 includes a major slanted face 313 that is angled to facilitate cartridge insertion, enabling at least some degree of movement while placing the cartridge relative to the inhaler. In some embodiments, slanted face 313 assists in guiding the cartridge into a final position with respect to the inhaler cavity in which it is received. Optionally, slider distal head 311 is formed with a curvature that is selected to reduce interference with cartridge insertion. In some embodiments, distal head 311 includes one or more minor slanted faces 315 that are angled to facilitate fitting of unit coupler 301 onto distal head 311 of the slider upon rotation of the cartridge relative to the inhaler, for example so as to guide the cartridge into a locked position.

Going back to FIG. 3, movement of slider 305 is actuated, in some embodiments, by a shaft and screw assembly. In operation, screw 319 is rotated (e.g. by a motor, a set of gears, and/or other electromechanical or purely mechanical actuation means), driving movement of body 321 of the slider 305 to slide in a proximal direction or in a distal direction (depending on the direction of rotation) on shaft 323. As the slider moves distally or proximally on the shaft, it carries unit coupler 301 along with it, which in turn carries the source material unit 303.

In some embodiments, body 321 of slider 305 comprises a groove 327 (see FIG. 4C) through which shaft 323 extends. Optionally, the groove prevents the slider from rotating when moving distally or proximally, for example rotating around its long axis.

It is noted that the unit transfer mechanism defined hereinabove is provided as an example and that other mechanisms may be used, for example: a pulley, magnet based actuation, manual movement of the slider, spring based actuation and/or other mechanisms configured for moving the source material unit from the cartridge to a position in which at least one active substance can be released from the source material contained within the unit.

In some embodiments, the unit coupler 301 is formed with one or more indentations 329. Optionally, a restricting frame (shown in part at 331) is shaped to fit within indentations 329 to prevent the unit coupler from moving (for example before the cartridge is operably attached to the inhaler).

FIGS. 5A-B are a cross sectional view of a mechanism for example as shown in FIG. 3, and an isometric view of the unit coupler, according to some embodiments. FIG. 5A further shows the cartridge housing 501, when the cartridge is seated at a designated cavity (not shown in this figure) of the inhaler. As can be observed, in some embodiments the unit coupler 301 extends from within housing 501 in a proximal direction, at least a portion of the unit coupler being positioned outside a perimeter defined by the housing (in this example, a rounded perimeter). Optionally, at least a portion of the unit coupler is situated within a bulge of the cartridge.

As can be further observed, in some embodiments at least a portion of slider 305 such as distal head 311 enters the bulge of the cartridge when engaged with unit coupler 301. Optionally, slider 305 (or generally any transferring element) is limited in movement and/or is short enough so that it does not at all extend into the cartridge or does not extend further than the lumen of the bulge. A potential advantage of limiting the extent of reach of the transferring element may include reducing a risk of mechanical damage, reducing a risk of contamination within the cartridge, and/or reducing a risk of misuse.

FIG. 5B further shows unit coupler 301 attached to source material unit 303.

FIGS. 6A1-B3 are a side view (6A1, 6A2, 6A3) and an isometric view (6B1, 6B2, 6B3) of the process of positioning and optionally locking a cartridge including a unit coupler in position with respect to the inhaler, according to some embodiments.

In some embodiments, the cartridge is placed within a designated cavity or recess formed in the inhaler. Optionally, the cartridge is moved to a locked positioned with respect to the inhaler. In some embodiments, the cartridge is locked via rotation, linear movement, by pushing down, by sliding, and/or by magnetic attraction.

In the example shown herein (see 6A1 and 6B1), a carousel-type cartridge 601 is first situated with respect to the inhaler such that the bulge 603 of the cartridge (into which unit coupler 605 extends from within) is set adjacent but not yet in contact with the pull-out slider 607. Optionally, distal head 609 is aligned with an opening 619 of the unit coupler along a perimeter of the cartridge housing.

In some embodiments, by setting the angular position of the cartridge, for example rotating the cartridge clockwise as shown in FIGS. 6A2 and 6B2, unit coupler 605 is advanced to a position in which it connects to the slider 607. In the example shown herein, distal head 609 of the slider is received within a respective geometry of the unit coupler, such as within a frame 613.

In some embodiments, movement (e.g. rotation, lifting, sideways movement) of the cartridge relative to the inhaler is limited. In an example, cartridge rotation may be stopped by wall 621 of the bulge 603 upon encountering distal head 609 of the slider. Additionally or alternatively, cartridge rotation is set by a curvature of the inhaler recess or cavity in which the cartridge is seated, and/or by a snap fit mechanism.

In some embodiments, at the final position, shown for example in FIGS. 6A3 and 6B3, the cartridge is interlocked with the inhaler, and the slider, unit coupler, and one of the source material units 615 are linearly aligned with respect to each other, for example along a radial axis 617 of the cartridge.

In some embodiments, the unit coupler and the slider remain connected to each other during the rest of the use of the cartridge, and are disconnected upon removal of the cartridge away from the inhaler (e.g. by rotating the cartridge in a reverse direction).

In some embodiments, the carousel of source material units of the cartridge is configured to be rotated clockwise and/or counter clockwise, so as to advance from one unit to another. In some embodiments, source material units are pulled for use in a serial manner. Alternatively, source material units are pulled for use in a different order.

In some embodiments, cartridge rotation (clockwise or counterclockwise) is limited. In some embodiments, cartridge rotation is limited to an extent set by the first source material unit of the cartridge, so that rotation passed a location of the first unit is restricted. In some embodiments, cartridge rotation in each direction is limited to a maximum of 360 degrees. In other embodiments, cartridge rotation may be limited to 180 degrees, 90 degrees, or intermediate, larger or smaller rotational angle. A potential advantage of limiting rotation of the cartridge to a full circle but no more may include avoiding inadvertent access to source material units that were already used.

FIGS. 7A-C illustrate a process of pulling a source material unit from the cartridge, according to some embodiments.

In FIG. 7A, slider 701 is at a distalmost position with respect to shaft 703, while a distal head 705 (see 7B) of the slider engages unit coupler 707 (see 7B) within the bulge 709 of cartridge 711. In FIG. 7B, slider 701 is at a midway position with respect to shaft 703, pulling unit coupler 707 along with it as well as a source material unit 721 which is coupled to the unit coupler and removed outwardly from the cartridge. In some embodiments, as shown in this example, movement of slider is actuated by rotation of a screw 713 (see also FIG. 3). In FIG. 7C, unit 721 has fully exited the cartridge, and slider 701 is at its most proximal position with respect to shaft 703.

In some embodiments, a passageway 715 is defined between opposing walls 717 of the bulge 709. Optionally, passageway 715 is wide enough to allow the source material unit 721 to slidably pass through. In some embodiments, dimensions (e.g. a width) of passageway 715 are selected according to a thickness of unit 721, for example so as to allow only one unit at a time to pass through. Some potential advantages of a limited passageway may include reducing a risk malfunction (for example undesired pulling of more than unit); reducing exposure of the contents of the cartridge to the external conditions, such as humidity; reducing exposure of the contents of the cartridge to contamination and debris; and aligning of the source material unit relative to a designated slot in the inhaler and/or in the cartridge, so that the unit can be easily pulled or pushed into the designated slot. In some embodiments, opposing walls of the bulge are shaped to allow passage of a T-shaped element, such as a T-shaped distal head of the transferring element.

FIGS. 8A-B are an illustration of a cartridge comprising a bulge (8A) and a detailed view of the bulge showing the unit coupler (8B), according to some embodiments. In some embodiments, cartridge 801 comprises a bulge 803, projecting from an external surface of the cartridge. Optionally, at least a part of a unit coupler 805 located inside the cartridge extends within the bulge (see enlarged view of FIG. 8B). In some embodiments, unit coupler 805 is formed with tail protrusions 825 at its proximal face. Optionally, when the cartridge is placed in the inhaler cavity and then rotated to a final use-position, tail protrusions 825 slide within respective grooves formed in the walls of the inhaler cavity, guiding the cartridge into the final position.

In some embodiments, bulge 803 is positioned, shaped and/or sized to assist in aligning the cartridge with respect to a designated recess of the inhaler device (not shown herein). Optionally, bulge 803 extends to a distance 811 of between 1, 3, 5, 10, 20 mm or intermediate, longer or shorter distances relative to the external perimeter of the cartridge housing. Optionally, bulge 803 extends to a radial distance 813 of between 5, 10, 20, 50, 80 mm or intermediate, longer or shorter distances from a center of the cartridge.

In some embodiments, cartridge 801 includes a window 807 for indicating the progress of use, for example showing a number of the source material unit that is currently coupled to the unit coupler. In some embodiments, cartridge 801 is formed with a central aperture 809. Optionally, during insertion, aperture 809 is threaded over a pin or other structure (not shown in this figure) suitable for threading of the aperture onto it, for facilitating positioning of the cartridge. In some embodiments, for example upon closing a cover door of the inhaler (not shown herein) after the cartridge is in place, the pin engages or otherwise actuates a rotation driving mechanism which sets internal rotation of the source material units in the cartridge, optionally positioning a different unit in contact with the unit coupler at each turn.

In some embodiments, the cartridge is substantially rounded but not circular. In this example, cartridge 801 includes a first portion 817 having a first radius, and a second portion 819 having a different radius. A potential advantage of a cartridge comprising an asymmetric profile may include facilitating alignment of the cartridge relative to the inhaler cavity during insertion.

In some embodiments, the cartridge comprises an identification tag, such as an RFID tag. In some embodiments, the identification tag includes data regarding the cartridge, for example: the number of source material units in the cartridge; the type(s) of source material; the types of active substance(s); the amount of active substance; which source material(s) are contained in each source material unit (if, for example, different units in the cartridge contain different source materials); the location of each source material unit within the cartridge; manufacturing date; expiration date; batch information, use information and/or other cartridge related data. In some embodiments, the inhaler comprises or is associated with an RFID reader/writer. In some embodiments, the RFID reader/writer identifies the cartridge upon its loading. In some embodiments, the RFID reader/writer is programmed to write data to the tag of the cartridge, for example: the amount of source material units that have been used from the cartridge; the numbering and/or location of the source material units used (in an example, the units are serially numbered according to their respective location in the cartridge, but can be used in any order); the amount of active substance that was extracted and/or remained in each used unit; and/or other cartridge usage related data.

FIGS. 9A-B are illustrations of an inhaler including a cartridge for example as shown in FIGS. 8A-B in an initially inserted position (FIG. 9A) and in a final (optionally locked) position (FIG. 9B), according to some embodiments.

In some embodiments, inhaler 901 comprises a cavity 903 for receiving a cartridge, for example cartridge 801 as shown in FIG. 8A-B. In some embodiments, the inhaler comprises a cover door 905 that can be opened and closed to place or remove a cartridge. In some embodiments, the cover door 905 is shaped to slightly move the cartridge, for example pushing it during closure to a final position with respect to the inhaler cavity. Optionally, the cover door comprises a lock that prevents opening of the cover door if the unit coupler has not returned to its distalmost position.

In FIG. 9A the cartridge is shown seated within the cavity upon initial insertion. Optionally, at this position, the source material units inside the cartridge cannot be accessed for use. In FIG. 9B, the cartridge is turned into a locked position relative to inhaler, thereby aligning the unit coupler, slider and one of the source units relative to each other. The aligned elements enable pulling of the unit into the inhaler to release at least one active substance from the source material and deliver it to an inhaling user; and/or pushing of the used unit back into the cartridge. (It is noted that a mouthpiece of the inhaler is not shown in this figure).

FIGS. 10A-C are different views of an inhaler cavity in which a source material cartridge is received, according to some embodiments. In some embodiments, cavity 1001 comprises a curvature which matches a curvature of the cartridge. Optionally, the curvature is asymmetric. An asymmetric curvature may assist in orienting the cartridge with respect to the cavity. Alternatively, the curvature is symmetric.

In some embodiments, cavity 1001 includes an indentation 1003 in which a bulge of the cartridge is seated. In some embodiments, (see detailed view of FIG. 10B), a distal head 1005 of a transferring element of the inhaler protrudes into the space of the cavity, adjacent the indentation. Optionally, the distal head 1005 is positioned such that when a cartridge is first seated in cavity 1001, no engagement is made with the distal head 1005; once the cartridge is turned (in this example—about 1-10-20-45-90 degrees Clockwise) the distal head slidably fits within a matching geometry of the unit coupler of the cartridge. In some embodiments, the distal head 1005 is positioned with respect to the cartridge housing such that even rotation of the cartridge in the inhaler cavity does not break or otherwise damage the distal head. Optionally, upon initial placement of the cartridge in the cavity, the distal head only slightly contacts the cartridge housing; then, when the cartridge is rotated to a final position, the unit coupler is rotated along with it until it receives the distal head of the slider. A potential advantage of such structure is that even at the slider's distalmost position, in which it extends outwardly from the inhaler housing to reach out to the cartridge, it is not at a risk of breakage and/or other deformation which may occur during loading of the cartridge (especially manual loading of the cartridge by a user, which is harder to control).

In some embodiments, cavity 1001 comprises a central protruding element 1007, for example a pin or a thread, onto which respective aperture of the cartridge can be positioned. Optionally, the central protruding element comprises fins 1015 for driving internal rotation of the source material units in the cartridge, once the cartridge is seated in the inhaler cavity.

In some embodiments, cavity 1001 comprises a bump 1009, optionally located on a side wall of the cavity. In some embodiments, upon rotation of the cartridge from its original seating in the cavity to the final orientation, in which the cartridge is operably attached to the inhaler, bump 1009 is contacted by the cartridge housing and produces a "click" sound for indicating to a user that the cartridge has reached its final position and no additional rotation is required.

FIGS. 11A-B show a restricting frame and a movement stopper of the cartridge, in a locked position (11A) and a released position (11B), according to some embodiments.

In some embodiments, the cartridge houses a restricting frame 1101 that is mechanically transformed from a locked position, in which the unit coupler 1103 is prevented from moving, to a released position, in which the unit coupler can be moved along an extension of the radial axis to be pulled from (or pushed back) into the cartridge.

In some embodiments, the restricting frame is released gradually. Optionally, different steps of the cartridge loading process actuate release of different locks of the frame.

In an example, compression of a spring 1105, for example upon placing the cartridge in the inhaler cavity, releases portion 1107 of the frame, allowing it to bounce upwards, thereby releasing portion 1109 of the frame (that was clamped in place by finger 1111 of portion 1107). Optionally, upon release of portion 1109, portion 1109 is free to slide sideways so that an opening 1113 defined in portion 1109 is aligned with the unit coupler 1103. Opening 1113 is shaped so that the unit coupler can be pulled or pushed through it.

In some embodiments, the cartridge comprises a stopper that limits internal movement (e.g. rotation) of the source material units. In some embodiments, the stopper is released by closure of a cover door of the inhaler over the cartridge. In an example, by compression of a spring 1115 (such as by closure of the cover door, not shown herein), releases a pivoting door 1117. In some embodiments, pivoting door 1117 is coupled to a stopping element such as teeth 1119 (see FIG. 11C) so that upon release of the door, teeth 1119 move from a position in which they interfered with rotation of the source material units (e.g. by being placed in between the units), to a rotation in which they are aligned with a geometric spacing 1121 of the units, enabling the units to be rotated passed the teeth. Additionally or alternatively, a control component, such as a micro switch (not shown) is incorporated on the cover mechanism (e.g. on a cover door of the inhaler and/or in associated portions of the inhaler housing which are contacted by the cover door) and configured to electronically lock the inhaler device once the cover door is at an open position.

In some embodiments, during use of a source material unit, for example during a time period between when a unit has been pulled into a use position and when it has been returned to the cartridge, the inhaler cover door remains locked, for example so as to prevent removal of the cartridge during use. In some embodiments, a sensing component indicates that a unit has been pulled out into use and/or that a unit is currently in a use position within the inhaler and/or that unit has been returned to the cartridge, e.g. following use. Optionally, based on an indication received from the sensing component, a locking mechanism of the cover door is actuated. For example, if the sensing component indicates that a source material unit has been pulled into use, the cover door locks, thereby preventing removal of the cartridge during use.

In some embodiments, a sensing component comprises a sensor, e.g. a pressure sensor, optical sensor (light based sensor), and/or other sensor configured for detecting whether a source material unit had been removed from the cartridge and/or for detecting if a source material unit is currently placed in the use position. In some embodiments, the sensing component comprises a mechanical element, e.g. a latch.

In some embodiments, the sensing component is configured in the cartridge itself. Additionally or alternatively, the sensing component is configured in the inhaler, e.g. in the cavity in which the cartridge is received.

In some embodiments, once a source material unit is removed from the cartridge (for example pulled into the use position), the inhaler cover door locks mechanically and/or electronically, optionally until the source material unit is returned.

FIG. 12 is a flowchart of a cartridge loading method which concurrently releases locking mechanisms of the cartridge, according to some embodiments. In some embodiments, the cartridge is placed at a designated cavity of the inhaler (1201). Optionally, initial placement actuates release or partial release of a locking mechanism, for example by compressing a spring actuated mechanism. In some embodiments, the cartridge is rotated to a final (optionally locked) position with respect to the inhaler (1203). Optionally, rotation releases a restrictor of the unit coupler (such the restricting frame described hereinabove), to allow movement of the unit coupler, for example allowing the unit coupler to be pulled or pushed by a transferring element of the inhaler. In some embodiments, by closing a cover door of the inhaler over the loaded cartridge (1205), a stopper that prevented the source material units from moving (e.g. internally rotating in the cartridge housing) is released to allow advancement of the units.

FIG. 13 is a flowchart of a method for identifying a fully used cartridge, in accordance with some embodiments.

In some embodiments, a cartridge comprising a plurality of source material units is loaded onto the inhaler (1301). Then, the inhaler is activated to use the source material units (1303), for example as described hereinabove. In some embodiments, activation of the inhaler is repeated until the inhaler identifies the last source material unit in the cartridge had been used, optionally based on unit count and/or structural variations in the cartridge (1305).

In some embodiments, identifying that the cartridge is now empty of source material is carried out based on structural changes in the cartridge. In an example, the cartridge comprises a carousel of source material units, and the last slot of the carousel remains empty. In another example, the cartridge comprises a carousel of source material units, and the last unit in the carousel is a unit that does not include source material, that is, just the frame of the unit (not including the mesh through which a current is driven for heating the source material). In the first example, the inhaler controller is configured to identify an empty slot when upon activation the cartridge unit coupler is pulled up unattached to any unit, causing the electrical contacts that regularly clamp the unit to contact each other directly, thereby short circuiting the electrical contacts so that a measured electrical impedance is low. In the second example, the inhaler controller is configured to identify the frame-only unit when upon forming electrical contact with the frame (which is formed of a substantially non-conductive material), the measured electrical impedance will be high (open circuit— high or infinite resistance). Optionally, both an empty slot and an empty frame are included after the last useful unit.

Additionally or alternatively, the inhaler controller is configured to recognize that all source material units of the cartridge have been used by counting. Additionally or alternatively, the inhaler controller is configured to recognize that all source material units of the cartridge have been used by reaching the end of rotation (e.g. 360 degrees). Optionally, the controller identifies that the last "standard" unit had been used, and does not even approach the last slot in the carousel/the frame-only unit.

In some embodiments, upon receipt of the indication that the all source material units in the cartridge had been used, the cartridge may be removed from the inhaler and optionally replaced by a new cartridge (1307).

FIGS. 14A-B are an internal view (14A) and an external view (14B) of a linear cartridge comprising a unit coupler, according to some embodiments.

In some embodiments, a linear cartridge 1401 comprises a plurality of source material units 1403 that are arranged linearly with respect to each other, for example stacked one on top of the other. In some embodiments, the cartridge comprises a unit coupler 1405 which is configured to engage a source material unit for bringing the unit to and and/or from a use-position within an inhaler (such as by engaging a transferring element of an inhaler, not shown herein). In some embodiments, the unit coupler is positioned at a slot 1407 through which units are pulled from and/or inserted back into the cartridge. In some embodiments, internal movement of the source material units in the cartridge with respect to the unit coupler and the slot is actuated by a spring mechanism. In other embodiments and/or in addition to spring actuation, internal movement of the units may be driven by an electro mechanical assembly, by an electromagnetic assembly, and/or by mechanical user actuation.

FIG. 15A is a cross section view of an inhaler cavity for receiving a cartridge configured for operably coupling the cartridge to a clutch and gear mechanism, according to some embodiments.

In some embodiments, placing of a cartridge (not shown) within cavity 1501 and/or closure of an inhaler cover door (not shown) operably couples the cartridge to a mechanism configured for rotating the cartridge, for example to a rotating gear 1503 (it is noted that more than one gear may be used). In some embodiments, the rotating gear is positioned within the cavity. In some embodiments, the rotating gear is positioned directly beneath a surface of the cavity on which the cartridge is placed.

In some embodiments, a protruding element 1505 of the inhaler housing comprises an elastic element, e.g. a spring 1507. Optionally, upon placing the cartridge in the cavity and closing the cover door, the spring is pushed down by the cover door, thereby moving a clutch 1509 to engage the rotating gear 1503. The clutch 1509 may include a tooth of a gear 1510 (see FIG. 15B) from which protruding element 1505 extends.

In some embodiments, upon activation of the inhaler, rotating gear 1503 rotates the cartridge, for example until a selected source material unit is aligned relative to (e.g. directly across from) an opening through which the source unit is pulled into use (the opening is not shown in this figure, see for example opening 1113, FIGS. 11A-11B). Optionally, movement (e.g. rotation) of the plurality of source material units and/or indication slots of the cartridge is carried out by fins extending radially outwardly from the protruding element (see for example 1015, FIG. 10B). When the cartridge is placed in the cavity, the fins engage a matching aperture of the cartridge (such as aperture 809, FIG. 8A).

In some embodiments, a stopping position of the cartridge is detected, for example via a sensor. In an example, a bottom face of rotating gear 1503, schematically shown in FIG. 15B, comprises one or more abutments 1515. Optionally, the abutments are distributed circumferentially, for example in a distribution which matches the position of source material units, for example, one abutment per two, three, four, five or intermediate, larger or smaller number of units. In some embodiments, the bottom face of the rotating gear is positioned in contact with an electronic control panel, schematically illustrated in FIG. 15C. The electronic control panel comprises one or more grooves 1517, each groove shaped and sized to receive an abutment 1515. Groove 1517 serves as a sensor, so that upon receiving an abutment, rotation of the gear may be stopped, optionally setting the units of the cartridge at a desired position and/or rotational angle.

In some embodiments, the rotating gear is activated by a stepper motor, which may advance the gear in discrete steps. Optionally, a stopper (not shown), such as a pin, is used for stopping rotation. Optionally, the stopper is positioned and configured so that the carousel does not stop amid slots, for example, at a border line between adjacent slots.

In some embodiments, a number of protrusions (e.g. teeth) of the rotating gear corresponds to the number of slots of the cartridge, for example, being a multiple of the number of slots.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In addition, any priority document(s) of this application is/are hereby incorporated herein by reference in its/their entirety.

What is claimed is:

1. A cartridge for use with an inhaler, the cartridge comprising:

a housing comprising:

a plurality of source material units; and a unit coupler contained within said cartridge, said unit coupler configured for selectively interlocking to each of the plurality of source material units, the unit coupler positioned and configured to move away from or back into the housing with an interlocked source material unit of the plurality of source material units; the unit coupler and each source material unit of the plurality of source material units being formed with an interlocking geometry in which a protrusion of one fits within a respective recess of the other, wherein the unit coupler is removable with the cartridge from the inhaler.

2. The cartridge according to claim 1, wherein the protrusion is a distal protrusion of the unit coupler, and wherein the protrusion is shaped and sized to fit within a respective recess defined in each of the source material units.

3. The cartridge according to claim 1, wherein the cartridge housing comprises a geometry defining two movement pathways: a first pathway in which the plurality of source material units are configured to slide past the unit coupler; and a second pathway in which a source material unit of the plurality of source material units that was interlocked to the unit coupler at the first pathway is configured to move together with the unit coupler along the second pathway.

4. The cartridge according to claim 3, wherein the first pathway is structured for rotational movement of the plurality of source material units relative to the unit coupler; and wherein the second pathway is structured for joint linear movement of the interlocked unit coupler and the plurality of source material units.

5. The cartridge according to claim 1, wherein the plurality of source material units are arranged on a carousel and are rotatable with respect to the unit coupler; the unit coupler being positioned radially outwardly with respect to the carousel.

6. The cartridge according to claim 1, wherein the unit coupler is located at a passageway of the cartridge housing.

7. The cartridge according to claim 1, wherein an external side of the housing of the cartridge is formed with a bulge, and wherein at least a portion of the unit coupler extends into the bulge on an inner side of the bulge.

8. The cartridge according to claim 1, wherein the unit coupler interlocks to only one source material unit of the plurality of source material units at a given time and only that one source material unit can be pulled away from or returned back into the cartridge.

9. The cartridge according to claim 7, wherein the bulge defines a passageway having a width that matches a thickness of a source material unit of the plurality of source material units, so that only one source material unit of the plurality of source material units can pass through the passageway at a given time.

10. The cartridge according to claim 1, comprising a restricting frame that is movable between a first position in which the restrictive frame prevents movement of the unit coupler out from the cartridge, and a second position in which an opening of the restricting frame is aligned with the unit coupler to allow movement of the unit coupler.

11. A kit comprising the cartridge according to claim 1 and an inhaler;

wherein the inhaler includes a transferring element configured to move between a proximal position within the inhaler and a distal position in which the transferring element is configured to reach out to the cartridge when the cartridge is loaded onto the inhaler, to actuate transfer of a source material unit to a use-position in the inhaler;

wherein a distal end of the transferring element is shaped and positioned with respect to the loaded cartridge such that rotation of the cartridge does not break or otherwise damage the transferring element.

12. The kit according to claim 11, wherein the transferring element is configured to connect to the unit coupler when the transferring element is at its distal position.

13. The kit according to claim 11, wherein the cartridge is substantially rounded and comprises a bulge, and wherein the distal end of the transferring element, at its distal position, extends adjacent an indentation in which the bulge of the cartridge is seated.

14. The cartridge according to claim 1, said plurality of source material units arranged within slots of a carousel; wherein one or more of the last 10% of slots in the carousel comprises an indicator for identifying that the cartridge was fully used.

15. The cartridge according to claim 14, wherein the indicator includes an empty slot that does not include a source material unit of the plurality of source material units.

16. The cartridge according to claim 14, wherein the indicator includes a source material unit of the plurality of source material units that does not include an electrically conductive member.

17. The cartridge according to claim 1, wherein said plurality of source material units are stacked or rotationally aligned with respect to the housing;

said cartridge further including at least one indicator positioned between adjacent source material units of the plurality of source material units, wherein said inhaler includes:

a cavity shaped and sized for receiving said cartridge therein; and a controller configured to infer a relative position of one or more said source material units of the cartridge based on a position of said indicator.

18. The cartridge according to claim 17, wherein the indicator comprises an empty slot or a source material unit of the plurality of source material units having a structure different than a structure of at least 70% of a total number of the plurality of source material units in the cartridge.

19. The cartridge according to claim 1, wherein the unit coupler is configured to be pulled away from the cartridge housing.

20. The cartridge of claim 1, wherein a distal end of the unit coupler has an interlocking geometry with the inhaler, wherein the unit coupler is attached to a first source material unit of the plurality of source material units, and following use of the first source material unit, the first source material unit is configured to be returned to the cartridge along with the unit coupler.

21. The cartridge of claim 1, wherein at least one of said plurality of source material units is configured to be interlocked with said unit coupler while the cartridge is not loaded onto the inhaler.

22. The cartridge according to claim 1, wherein said cartridge is configured to release, using said inhaler, an active substance from said plurality of source material units, said active substance comprises one or more of Δ9-tetrahydrocannabinol (THC), cannabidiol (CBD), cannabigerols (CBG), cannabichromenes (CBC), cannabinol (CBN), cannabinodiol (CBDL), cannabicyclol (CBL), cannabielsoin (CBE), cannabidivarin (CBDV), tetrahydrocannabivarin (THCV) and cannabitriol (CBT).

23. The cartridge according to claim 1, wherein said cartridge is configured to release, using said inhaler, an active substance from said plurality of source material units, said active substance comprises Δ9-tetrahydrocannabinol (THC).

24. The kit of claim 11, wherein said cartridge is configured to release, using said inhaler, an active substance from said plurality of source material units, said active substance comprises one or more of Δ9-tetrahydrocannabinol (THC), cannabidiol (CBD), cannabigerols (CBG), cannabichromenes (CBC), cannabinol (CBN), cannabinodiol (CBDL), cannabicyclol (CBL), cannabielsoin (CBE), cannabidivarin (CBDV), tetrahydrocannabivarin (THCV) and cannabitriol (CBT).

25. The kit of claim 11, wherein said cartridge is configured to release, using said inhaler, an active substance from said plurality of source material units, said active substance comprises Δ9-tetrahydrocannabinol (THC).

26. An inhaler for use with a cartridge comprising a plurality of source material units, the inhaler comprises:
- an inhaler body comprising a transferring element shaped and sized to engage a unit coupler of the cartridge to pull a source material unit of the plurality of source material units into a use-position within the inhaler body; said unit coupler configured for selectively interlocking to each of the plurality of source material units,
- wherein said unit coupler is contained within the cartridge, wherein the unit coupler is removable with the cartridge from the inhaler,
- and wherein a distal end of the transferring element is shaped to attach to the unit coupler of the cartridge by a slide fit coupling.

27. The inhaler according to claim 26, wherein the transferring element, the unit coupler and the source material unit of the plurality of source material units are linearly aligned with respect to each other when the cartridge is in a locked position with respect to the inhaler.

28. The inhaler of claim 26, wherein the unit coupler is linearly aligned with the transferring element when the cartridge is seated at a final position with respect to the inhaler.

29. The inhaler of claim 26, wherein said cartridge is configured to release, using said inhaler, an active substance from said plurality of source material units, said active substance comprises one or more of Δ9-tetrahydrocannabinol (THC), cannabidiol (CBD), cannabigerols (CBG), cannabichromenes (CBC), cannabinol (CBN), cannabinodiol (CBDL), cannabicyclol (CBL), cannabielsoin (CBE), cannabidivarin (CBDV), tetrahydrocannabivarin (THCV) and cannabitriol (CBT).

30. The inhaler of claim 26, wherein said cartridge is configured to release, using said inhaler, an active substance from said plurality of source material units, said active substance comprises Δ9-tetrahydrocannabinol (THC).

31. A method for pulling a plurality of source material units from a cartridge configured for use with an inhaler, the method comprising:
- loading onto the inhaler a cartridge comprising the plurality of source material units and a unit coupler contained within the cartridge, said unit coupler configured for interlocking with each of the plurality of source material units, wherein the unit coupler is removable with the cartridge from the inhaler; and
- locking the cartridge to the inhaler while simultaneously engaging the unit coupler in preparation for pulling an interlocked source material unit of the plurality of source material units from the cartridge to a use-position within the inhaler.

32. The method according to claim 31, wherein the unit coupler in the provided cartridge is interlocked with a source material unit of the plurality of source material units before being loaded onto the inhaler.

33. The method according to claim 31, wherein interlocking a source material unit of the plurality of source material units to the unit coupler is performed simultaneously with locking the cartridge to the inhaler.

34. The method according to claim 31, wherein engaging the unit coupler comprises moving a transferring element of the inhaler to a position in which the transferring element connects to the unit coupler.

35. The method of claim 31, wherein said cartridge is configured to release, using said inhaler, an active substance from said plurality of source material units, said active substance comprises one or more of Δ9-tetrahydrocannabinol (THC), cannabidiol (CBD), cannabigerols (CBG), cannabichromenes (CBC), cannabinol (CBN), cannabinodiol (CBDL), cannabicyclol (CBL), cannabielsoin (CBE), cannabidivarin (CBDV), tetrahydrocannabivarin (THCV) and cannabitriol (CBT).

36. The method of claim 31, wherein said cartridge is configured to release, using said inhaler, an active substance from said plurality of source material units, said active substance comprises Δ9-tetrahydrocannabinol (THC).

* * * * *